United States Patent
Walters

(10) Patent No.: US 9,839,417 B2
(45) Date of Patent: Dec. 12, 2017

(54) DEPLOYMENT INSTRUMENT FOR CLOSURE DEVICE FOR PERCUTANEOUSLY SEALING PUNCTURES

(71) Applicant: Essential Medical, Inc., Exton, PA (US)

(72) Inventor: Greg Alan Walters, Exton, PA (US)

(73) Assignee: Essential Medical, Inc., Exton, PA (US)

( * ) Notice: Subject to any disclaimer, the term of this patent is extended or adjusted under 35 U.S.C. 154(b) by 300 days.

(21) Appl. No.: 14/491,362

(22) Filed: Sep. 19, 2014

(65) Prior Publication Data

US 2015/0068009 A1   Mar. 12, 2015

Related U.S. Application Data

(63) Continuation of application No. 13/111,653, filed on May 19, 2011, now Pat. No. 8,870,917.

(Continued)

(51) Int. Cl.
*A61B 17/04* (2006.01)
*A61B 17/00* (2006.01)

(52) U.S. Cl.
CPC ...... *A61B 17/0057* (2013.01); *A61B 17/0487* (2013.01); *A61B 2017/00115* (2013.01);
(Continued)

(58) Field of Classification Search
CPC ............ A61B 17/0057; A61B 17/0487; A61B 2017/00654; A61B 2017/00659;
(Continued)

(56) References Cited

U.S. PATENT DOCUMENTS 3,125,095 A    3/1964  Kaufman et al.
4,705,040 A *  11/1987 Mueller ........... A61B 17/00234
                                                  604/513

(Continued)

FOREIGN PATENT DOCUMENTS

WO    2011/156498    12/2011
WO    2013/063227    5/2013

OTHER PUBLICATIONS

PCT/US2012/061855, International Search Report & Written Opinion dated Jan. 22, 2013.

(Continued)

*Primary Examiner* — Gregory Anderson
(74) *Attorney, Agent, or Firm* — Kilpatrick Townsend & Stockton LLP

(57) ABSTRACT

A deployment instrument for deploying a closure device for sealing a percutaneous puncture in a wall of a body passageway, the deployment instrument including a carrier assembly, wherein the carrier assembly is configured to hold the closure device in a pre-deployment state, and a tensioner assembly, wherein the filament is fixedly attached to the tensioner assembly, wherein the deployment instrument is configured to increase the tension in the filament upon linear movement of the deployment instrument away from the wall of the body passageway when the closure device is anchored to the wall via the anchor such that the tension is gradually increased as the deployment instrument is moved between a first linear distance and a second linear distance greater than the first linear distance from the wall of the body passageway.

25 Claims, 85 Drawing Sheets

Related U.S. Application Data

(60) Provisional application No. 61/352,807, filed on Jun. 8, 2010.

(52) U.S. Cl.
CPC ............... *A61B 2017/00526* (2013.01); *A61B 2017/00654* (2013.01); *A61B 2017/00659* (2013.01); *A61B 2017/0451* (2013.01); *A61B 2017/0454* (2013.01); *A61B 2017/0496* (2013.01); *Y10T 29/49764* (2015.01); *Y10T 29/49776* (2015.01); *Y10T 29/49908* (2015.01); *Y10T 29/49954* (2015.01)

(58) Field of Classification Search
CPC .... A61B 2017/0451; A61B 2017/0454; A61B 2017/0496
See application file for complete search history.

(56) References Cited

U.S. PATENT DOCUMENTS

| | | |
|---|---|---|
| 5,021,059 A | 6/1991 | Kensey et al. |
| 5,222,974 A | 6/1993 | Kensey et al. |
| 5,282,827 A | 2/1994 | Kensey et al. |
| 5,411,520 A | 5/1995 | Nash et al. |
| 5,531,759 A | 7/1996 | Kensey et al. |
| 5,545,178 A | 8/1996 | Kensey et al. |
| 5,662,681 A | 9/1997 | Nash et al. |
| 5,700,277 A | 12/1997 | Nash et al. |
| 5,702,421 A | 12/1997 | Schneidt |
| 6,179,863 B1 | 1/2001 | Kensey et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 7,316,704 B2 | 1/2008 | Bagaoisan et al. |
| 7,695,493 B2 | 4/2010 | Saadat et al. |
| 7,905,902 B2 | 3/2011 | Huitema et al. |
| 8,029,533 B2 | 10/2011 | Bagaoisan et al. |
| 8,337,522 B2 | 12/2012 | Ditter |
| 8,444,673 B2 | 5/2013 | Thielen et al. |
| 8,685,059 B2 | 4/2014 | Walters |
| 2001/0003158 A1 | 6/2001 | Kensey et al. |
| 2001/0044639 A1 | 11/2001 | Levinson |
| 2006/0058844 A1 | 3/2006 | White et al. |
| 2007/0123936 A1 | 5/2007 | Goldin et al. |
| 2008/0306509 A1 | 12/2008 | Osborne |
| 2009/0099598 A1 | 4/2009 | McDevitt et al. |
| 2009/0248064 A1 | 10/2009 | Preinitz |
| 2010/0168789 A1 | 7/2010 | Bagaoisan et al. |
| 2010/0179589 A1* | 7/2010 | Roorda ............... A61B 17/0057 606/213 |
| 2011/0054456 A1 | 3/2011 | Thompson et al. |
| 2011/0301619 A1 | 12/2011 | Walters |

OTHER PUBLICATIONS

PCT/US2011/039645, International Search Report and Written Opinion and International Preliminary Report on Patentability, dated Oct. 4, 2011.
EP Patent Application No. 11793097.4 filed Jun. 8, 2011, Extended European Search Report dated Oct. 12, 2016, all pages.

* cited by examiner

DEPLOYMENT INSTRUMENT FOR CLOSURE DEVICE FOR PERCUTANEOUSLY SEALING PUNCTURES

CROSS-REFERENCE TO RELATED APPLICATION(S)

The present application is a Continuation Application of U.S. patent application Ser. No. 13/111,653, filed May 19, 2011, entitled "Deployment Instrument for Closure Device for Precutaneously Sealing Punctures," which also claims priority to U.S. Provisional Patent Application No. 61/352,807, filed on Jun. 8, 2010, entitled "Closure Device," the contents of these applications are incorporated herein by reference in their entirety.

BACKGROUND

Field of the Invention

The present invention relates generally to closing percutaneous punctures, and more particularly to a self-locking closure device for sealing percutaneous punctures.

Related Art

U.S. Pat. No. 5,282,827 (hereinafter, the '827 patent), entitled Hemostatic Puncture Closure System and Method of Use, teaches systems for sealing a percutaneous incision or puncture in a blood vessel. The systems of the '827 patent comprise a closure device, an introducer, and a deployment instrument including a carrier for the closure device. The closure device has three basic components, namely, a sealing member, an intra-arterial anchor, and a positioning member. The sealing member is in the form of an elongated rod-like plug, e.g., a compressed hemostatic, resorbable collagen sponge or foam. This plug member is arranged for sealing the puncture. The anchor is an elongated, stiff, low-profile member which is arranged to be seated inside the artery against the artery wall contiguous with the puncture. The anchor is molded of non-hemostatic resorbable polymer similar to resorbable suture. The positioning member comprises a filament, e.g., a resorbable suture. The filament connects the anchor and the collagen plug (sealing member) in a pulley-like arrangement, and includes a portion extending outside the patient's body. The outwardly located filament portion is arranged to be pulled, i.e., tension applied thereto, after the anchor is located within the interior of the artery and in engagement with the inner wall of the artery contiguous with the incision or puncture. The pulling on the filament causes its pulley arrangement to move the plug in the puncture tract toward the anchor. A tamper forming a portion of the deployment instrument is slid down the filament while the filament is maintained in tension to gently tamp the plug in the puncture tract to cause the plug to deform so that its diameter increases. Tension is maintained on the filament by use of an externally located spring during the tamping procedure. The expansion of the plug within the tract is enhanced by the fact that it is formed of a compressed collagen so that it expands in the presence of blood within the puncture tract. The expansion of the plug within the puncture tract serves to hold it in place. Moreover, the closure device quickly becomes locked in place through the clotting of the hemostatic collagen plug within the puncture tract. The spring serves to hold the plug in its deformed state until such time that the plug is locked in place by the hemostatic clotting action. Once this has occurred, so that the plug is effectively locked within the puncture tract, the externally located spring can be removed. This typically occurs after approximately 30 minutes. After the spring is removed, the filament is severed at the top of the tamper. The tamper is then removed and the remaining portion of the filament is cut subcutaneously prior to the discharge of the patient. The portion of the filament connecting the anchor to the plug remains in tension, thereby holding the closure device permanently in place until it is eventually absorbed by the patient's body.

U.S. Pat. No. 5,662,681 (hereinafter, the '681 patent), entitled Self-locking Closure for Sealing Percutaneous Punctures, also teaches systems for sealing a percutaneous incision or puncture in a blood vessel.

SUMMARY

According to one aspect of the present invention, there is a deployment instrument for deploying a closure device for sealing a percutaneous puncture in a wall of a body passageway, the closure device including an anchor, a plug and a contiguous elongate filament configured to draw the plug towards the anchor upon the application of tension to the filament in a direction away from the anchor, the deployment instrument comprising a carrier assembly, wherein the carrier assembly is configured to hold the closure device in a pre-deployment state and a tensioner assembly, wherein the deployment instrument is configured to increase the tension in the filament upon linear movement of the deployment instrument away from the wall of the body passageway when the closure device is anchored to the wall via the anchor such that the tension is gradually increased as the deployment instrument is moved between a first linear distance and a second linear distance greater than the first linear distance from the wall of the body passageway.

According to another aspect of the present invention, there is a deployment instrument for deploying a closure device for sealing a percutaneous puncture in a wall of a body passageway, the closure device including an anchor, a plug and a contiguous elongate filament configured to draw the plug towards the anchor upon the application of tension to the filament in a direction away from the anchor, the deployment instrument comprising a carrier assembly, wherein the carrier assembly is configured to hold the closure device in a pre-deployment state and a tamper assembly including a frame and a tamper body, the tamper body including a tamping end and a frame interface end opposite the tamping end, wherein the tamper body is movable relative to the frame, wherein the tamper assembly is configured to provide an increase in tamping force as the frame is moved relative to the tamper body in a direction towards the tamping end.

According to another aspect of the present invention, there is a method of sealing a percutaneous puncture in a wall of a body passageway, comprising providing a deployment instrument carrying a closure device, the closure device including an anchor, a plug and a contiguous elongate filament configured to draw the plug towards the anchor upon the application of tension to the filament in a direction away from the anchor, positioning a distal end of the deployment instrument through the puncture into the body passageway thereby positioning the anchor in the body passageway, and pulling the deployment instrument away from the puncture while the filament is connected to the deployment instrument, thereby applying a mechanically induced increasing tension force to the filament that increases with increasing distance of the deployment instrument away from the puncture to draw the anchor and the seal towards each other and into engagement with the wall of the body passageway at respectively opposite sides of the wall.

BRIEF DESCRIPTION OF THE DRAWINGS

Embodiments of the present invention are described herein with reference to the attached drawing sheets in which.

DETAILED DESCRIPTION

Figure 1A:
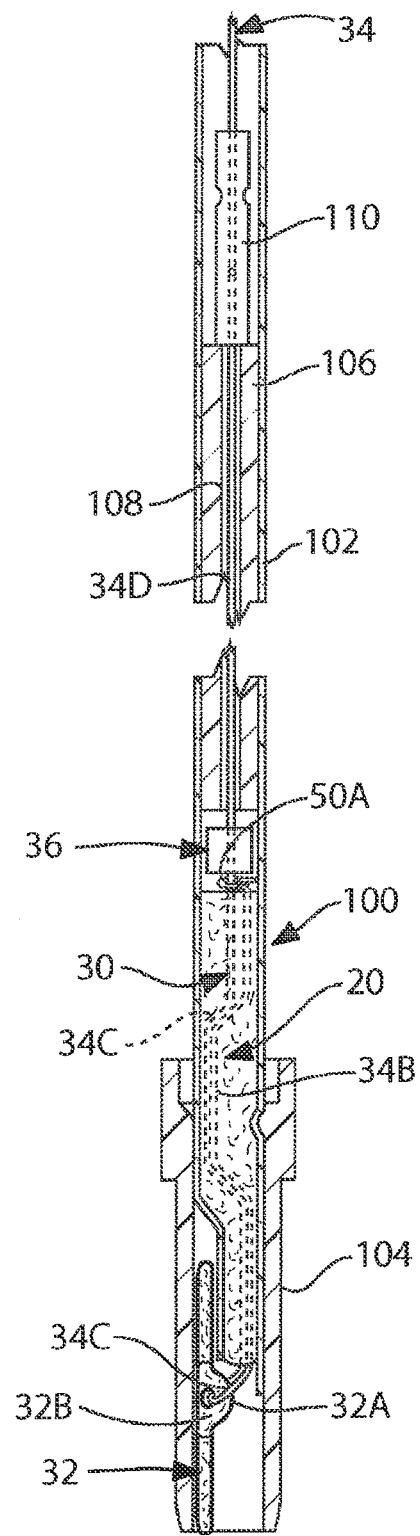
FIG. 1A is a longitudinal sectional view of the distal end of an introducing instrument holding one embodiment of the closure device of this invention prior to its deployment to plug a percutaneous incision or puncture in a body passageway, such as a blood vessel, duct, etc., of a living being.

Referring now in greater detail to the various figures of the drawings wherein like reference characters refer to like parts, here is shown at FIG. 1A a closure device 20 constructed in accordance with one embodiment and disposed within the distal end of a deployment instrument 100.

The closure device 20 is arranged for sealing a percutaneous puncture in any body passageway, such as, for example, a blood vessel, duct, etc., in the body of a living being after having been introduced therein by the deployment instrument 100. For the remainder of this application, the closure device 20 will be described with reference to sealing a percutaneous puncture in a blood vessel, e.g., the femoral artery.

Figure 1B:
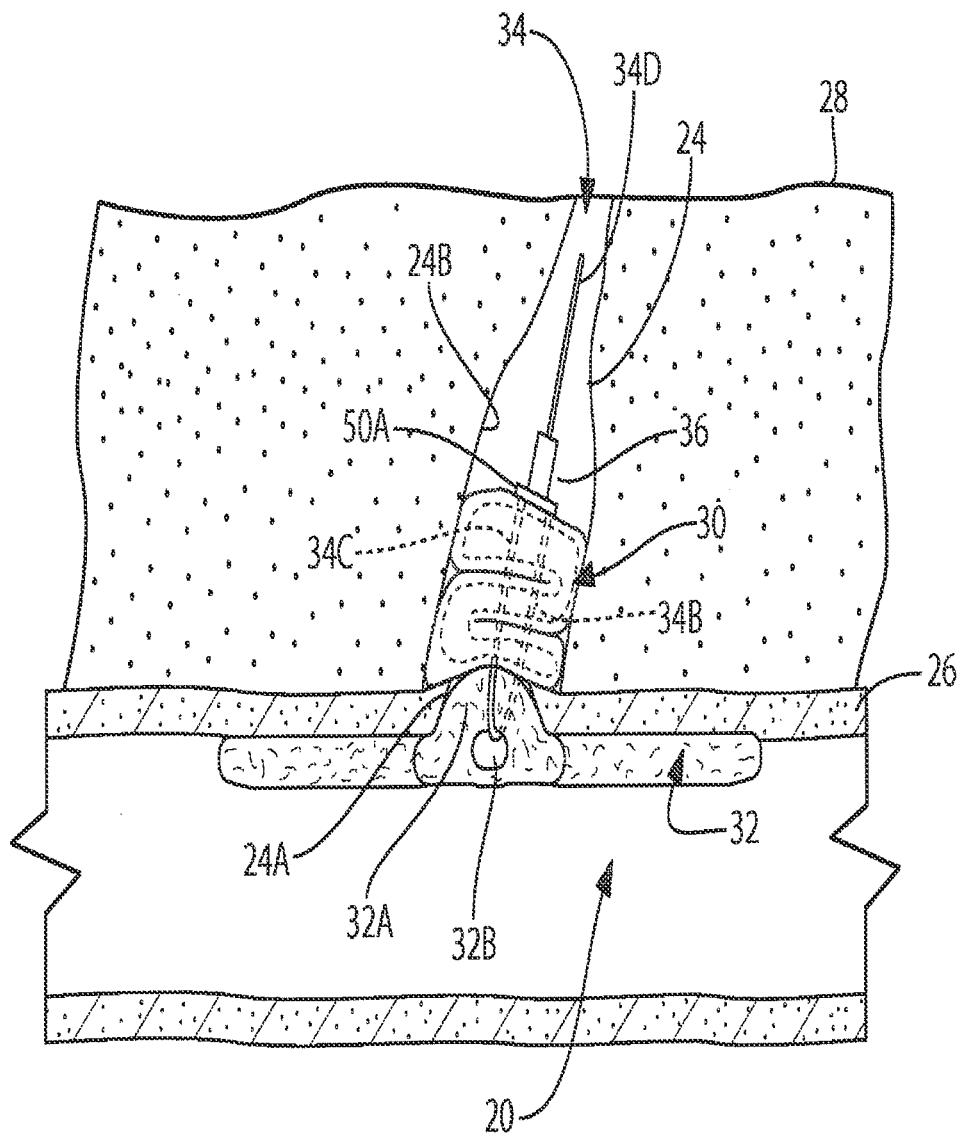
FIG. 1B is a partial sectional view showing a closure device according to an embodiment in its fully deployed state sealing a percutaneous puncture or incision in a body passageway of a living being.

In FIG. 1B the closure device 20 is shown in its fully deployed state sealing a percutaneous puncture 24 in the femoral artery 26. As can be seen therein the percutaneous puncture 24 includes an opening or a hole 24A in the artery 26 wall and a tract 24B leading up to the opening 24A. By tract it is meant the passageway in the tissue located between the artery 26 and the skin 28 of the being, and which is formed when the artery is punctured percutaneously.

To expedite the understanding of the construction and operation of this invention, the closure device 20 will first be described. Referring to FIG. 1B, the closure device 20 has four basic components, namely, plug 30 (often referred to in the art as a sealing member or collagen pad), an intra-arterial anchor 32, a positioning filament 34, and a lock 36. In an embodiment, the anchor 32 and the filament 34 are each constructed in accordance with the teachings of the aforementioned '827 patent and/or the aforementioned '681 patent, the teachings of the '827 and '681 patents relating to the construction and features of the anchor and filament being incorporated for use in an embodiment herein.

In an embodiment, the filament 34 (also referred to as suture) is a braided multifilament size 2-0 PLLA suture. The filament 34 may be made from any synthetic absorbable plastic material that degrades as needed.

Further, in an embodiment, the anchor may be constructed of a 50/50 polylactic-cogycolic acid or other synthetic absorbable polymer that degrades in the presence of water into naturally occurring metabolites (e.g., water and CO2). The anchor may be shaped like a small plank having dimensions of about 2 mm×10 mm×1 mm.

In an embodiment, the anchor 32 is a monolithic structure formed by a bio-absorbable polymer. In an embodiment, the shape of the plug 30 is constructed accordance with the teachings of the '827 patent, except for apertures (to be described later) in the plug and the manner that the filament 34 is coupled to plug 30. In an embodiment, the plug 30 is a collagen pad made of a fibrous collagen mix of insoluble and soluble collagen that is cross linked for strength. In an embodiment, the collagen may be obtained from the connective tissue of animals. The collagen may be purified from the subdermal layer of cowhide. In an embodiment, prior to use in the closure device 30, the plug 30 has dimensions of about 10 mm×30 mm×2 mm.

As with the closure devices of the '827 patent, the closure device 20 is arranged to be deployed into the percutaneous puncture 24 via the same basic introducing instrument as described in that patent. Referring to FIG. 1A, that instrument is designated by the reference number 100, and only the distal portion of it is shown herein in the interest of drawing simplicity. Thus, the deployment instrument 100 basically comprises a tubular carrier 102 formed of a somewhat flexible material to enable the carrier tube to freely pass through any conventional introducer sheath (not shown) into an operative position within the patient's artery. The distal end of the carrier tube includes a stiff sleeve or bypass tube 104 to enable the carrier tube to be inserted through a hemostasis valve (not shown) of the introducer sheath, through the sheath, and out the distal end thereof into the artery. The proximal end of the deployment instrument 100 includes a filament tensioning assembly (not shown). An elongated tamper 106 is located within the carrier tube. The tamper member 106 is constructed in accordance with the teachings of the '827 patent and includes a central passageway 108 extending longitudinally therethrough. The teachings of the '827 patent and the '681 patent relating to the tamper member and its use are incorporated by reference for inclusion in an embodiment herein.

The closure device 20 is arranged to be disposed within the distal end of the tubular carrier 102 such that it is ready for deployment into the puncture 24 in a similar manner to that described in the '827 patent. In particular, the anchor 32 is disposed longitudinally within the bypass tube 104 laterally of the central longitudinal axis of the carrier tube 102. The plug 30 is located within the carrier tube just behind (proximally) of the anchor 32 and on the opposite side of the central longitudinal axis. The lock 36 is located proximally of the plug 30, while the tamper is located proximally of the lock in the carrier tube.

In an embodiment, the anchor 32 is similar to the anchor of the '827 patent. Thus, it basically comprises a thin, narrow, strip or bar of material which is sufficiently stiff such that once it is in position within the artery, it is resistant to deformation to preclude it from bending to pass back through the puncture through which it was first introduced. In an embodiment, the surface of the anchor 32 abutting the artery wall 26 has a slight curve across the transverse axis (i.e., the axis normal to the view of FIG. 1B). In an embodiment, this curve better conforms the surface of the anchor to the curved interior surface of the artery wall 26. As can be seen in FIG. 1B, the dome-like projection 32A is arranged to extend into the opening 24A in the artery wall 26 when the anchor 32 is properly deployed within that artery, i.e., when the top surface of the anchor is in engagement with the interior of the artery contiguous with the opening 24A. The top of the projection 32A as depicted in the FIGs. is slightly flat, but in an alternate embodiment, the top is rounded. In an embodiment, the projection 32A may form a hemisphere extending from the surface of the anchor 32 that abuts the artery wall 26.

A passageway 32B of generally trapezoidal cross section, but with slightly rounded corners, extends transversely across the anchor 32 below the projection 32A and close to the bottom surface of the anchor. A portion of the filament 34 is arranged to be threaded through this passageway to couple the anchor 32 and loop 50A (described in greater detail below) together in a pulley-like arrangement with at least a portion of the plug 30 interposed between the loop 50A and the anchor.

The pulley-like arrangement of the filament cooperates with the tamper 106 to effect the movement and deformation of the plug 30 within the tract 24B once the anchor 32 is in its desired position in the artery (i.e., against the inner surface of the artery wall). This action occurs by applying tension to the filament, as will be described later.

The plug 30 basically comprises a strip of a compressible, resorbable, collagen foam, which is arranged to be straightened and compressed transversely to its longitudinal axis when it is loaded in the carrier tube 102 of the deployment instrument 100. Prior to loading into the deployment instrument, the closure device looks somewhat like that shown in FIG. 2. Thus, as can be seen, the plug 30 includes three apertures, 30A, 30B, and 30C through which portions of the filament 34 extend. When the plug 30 is compressed and linearized for location within the distal end of the carrier tube of the deployment instrument, the apertures 30A-30C are oriented to extend substantially transversely to the longitudinal axis of the plug and parallel to one another. As will be discussed in greater detail below, other configurations of the plug 30 may be utilized, with fewer or additional apertures.

The aperture 30C is located closest, out of the three apertures, to the proximal end of the plug. The aperture 30A is located closest, out of the three apertures, to the distal end of the plug. The aperture 30B is located approximately midway between the apertures 30A and 30B. The apertures 30A-30C variously serve as passageways through which the filament sections 34B and 34C pass to couple the anchor 32 to the lock 36, with the plug and the loop 50A interposed therebetween, as will be described in greater detail below.

Figure 2:
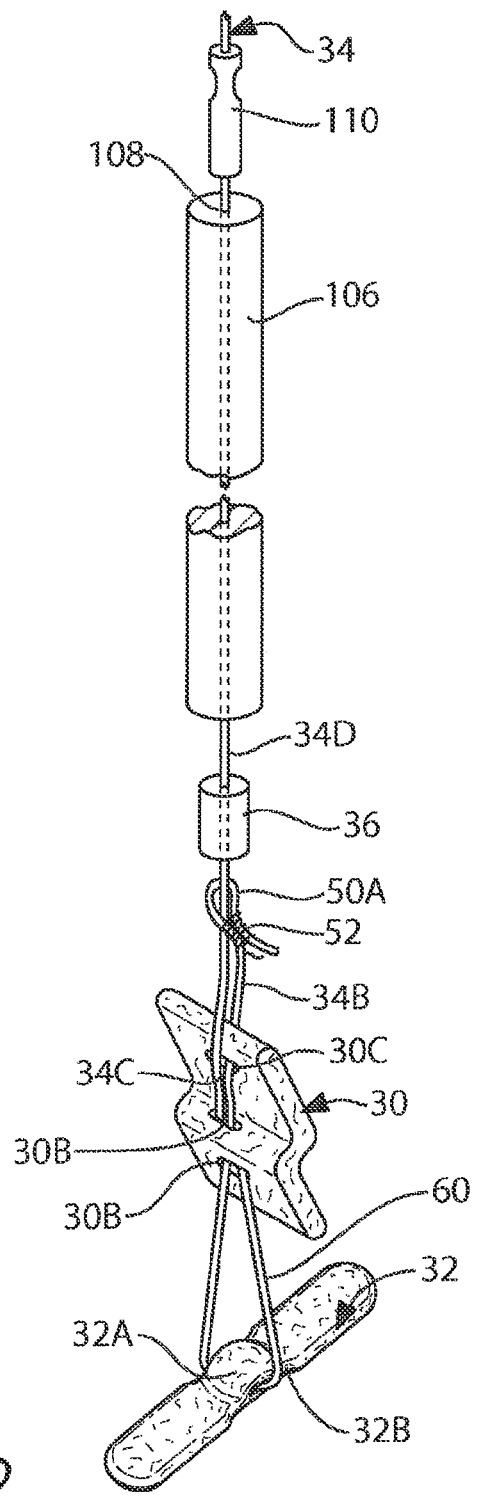
FIG. 2 is an exploded isometric view of a closure device according to an embodiment, shown after assembly of the components but prior to deployment in a living being.
Figure 10:
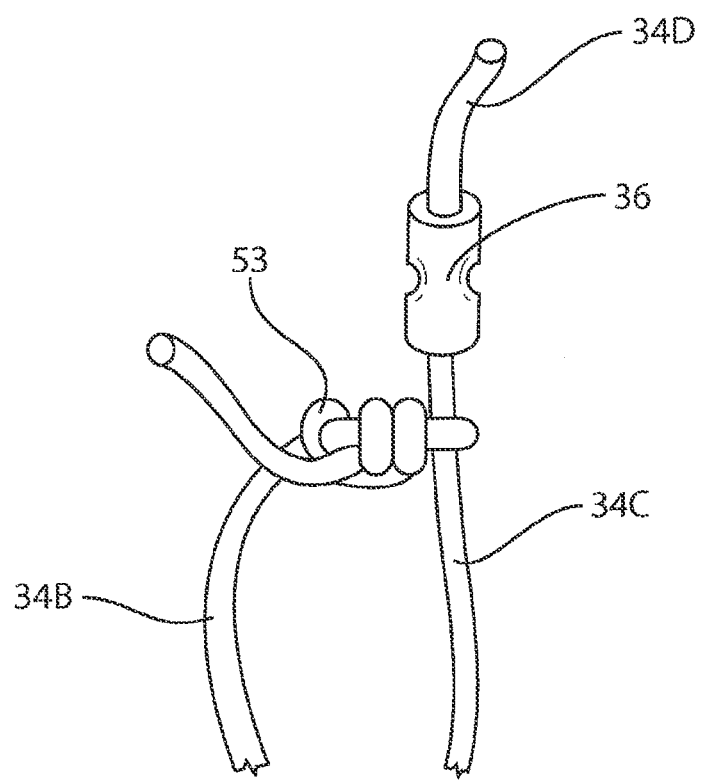
FIG. 10 depicts a loop according to an alternate embodiment.

The filament 34 is identical in construction to that of the aforementioned '827 patent, except for the path through which it extends. In particular, and as will be described in detail later, the filament is an elongated flexible resorbable member, e.g., a suture, of a single strand or multiple strands, and which is defined by a plurality of sequentially located portions or sections. As can be seen in FIG. 2, starting from one end of filament 34, the filament 34 is formed into a loop 50A located between lock 36 and plug 30. The loop 50A is configured and dimensioned to easily move along filament section 34C, which is the portion of filament 34 extending through loop 50A. Loop 50A is configured so that it may easily move along filament section 34C. Thus, loop 50A may be loosely wrapped around filament section 34C. Loop 50A is configured so as to not further tighten about filament section 34C, after it is initially wrapped around section 34C, especially during insertion of the closure device 20. Loop 50A may be formed by looping sections of the filament 34 as shown, and securing those sections by using a winding 52, as depicted in FIG. 2. In other embodiments, the loop 50A may be formed by the use of a knot 53 formed by filament 34, as may be seen in FIG. 10, and also may secure the proximal end of the collagen plug. Filament section 34B of the filament 34 extends from loop 50A to the anchor 32. Between the loop 50A and the anchor 32, filament section 34B passes through apertures 30A, 30B and 30C in plug 30, in a serpentine-like manner. Filament section 34B extends through passageway 32B in anchor 32 to join filament section 34C. Filament section 34C of filament 34 extends from the passageway 32B in the anchor 32 to the plug 30, where it passes through apertures 30A and 30B in the plug 30, and bypasses aperture 30C. In an embodiment, filament section 34C may bypass two or more apertures. Section 34C extends through loop 50A and through lock 36 to join filament section 34D. Filament section 34D extends from the lock 36 through the passageway 108 in the tamper 106, and, in some embodiments, through a tensioning mechanism (which may be a silicon tensioner as is used commercially, or a spring tensioner as is disclosed in U.S. Pat. No. 6,179,863) from whence it terminates in another free end. An exemplary embodiment of a tensioner will be detailed below. A holding sleeve or tag 110, e.g., a stainless steel tube; like that of the '827 patent, is crimped onto the filament section 34D so that it engages the proximal end of the tamper 106 to hold that member in place.

As is illustrated in FIG. 2, filament sections 34B and 34C form a loop 60. The inner diameter of loop 60 is variable and loop 60 is easily tightened because filament section 34C easily slides through loop 50A. This aspect is described in greater detail below.

In another embodiment, filament 34 may be attached to a ring in place of loop 50A. As with the loop 50A, the ring is dimensioned and configured to permit filament section 34C to easily slide through the ring. Any system that will permit the interior of loop 60 to be tightened may be utilized in some embodiments.

Herein, the term collar includes the loop 50A, a ring, or any other component that slides along filament section 34C/that permits filament section 34C to be slid through the collar to tighten loop 60.

Figure 3:
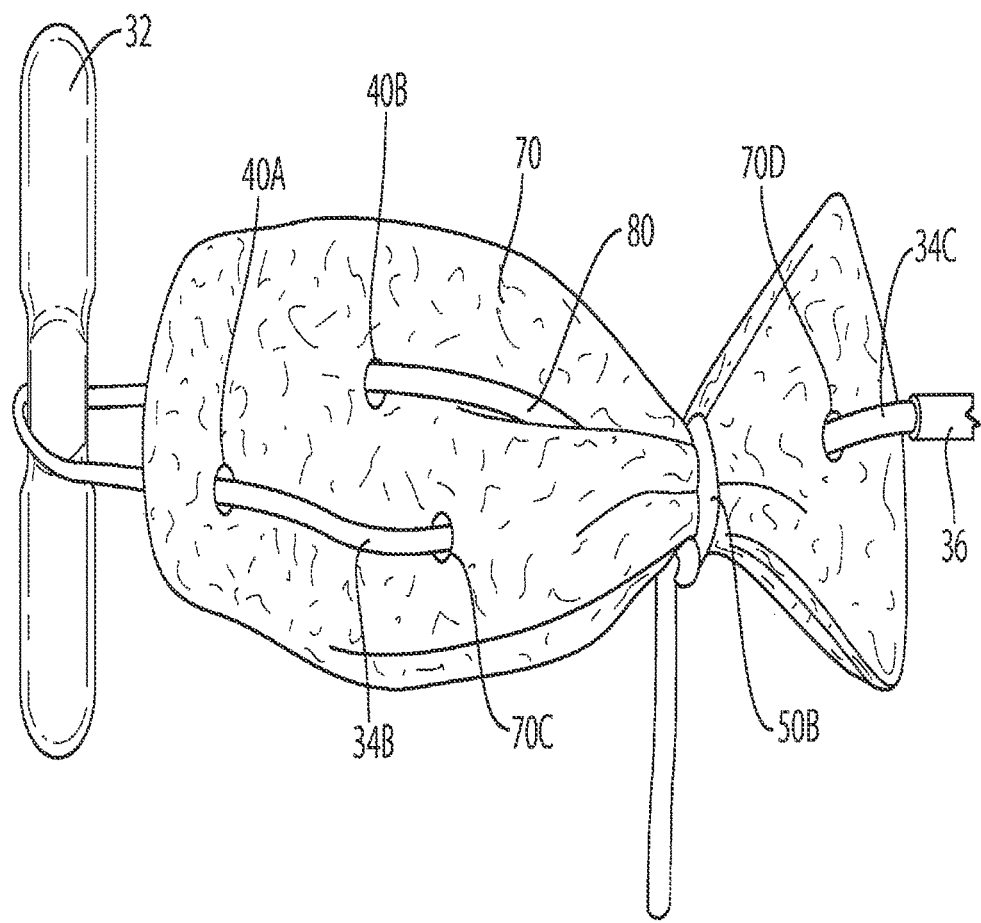
FIG. 3 depicts a closure device according to another embodiment.

FIG. 3 depicts an alternate embodiment, where one end of filament 34 is tied in a knot around plug 70. Plug 70 may be made of the same material as plug 30 described above, and may have the same exterior dimensions as plug 30. As can be seen in FIG. 3, starting from one end of filament 34, the filament 34 is formed into a loop 50B located between lock 36 and anchor 32. As compared to loop 50A, loop 50B surrounds both filament section 34C and plug 70. Plug 70 is positioned between loop 50B and filament section 34C. In an embodiment, plug 70 may be partially or fully wrapped around filament section 34C at the location proximate loop 50B, or may not be even partially wrapped around filament section 34C at the location proximate loop 50B. Loop 50B is configured so that loop 50B, along with the portion of plug 70 proximate the loop 50B, may easily move along filament section 34C. Thus, loop 50B may be loosely tied around filament section 34C and plug 70. Loop 50B is configured so as to not further tighten about filament section 34C and plug 70 (after it is initially wrapped around section 34C). Loop 50B may be formed according to any of the methods used to form loop 50A detailed above, and, in an embodiment, functions in the same manner as loop 50A, except for the fact that it is wrapped around the plug 70 and filament section 34C, as opposed to just filament section 34C.

In the embodiment of FIG. 3, filament section 34B of the filament 34 extends from loop 50B to the anchor 32. Between loop 50B and the anchor 32, filament section 34B passes through apertures 70A and 70C in plug 30. Filament section 34B extends through passageway 32B in anchor 32 to join filament section 34C. Filament section 34C of filament 34 extends from the passageway 32B in the anchor 32 to the plug 30, where it passes through apertures 70B and 70D and an intermediary aperture (not shown in FIG. 3) in the plug 30. Section 34C extends, along with a portion of plug 70, through loop 50A. In an embodiment, section 34C may extend through one, two or three or more apertures, or may not extend through any apertures, in plug 70. Section 34C further extends through lock 36 to join filament section 34D. Filament section 34D extends as described above with respect to FIG. 2.

As is illustrated in FIG. 3, filament sections 34B and 34C form a loop 80. The inner diameter of loop 80 is variable and loop 80 is easily tightened because filament section 34C easily slides through loop 50A. This aspect of the embodiment of FIG. 3 is described in greater detail below.

Figure 4:
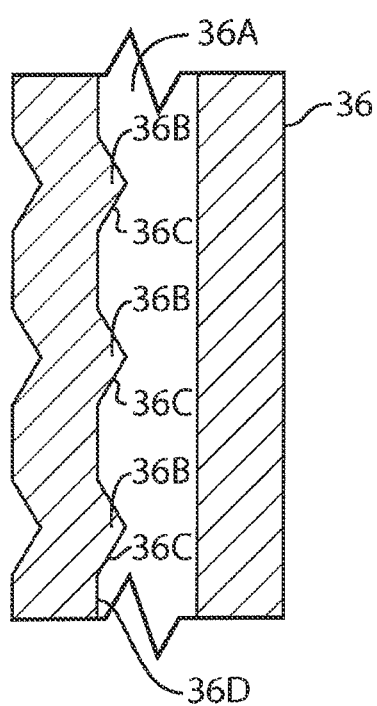
FIG. 4 depicts a lock according to an embodiment.

Referring to FIG. 4, the lock 36 comprises a cylinder including a bore 36 through the longitudinal axis of the cylinder, extending from its proximal side to its distal side. The filament 34 extends through bore 36, as may be seen in FIG. 5. In an alternate embodiment, the lock 36 may be a disk or washer-like member. In an exemplary embodiment, the lock 36 is formed of (i.e., it substantially comprises) a resorbable material, such as members of the PLLA or PGA family of synthetic polymers, or a bio-corrodible material such as iron or magnesium or another type of metal. In an alternate embodiment, the lock 36 is made from (i.e., it substantially comprises) a non-resorbable material such as, for example, stainless steel, titanium, etc.

Figure 5:
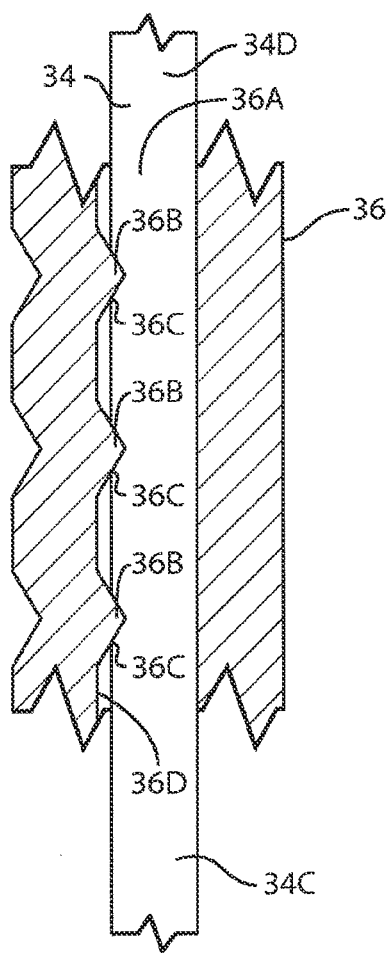
FIG. 5 depicts the lock of FIG. 4 in application.

In the embodiment illustrated in FIGS. 4 and 5, the lock 36 is configured to slide, with resistance, along filament 34.

In an embodiment, this resistance is a result of friction between lock 36 and filament 34 created by an interference between the filament 34 and the lock 36. In the embodiment illustrated in FIGS. 3 and 4, this interference is achieved due to protrusions 36B protruding into the bore 36A.

According to the embodiments presented herein, the lock 36 has an outer diameter, when measured normal to the longitudinal axis of the lock 36, which is greater than the corresponding interior diameter of loops 50A and 50B. This permits the lock 36 to lock the closure device 20 in place, as the loops 50A and 50B cannot slip past the lock 36, as will be described in greater detail below.

In an embodiment, filament section 34B is directly attached to the lock 36 instead of to the loop 50A (or collar). The lock 36 may include an orifice through which loop 50A may be looped, thus connecting filament section 34B to the lock 36. In an embodiment, the lock 36 may include a flange or the like including the orifice. In such embodiments, movement of the filament section 34C through/along lock 36 reduces the diameter of the loop 60, just as moving the filament section 34C through loop 50A reduces the diameter of the loop 60.

Still referring to FIGS. 4 and 5, as may be seen, the protrusions 36B protrude into the bore 36A. The protrusions 36B are shaped such that, with respect to the longitudinal axis of the bore 36, surfaces 36C of the protrusions 36B taper from an interior surface 36D of the bore 36, away from the interior surface 36D, and then taper back to the interior surface 36D.

As illustrated in FIG. 5, the protrusions 36B locally reduce the interior diameter of bore 36A to a diameter that is less than a corresponding local diameter of filament 34. Filament 34 is formed of a pliable material that may be locally compressed (e.g., by the protrusions 36B) but also provides resistance to that local compression by the protrusions 36B when lock 36 is moved downward along filament 34 from filament section 36D to filament section 36C. This permits the lock 36 to be moved downward but only upon application of a force to the lock. That is, the resistance to the local compression means that a force must be applied to lock 36 to move lock 36 along filament 34. This force is sufficiently high enough for lock 36 to be used to lock the plug 30 in place, as will be described in greater detail below.

In an embodiment, the lock 36 is crimped such that, with respect to the filament 34 with which it is used, to move the lock 36 along the filament 34, a force of about 0.25 to 0.5 pounds must be applied to the lock 36. In some embodiments, a force of about 0.75 pounds or about 1 pound must be applied to the lock 36 to move the lock. This force is measured as applied in the direction of the longitudinal axis of the lock 36, and is necessary to overcome the friction between the lock 36 and the filament 34. These measurements are taken when filament 34 is prevented from moving in the direction of the force.

Figure 6:
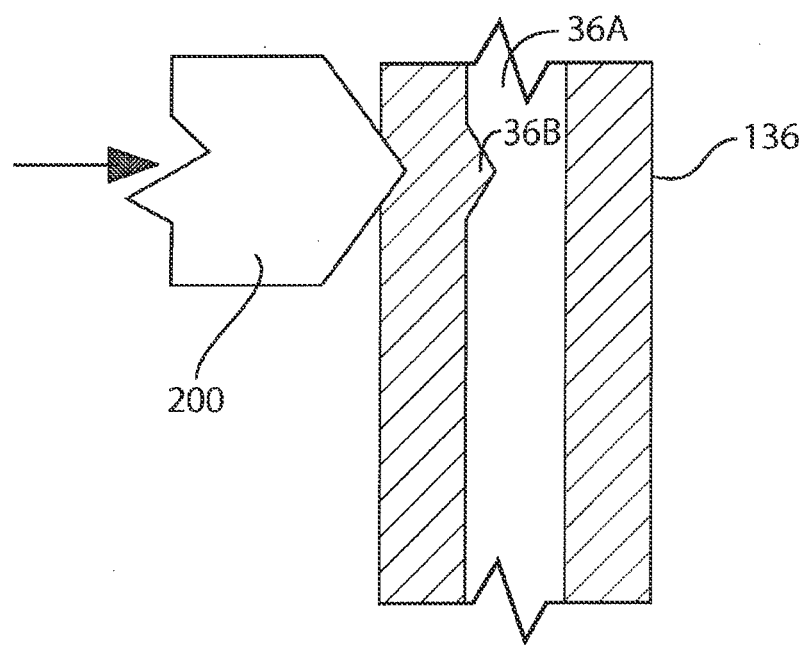
FIG. 6 depicts a method of making the lock of FIG. 4.

In an exemplary embodiment, as illustrated in FIG. 6, the protrusions 36B are formed by crimping a cylinder of an embryonic lock 136 from the outside longitudinal surface of the cylinder of the embryonic lock utilizing a crimping tool 200. In an embodiment, a press-crimp as depicted in FIG. 6 is utilized. As may be seen, a force is applied to embryonic lock 136 via crimping tool 200 sufficient to locally collapse a portion of the embryonic lock 136 so that the protrusions 36B are formed in the bore 36A. In an embodiment, the crimping tool 200 is configured to apply counter-pressure on the embryonic lock 136 so that other portions of the embryonic lock 136A do not collapse.

In the embodiment depicted in FIG. 6, the protrusions are provided in the embryonic lock 136 one at a time. However, in another embodiment, a crimping operation includes providing the protrusions in pairs, in triplets, etc., or all at the same time.

Figure 19A:
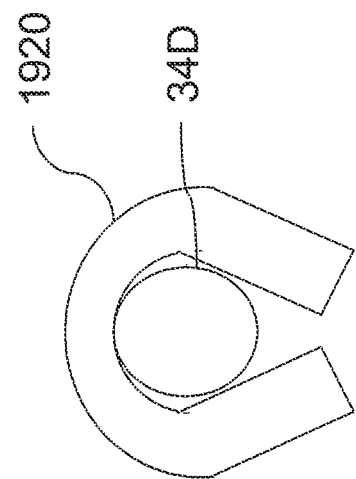
FIG. 19A depicts an alternate embodiment of an embryonic lock.
Figure 19B:
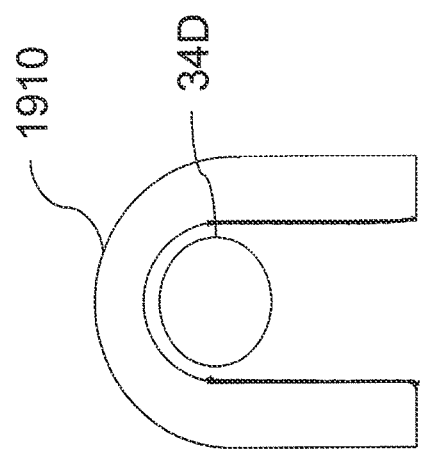
FIG. 19B depicts a lock made from the embryonic lock of FIG. 19A

FIGS. 19A and 19B present an alternate embodiment of a lock usable in some embodiments of the present invention. As may be seen, embryonic lock 1910 is in the form of a U shape instead of a cylinder with a bore. The legs of the U may be crimped as seen in FIG. 19B such that the interior of the embryonic lock 1910 collapses about filament 34D, thereby creating a friction fit between lock 1920 and filament 34. In an embodiment, the interior surface of the lock 1920 may be perforated or the like to enhance the friction fit between lock 1920 and filament 34.

Figure 17:
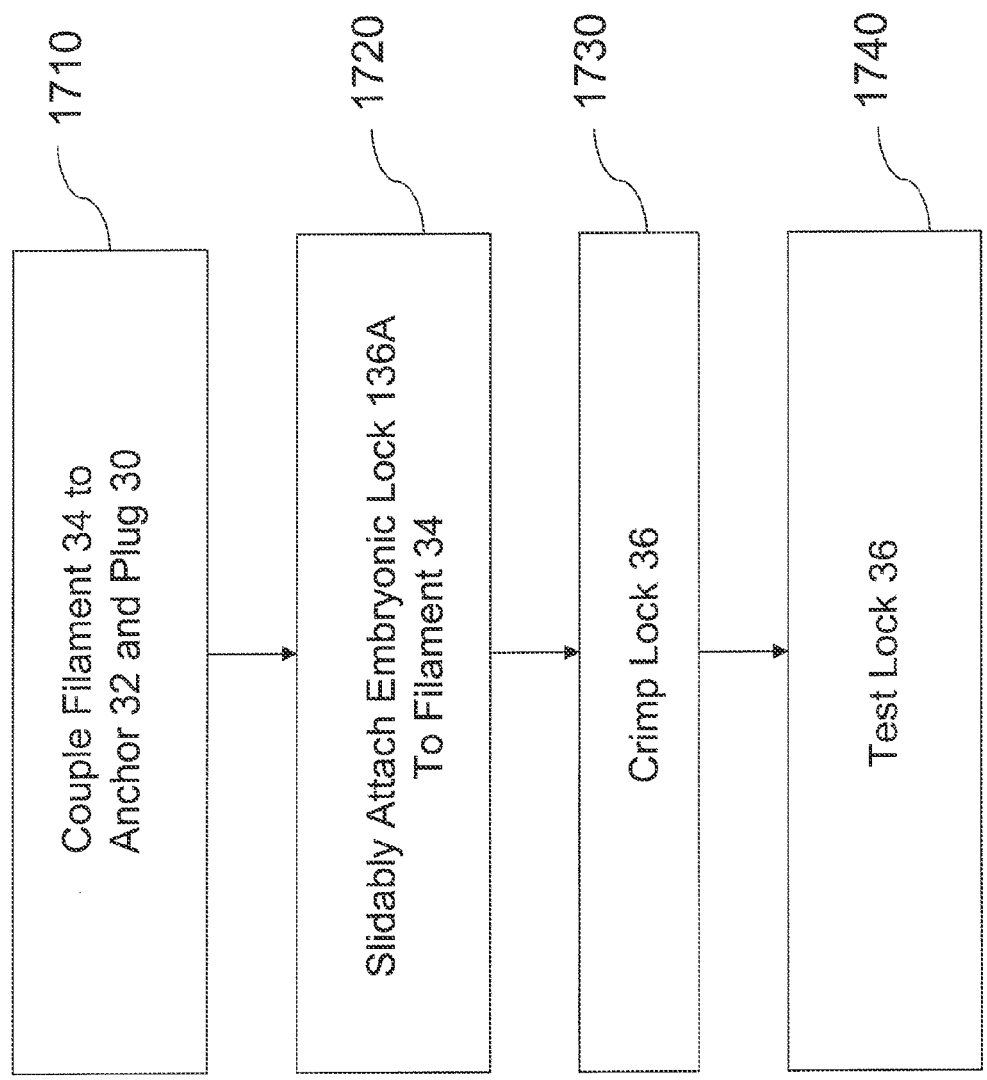
FIG. 17 depicts a flowchart for a method of assembling a closure device according to an embodiment of the present invention.

An embodiment of the present invention includes a method of making a closure device for sealing a percutaneous puncture in a wall of a body passageway of a living being, such as artery 26. By way of example, with reference to the flowchart of FIG. 17, the method comprises, as applied to the closure device detailed herein, at step 1710, coupling filament 34 to anchor 32 and to plug 30 such that the filament forms loop 60 extending through a portion of the anchor 32 and a portion of the plug 30. Proceeding to step 1720, embryonic lock 136A is slidably attached to filament 34 such that movement of filament 34 relative to embryonic lock 136A in a first direction reduces an interior diameter of the loop 60, thereby drawing anchor 32 closer to at least a portion of the plug 30. It is noted that in some embodiments, an end of filament 34 is threaded through bore 36A to slidably attach embryonic lock 136A to filament 34. In other embodiments, where embryonic lock 136A is a U shaped component as detailed above, the legs of the U straddle the filament 34.

Proceeding to step 1730, embryonic lock 136A is crimped to form lock 36 such that lock 36 frictionally engages filament 34 so that lock 36 is slidable along filament 34 only in response to application of a force on lock 36 that overcomes the frictional engagement.

The method optionally includes step 1740, which entails testing lock 36. Specifically, an embodiment of the present invention includes testing and/or evaluating the crimped embryonic lock 136 (or lock 36) to determine or otherwise verify the acceptability of the force that will be required to move the resulting lock 36 along the filament 34 after crimping, or, more precisely, after a first crimping operation. The force may be measured as detailed above. If it is determined that an unacceptably low force may be applied to move the lock 36 along filament 34 (i.e., the lock 36 does not sufficiently lock in place), after a first crimping operation, a second crimping operation may be performed. This second crimping operation may be performed either at the location of the first crimping operation on the embryonic lock 136/lock 36 (thus further driving the protrusion into the bore) or at another location on the embryonic lock 136/lock 36 (thus resulting in an additional protrusion in the bore). After this second crimping operation, a second test may be performed to determine or otherwise verify the acceptability of the force that will be required to move the resulting lock 36 along the filament 34 after this second crimping operation. These steps may be continued until an acceptable lock 36 is obtained. Further, in an embodiment, this method ensures that each closure device operates as desired, regardless of variation in the features of the component parts (e.g., out of tolerance embryonic locks 136, etc.). Further, if the testing determines/reveals that an unacceptably high force must be applied to move the lock 36 along the filament, the tested closure device may be rejected. Embodiments of the present invention include manufacturing the device whereby the amount of frictional engagement between the lock and filament may be precisely controlled during manufacture.

Figure 11:
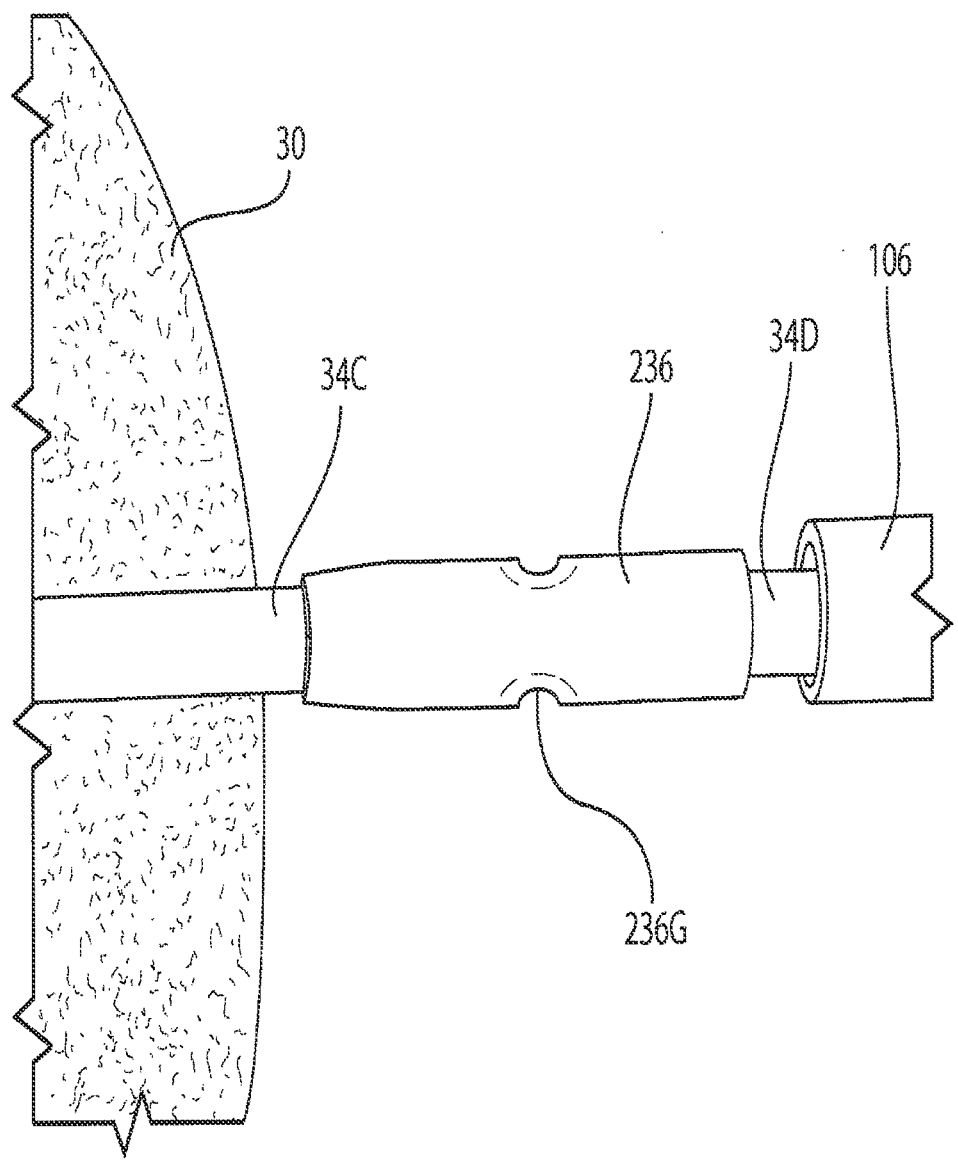
FIG. 11 depicts a lock according to an alternate embodiment.

FIG. 11 depicts an exemplary embodiment of a lock 236 manufactured according to a crimping operation just described. FIG. 11 depicts crimp locations 236G formed by crimping tool 200, where corresponding protrusions (not shown) may be found on the interior of lock 236.

In an embodiment, the crimping operation includes utilizing a machine that manually and/or automatically crimps the embryonic lock 136 and/or that provides automatic feedback with respect to the features of the crimp. By way of example, the machine could gauge the depth to which the protrusions enter the bore 36A. The machine may gauge the force applied during the crimping operation. Further by way of example, the machine could gauge the force that is necessary to apply to the lock 36 to move the lock along the filament 34. These features may be used to help assure the quality of the closure devices 20 and to help assure that the closure devices 20 will work as desired. For example, the gauged depths, forces, etc., may be compared to predetermined depths, forces, etc., to determine whether the quality is acceptable. In an exemplary embodiment, all of these actions may be performed automatically.

While filament 34 is not depicted in FIG. 6, in most embodiments, filament 34 will be located within bore 36A of embryonic lock 136 during the crimping operation. Because the filament 34 is pliable, the filament 34 will not be damaged during the crimping operation.

Figure 12A:
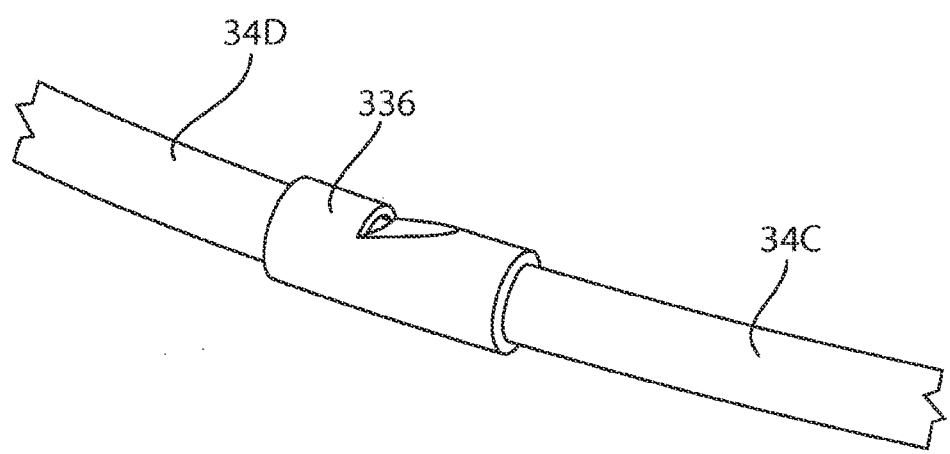
FIG. 12A depicts a lock according to an alternate embodiment.
Figure 12B:
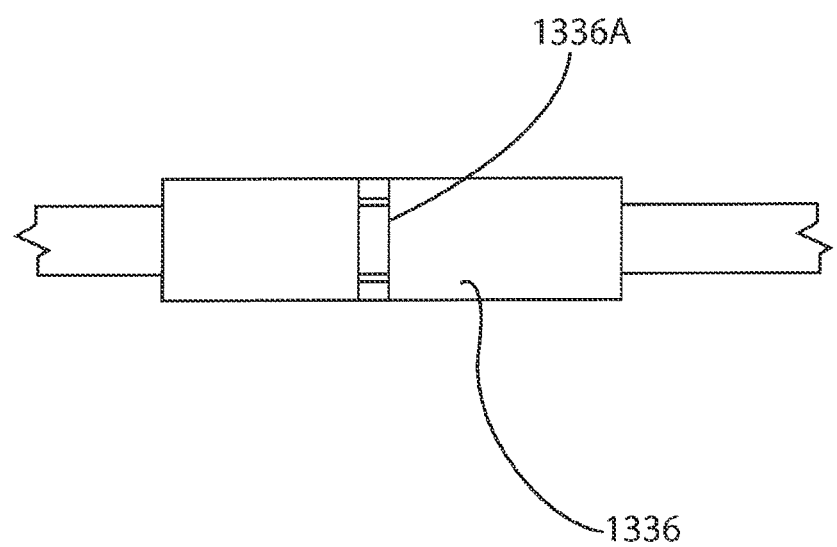
FIG. 12B depicts an embryonic lock used to make the lock of FIG. 12A.

Sections of the embryonic lock 136 may be removed prior to crimping to permit the crimping operation to be more easily performed. By way of example, laser cut slots may be formed in an embryonic lock to make the embryonic lock more bendable at those locations. In this regard, FIG. 12A depicts an exemplary embodiment of a lock 336 after crimping. Lock 336 is formed from an embryonic lock 1336, as may be seen in FIG. 12B, where slot 1336A is present in the surface of embryonic lock 1336.

Figure 13A:
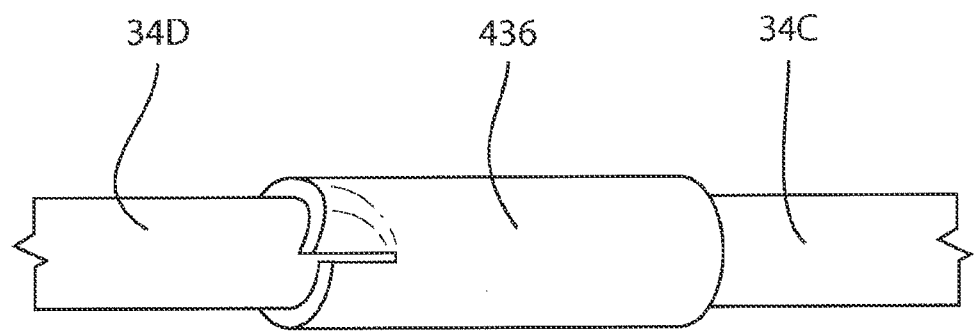
FIG. 13A depicts a lock according to an alternate embodiment.
Figure 13B:
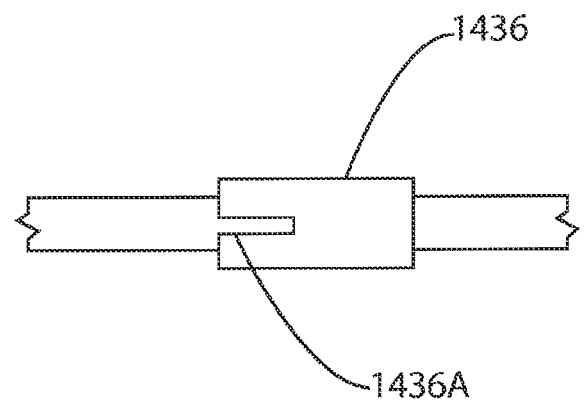
FIG. 13B depicts an embryonic lock used to make the lock of FIG. 13A.
Figure 13C:
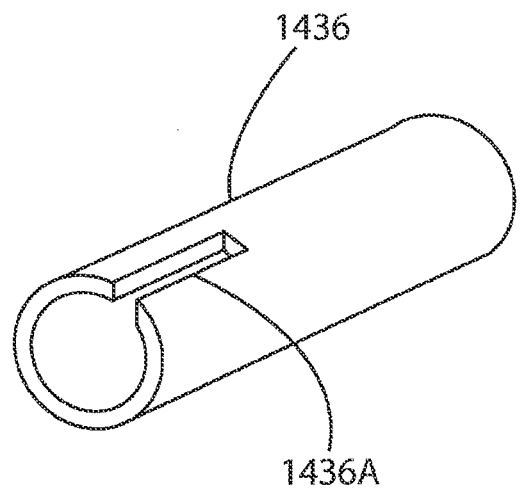
FIG. 13C depicts an isometric view of the embryonic lock of FIG. 13B.
Figure 14A:
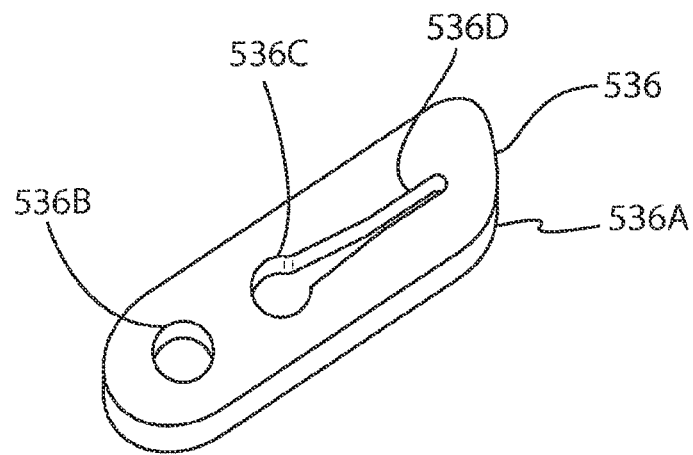
FIGS. 14A-14E depict a lock according to an alternate embodiment.
Figure 14B:
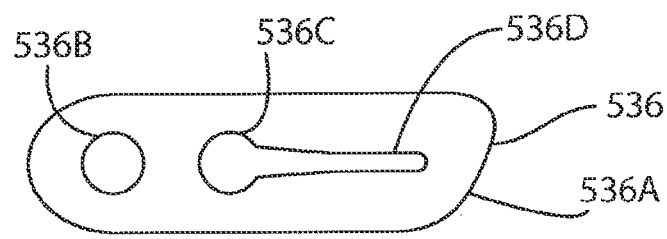
Figure 14C:
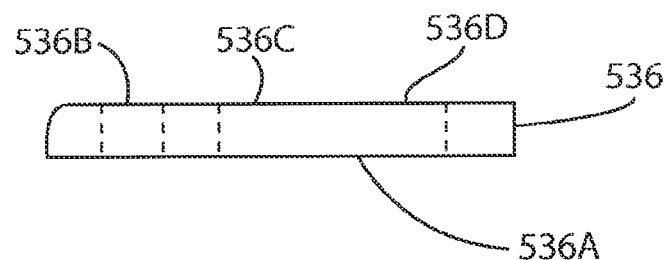
Figure 14D:
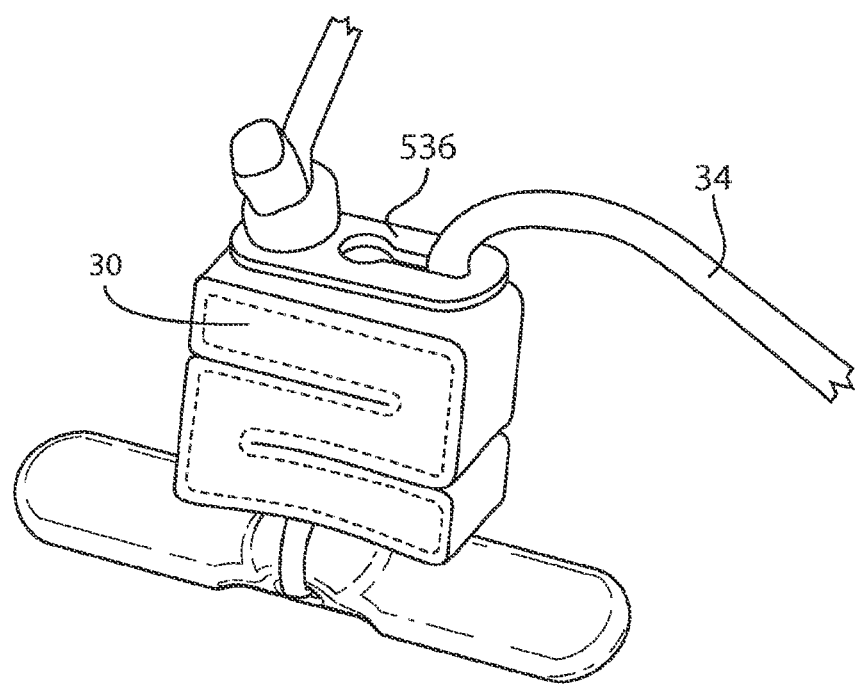
Figure 14E:
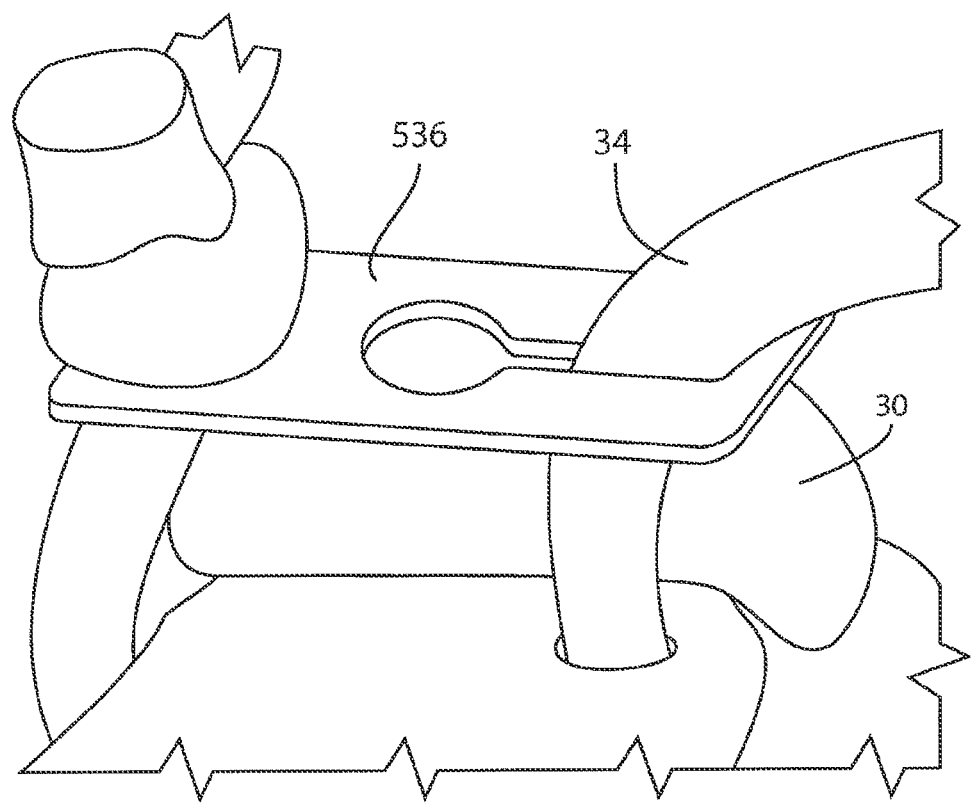

Still further, FIG. 13A depicts an exemplary embodiment of a lock 436 after crimping. Lock 436 is formed from an embryonic lock 1436, as may be seen in FIG. 13B, where slot 1436A is present in the surface of embryonic lock 1436. FIG. 13C presents an isometric view of embryonic lock 1436 of FIG. 13B. In an embodiment, the slot 1436A may be angled with respect to the longitudinal axis of the embryonic lock 2436. As will be understood, the locks depicted herein may be used in place of lock 36 as described herein.

Figure 20:
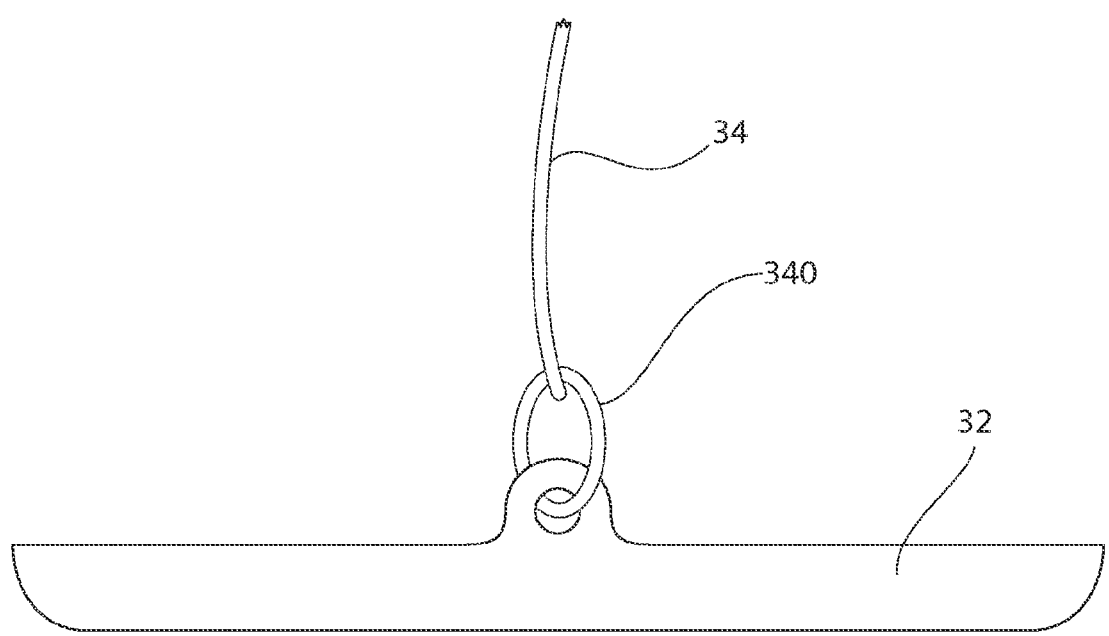
FIGS. 20 and 21 depict exemplary embodiments of components of the closure device including radio opaque components.
Figure 21:
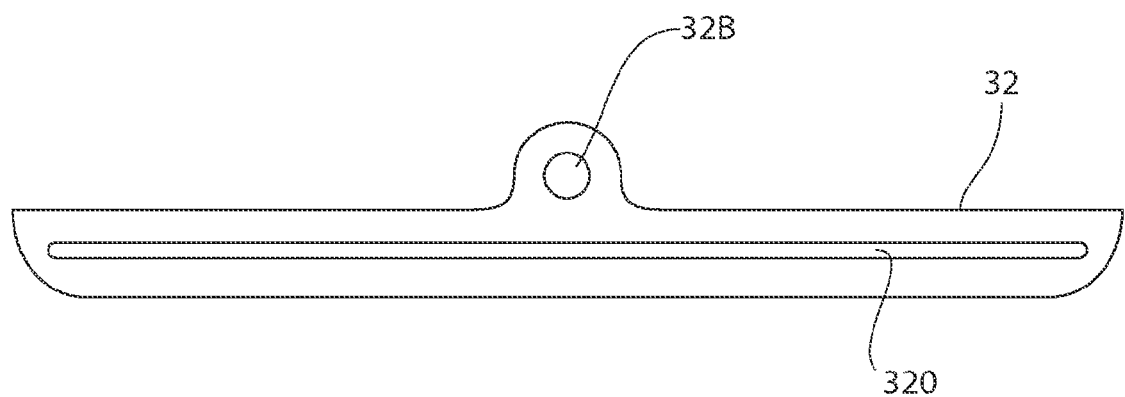

In an exemplary embodiment, the locks, such as lock 36, used with the closure device 20 may be made from iron or other appropriate resorbable material. In an exemplary embodiment, the lock may be made of a bio-absorbable polymer. Any material may be utilized so long as it is compatible with a human and can provide sufficient resistance to movement along the filament while also permitting movement along the filament and retaining loops 50A/50B in place as disclosed herein. In an embodiment, PLLA might be used to make at least some of the components of the device. Further, in an embodiment, pure or substantially pure iron is used to make the lock. In an embodiment, a radio opaque material (e.g., iron) is utilized to form the lock. This permits fluoroscopy or other non-invasive inspection regimes to be performed during and after insertion of the device to validate that the closure device has been properly inserted. In an alternate embodiment, the collar 50A is also made from a radio opaque material (e.g., iron). In yet other alternative embodiments, a radio opaque material may be added into or proximate to the anchor 32. For example, the anchor 32 may be formed around at least part of a radio opaque component and/or the filament 34 may extend through a radio opaque component located between dome 32A of anchor 32 and plug 30, etc. FIG. 20 depicts an iron ring 340 fitted thorough dome 32A, through which filament 32 extends (in other embodiments, filament 34 extends through the anchor 32 as detailed above with respect to FIG. 1B above, and the iron ring 340 also extends as shown in FIG. 20. FIG. 21 depicts an iron component 320 embedded in anchor 32. This component 320 may be molded into the anchor 32 during the molding process that may be used to form anchor 32. In this embodiment, the iron component 320 provides little, if any, structural support to the anchor 320.

Such embodiments utilizing radio opaque material as detailed herein permit a method of verifying that the lock 36 is properly positioned relative to the collar 50A using a non-invasive inspection regime. By way of example, after the closure device 20 is fully deployed (e.g., as shown in FIG. 1B), an X-Ray image taken of the recipient can be analyzed to determine the relative positions of the collar 50A and/or the lock 36 and/or the anchor 32, if the respective components include radio opaque material in sufficient quantities. This will indicating the quality of the deployment of the closure device 20 in the recipient. For example, if the X-Ray image reveals that the collar 50A is adjacent lock 36 in an embodiment where the collar 50A is positioned at the proximal end of the plug 34, it can be assumed that the closure device has been properly applied. It is noted that any radio opaque material located at any appropriate location may be utilized in some embodiments of the present invention. In some embodiments, instead of iron, the radio opaque components may be stainless steel. Foil patches may be utilized, providing that the foil patch is sufficiently radio opaque. These may be "patched" over various components of the closure device 20. For example, in the case of a collar made of PLA material or the like, the radio opaque foil may be patched over or around the collar.

As disclosed herein, the locks, such as lock 36, are made from embryonic locks in the form of elongated cylinders, and the locks retain the general characteristics of an elongated cylinder once formed. Other embodiments may include locks of different shapes. For example, locks in the general forms of rings, circular plates (with dimensions analogous to a hockey puck), balls, boxes, rectangles, etc., may be used. Any shape may be utilized so long as it is compatible with a human and can provide sufficient resistance to movement along the filament while permitting movement along the filament and retaining the loops 50A/50B in place as disclosed herein.

FIGS. 14A-14E depict a lock 536 which may be used as an alternate to lock 36. As may be seen in these figures, lock 536 includes an elongated plate 536A with holes 536B and 536C extending therethrough. Holes 536B and 536C are dimensioned to permit filament 34 to easily slide therethrough. Hole 536C includes slot 536D which is configured to act in an analogous manner to the protrusions of lock 36 described above. Specifically, the slot 536D is narrower than the natural outer diameter of filament 34, and thus provides a limited resistance to movement of filament 34 through the slot. Lock 536 may function by taking advantage of the fact that when the loop 60 is relatively large, the filament 34B is essentially parallel to the filament 34C. As the loop 60 is reduced in interior diameter, the angle between filament 34B and 34C increases, and thus the filament 34B is driven further into slot 536D away from hole 536C. In an embodiment, slot 536D becomes gradually narrower with movement away from hole 536C, thus locking the filament 34*b* in place. In another embodiment, slot 536D has a relatively constant width and does not substantially taper and/or the width is relatively constant beyond the portions proximal of hole 536C.

Deployment of the closure device 20 by the deployment instrument 100 with respect to the embodiment of FIG. 2 will now be described. It will be appreciated, however, that the deployment methods disclosed herein are applicable to deploying the embodiment of FIG. 3.

The deployment instrument is inserted into introducer sheath (which had been previously positioned in the same manner as described in the '827 patent), so that the bypass tube 104 of the carrier tube 102 passes through the hemostasis valve (not shown) of the introducer sheath (not shown). The deployment instrument is then pushed fully down the introducer sheath, whereupon the bypass tube remains in the sheath and the anchor 32 is deposited in the artery 26 beyond the distal end of the introducer sheath. The deployment instrument is then operated to determine if the anchor 32 has been properly deployed. To that end, the introducer sheath is held by the user to prevent axial movement and the instrument is carefully withdrawn from it. This action causes the anchor 32 to engage or catch on to the distal end of the introducer sheath. As the anchor catches on the distal end of the introducer, resistance will be felt by the user to indicate appropriate deployment of the anchor as described in the '827 patent.

Once the anchor 32 has been properly deployed, the plug 30 (or plug 70) is deployed into the puncture tract. To that end, the introducer sheath and the deployment instrument are held together and withdrawn as a unit from the puncture. This action causes the anchor 32 to engage or catch onto the inner surface of the artery 26 wall contiguous with the opening 24A. The introducer sheath and the instrument are then pulled further outward. Inasmuch as the anchor is trapped against the interior of the artery wall, the continued retraction of the introducer sheath and deployment instrument causes the filament 34 to pull the plug 30 (or plug 70) out of the carrier tube 102 of the deployment instrument and into the puncture tract 24B. As the introducer and deployment instrument come out of the puncture tract, continuous steady resistance will be felt as the tensioner assembly of the deployment instrument controls the force on the filament 34 during the retraction procedure.

Continued retraction of the introducer and the instrument brings the tamper 106 out of the free end of the instrument.

The retraction of the introducer sheath and the deployment instrument carries the plug 30 into engagement with the exterior of the artery wall immediately adjacent the opening 24A. Continued retraction causes the filament 34 to deform the plug 30 (or plug 70), i.e., cause it to deform radially outward. In an embodiment, the collagen is forced to fold down after exiting the carrier 102 (in some embodiments, it begins to fold down immediately upon exiting the carrier 102). The existence of blood within the puncture tract further contributes to the deformation of the plug 30 (or plug 70), since its collagen foam expands in the presence of blood. The retraction procedure continues to pull the introducer and instrument up the filament until the tag 110 is exposed. At this point the plug 30 will be located in the puncture tract contiguous with the opening in the artery, and the lock located immediately proximally of the plug.

The plug is now ready to be positioned in the tract 24B. To achieve that end, the user compacts the collagen of the plug 30 (or plug 70) by gently tensioning the filament 34 by, for example, pulling on the introducer sheath and instrument in the proximal direction with one hand. This moves loop 50A (or loop 50B) down along filament section 34C as a result of tension on filament section 34B in reaction to the tension on filament 34C. Here, anchor 32 acts in an analogous manner to a pulley as described above. This has the effect of tightening loop 60 (or loop 80). As loop 50A (or loop 50B) moves down filament section 34C to tighten loop 60, it compacts plug 30 (or plug 70). This forces plug 30 (plug 70) to conform to the artery contiguous with the opening 24A.

Next, the tamper 106 is manually slid down the filament section 34D by the user's other hand so that it enters the puncture tract 24B and engages the proximal side of the lock 36. A force is applied to tamper 106 sufficient to overcome the resistance to movement of the lock 36 relative to the filament 34 due to the protrusions 36B. This causes the lock 36 to slide down filament section 34D and onto filament section 34C until it abuts loop 50A. As noted above, the lock 36 is configured, when used in conjunction with filament 34, to provide a certain amount of resistance to movement along filament 34. This locks loop 50A (or loop 50B) in place, as the outer diameter of lock 36 is greater than the inner diameter of loop 50A, thus preventing loop 60 from expanding, because, as noted above, the lock 36 has an outer diameter, when measured normal to the longitudinal axis of the lock 36, that is greater than the corresponding interior diameter of loop 50A. This feature causes the plug 30 to be secured in the compact position until hemostasis occurs (which happens very quickly, thereby locking the closure device in place). That is, because the plug 30 is compressed between the anchor 32 and the lock 36, plug 30 is retained or locked in position within the puncture tract and cannot move away from the anchor, even before the blood clots in the plug.

With respect to the embodiment of FIG. 3, when the force is applied to tamper 106, lock 36 slides down filament section 34D and onto filament section 34C. In an embodiment, lock 36 may enter aperture 70D and continue to slide along filament section 34C unit it reaches loop 50B, where it either may directly contact loop 50B or contact a portion of plug 70 interposed between loop 50B and lock 36. In an alternate embodiment, lock 36 may not enter aperture 70D, and instead push plug 70 along filament section 34C until reaching loop 50B. In this embodiment, the lock 36 will bunch/compress plug 70 as lock 36 moves towards loop 50B.

It should be noted that in an embodiment, during the tamping action, tension on the filament section 34D may be maintained at a load greater than that used on the tamper 106 to ensure that the tamping action does not propel the plug 30 into the interior of the artery.

The locking of the closure device 20 in place is also aided by virtue of the clotting of the hemostatic collagen plug. In this regard within a few hours after deployment, the anchor 32 will be coated with fibrin and thus attached firmly to the arterial wall, thereby eliminating the possibility of distal embolization. After approximately thirty days, only a small deposit of anchor material will remain. Moreover, because the plug 30 is formed of compressed collagen or other hydrophilic material it also expands automatically in the presence of blood within the puncture tract 24A when deployed, thereby further contributing to the plug's enlargement.

As should be appreciated from the foregoing, the deployment of the closure devices of this invention is easy, quick and reliable and anchoring or locking of the closure device in place against accidental displacement is automatic upon tensioning of the filament.

An alternate embodiment of a lock 360 usable in the same manner as lock 36 detailed above will now be described with respect to FIGS. 7-9. In the embodiment illustrated in FIGS. 7 and 8, the lock 360 is configured to more easily slide downward than upward along filament 34. In the embodiment illustrated in FIGS. 7 and 8, this functionality of the lock 360 is achieved due to protrusions 360B protruding into the bore 360A. In an exemplary embodiment, as illustrated in FIG. 9, the protrusions 360B are formed by crimping a cylinder of an embryonic lock 1360 from the outside longitudinal surface of the cylinder of the embryonic lock utilizing a crimping tool 300.

Figure 7:
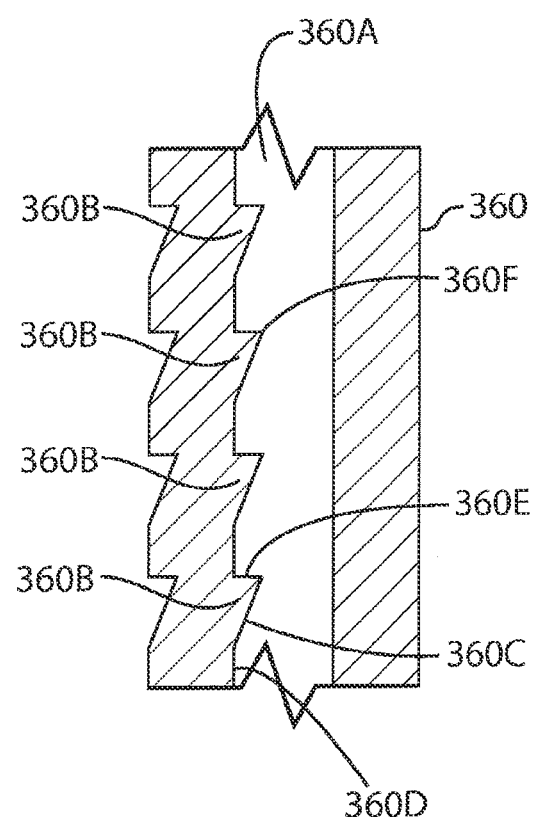
FIG. 7 depicts a lock according to an alternate embodiment.
Figure 8:
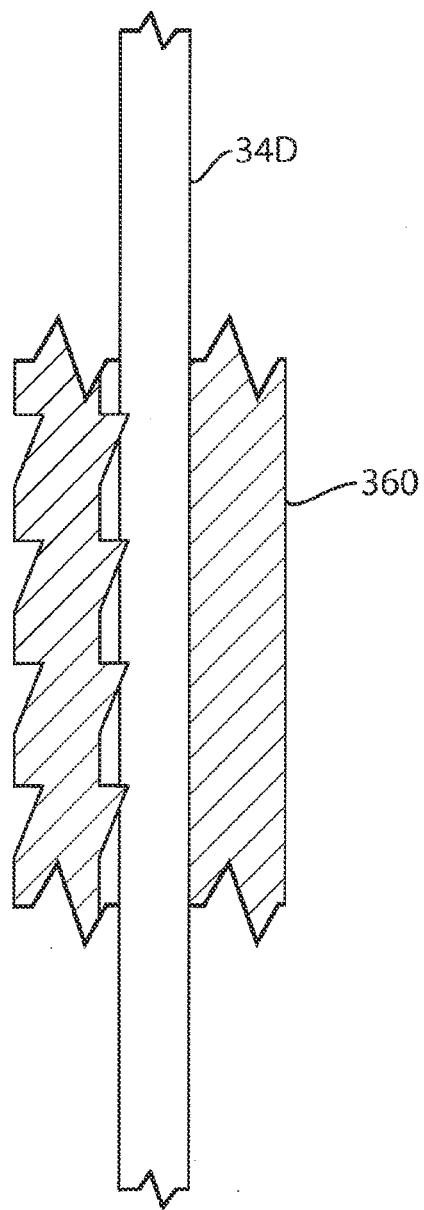
FIG. 8 depicts the lock of FIG. 7 in application.
Figure 9:
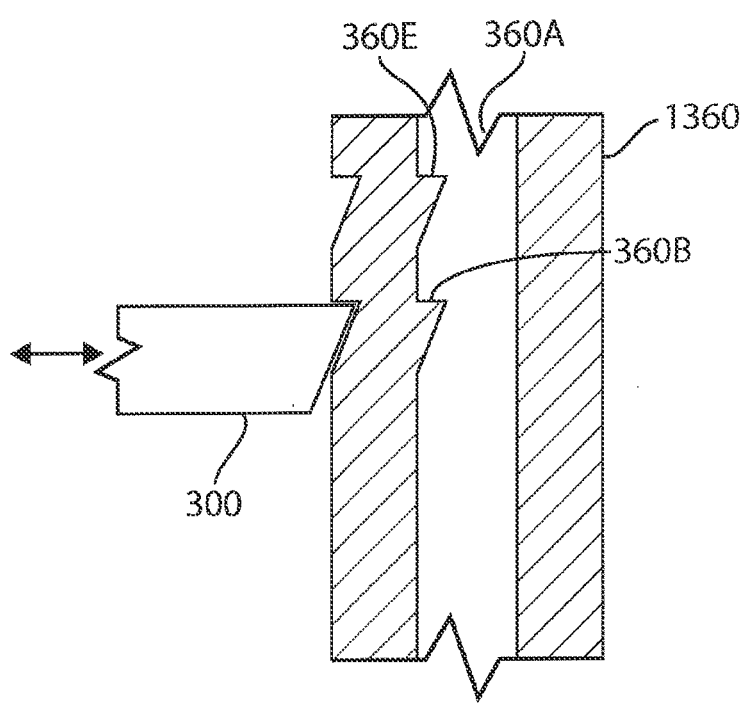
FIG. 9 depicts a method of making the lock of FIG. 7.

As may be seen in FIGS. 7 and 8, the protrusions 360B protrude into the bore 36A. The protrusions 360B are shaped such that, with respect to the longitudinal axis of the bore 360A, one surface 360C of the protrusions 360B tapers from an interior surface 360D of the bore 36. Further, another surface 360E of the protrusions 360B abruptly extend from the interior surface 360D of the bore 360A. The surfaces 360C and 360E meet to form a point at 360F.

As illustrated in FIGS. 7 and 8, the protrusions 360B locally reduce the interior diameter of bore 360A to a diameter that is less than a corresponding local diameter of filament 34. Owing to the gentle taper of surface 360C from interior surface 360D of the bore 36, and point 360F, the lock 36 may more easily slide downward than upward along filament 34. Specifically, as detailed above, filament 34 is formed of a pliable material that may be locally compressed by the gentle taper of surface 360C when lock 360 is moved downward along filament section 360D, thus permitting the lock 36 to be moved downward. However, when an upward force is applied to lock 360, the point 360F will "hook" onto filament section 34D, and will resist upward movement of the lock 36. That is, when this configuration is used, it is analogous to sliding a needle along a cloth, where the needle is held at an acute angle relative to the direction of movement of the needle. The needle will not catch on the cloth when held at the acute angle. However, if the needle is moved in the opposite direction, the needle will catch the cloth, and prevent movement of the needle in that direction. Thus, in the embodiment depicted in FIGS. 7 and 8, the lock 360 is a one-way lock.

Figure 15A:
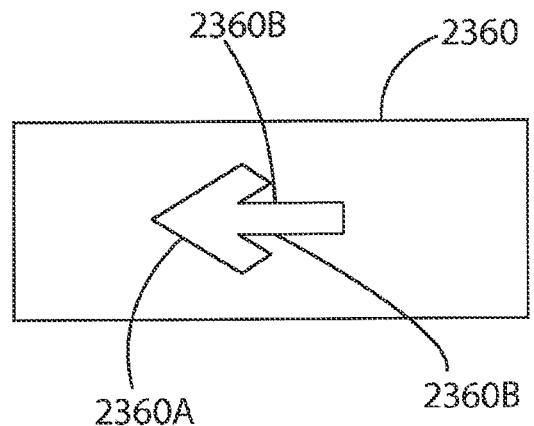
FIG. 15A depicts an alternate embodiment of an embryonic lock.
Figure 15B:
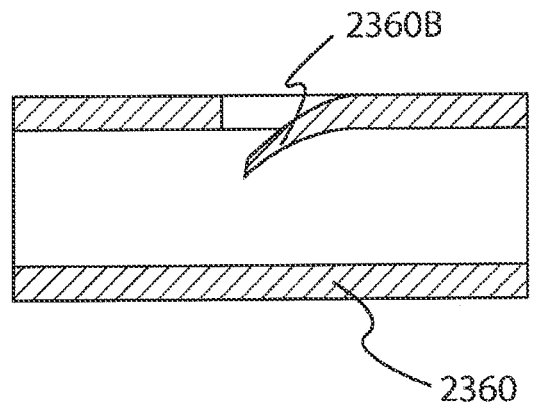
FIG. 15B depicts a lock made from the embryonic lock of FIG. 15A.
Figure 15C:
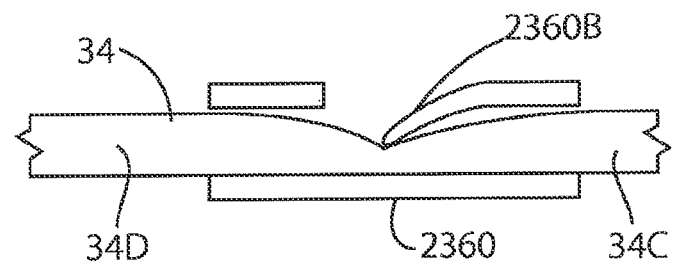
FIG. 15C depicts the lock of FIG. 15B with a filament extending through the lock.

As noted above, sections of the embryonic lock may be removed prior to crimping to permit the crimping operation to be more easily performed. This operation may also be used to make a one-way lock. Referring to FIG. 15A, in an embodiment, an arrow shape 2360A (or a wedge shape or the like) is cut into the exterior of an embryonic lock 2360 such that the "point" of the arrow (or wedge) is generally aligned with the longitudinal axis of the embryonic lock 2360. The area on the "inside" of the arrow, elements 2369B, may be bent inward into the bore of the embryonic lock, as depicted in FIGS. 15B and 15C, thus forming a one-way lock.

Note that in an embodiment, locks 336 and 436 may also be one-way locks, owing to their geometry. The cut slot in the locks may be angled with respect to the transverse axis of the locks to make the edge of the slot more likely to grip into the filament, thus making it easier for the lock to be moved in one direction along the filament as opposed to the opposite direction.

Figure 16A:
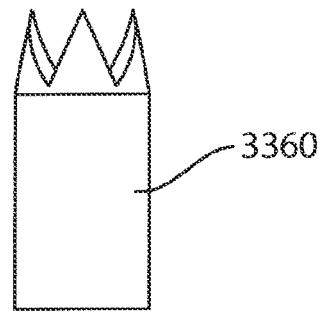
FIG. 16A depicts an alternate embodiment of an embryonic lock.
Figure 16B:
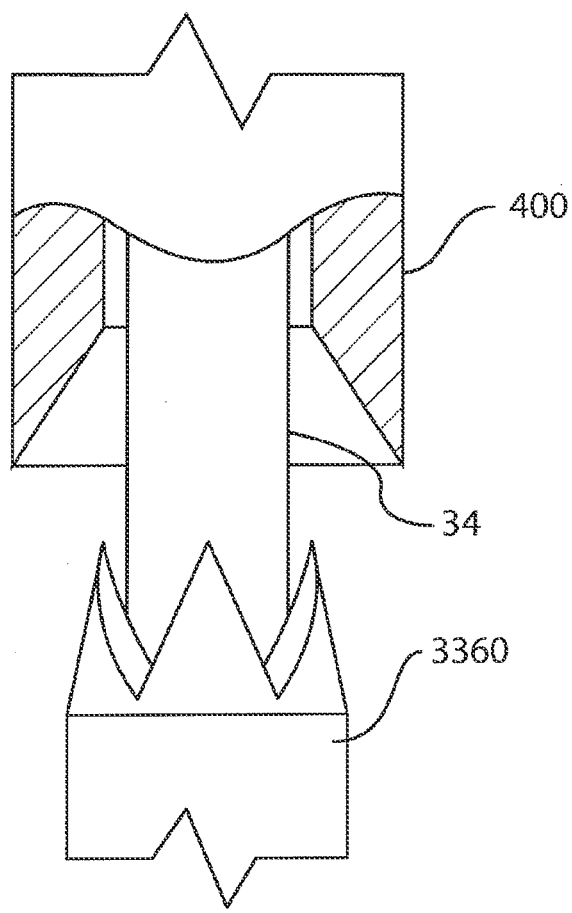
FIG. 16B depicts a method of making a lock from the embryonic lock of FIG. 16A.
Figure 16C:
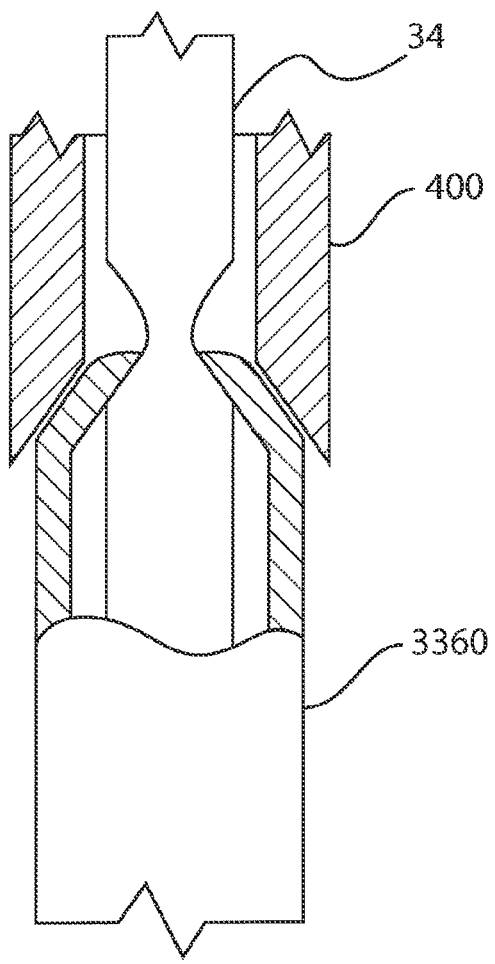
FIG. 16C depicts a lock made from the embryonic lock of FIG. 16A.

Referring to FIG. 16A, an embryonic lock 3360 that has a crown-shape at one end is utilized in an embodiment. Filament 34 is placed through the bore through embryonic lock 3360, and crimping tool 400 is forced downward onto the crown of embryonic lock 3360. Tool 400 has a tapered interior as may be seen, which forces the points of the crown inward towards filament 34, as is depicted in FIG. 16C. In an embodiment, this provides a one-way lock.

In an embodiment, tool 400 is utilized as a tamper used during application of the closure device 20. That is, in an embodiment, tool 400 is substituted for tamper 106, and embryonic lock 3360 is crimped when tool 400 is used as a tamper during application. Thus, embryonic lock 3360 is crimped at the same time that the closure device 20 is locked in place.

Figure 18:
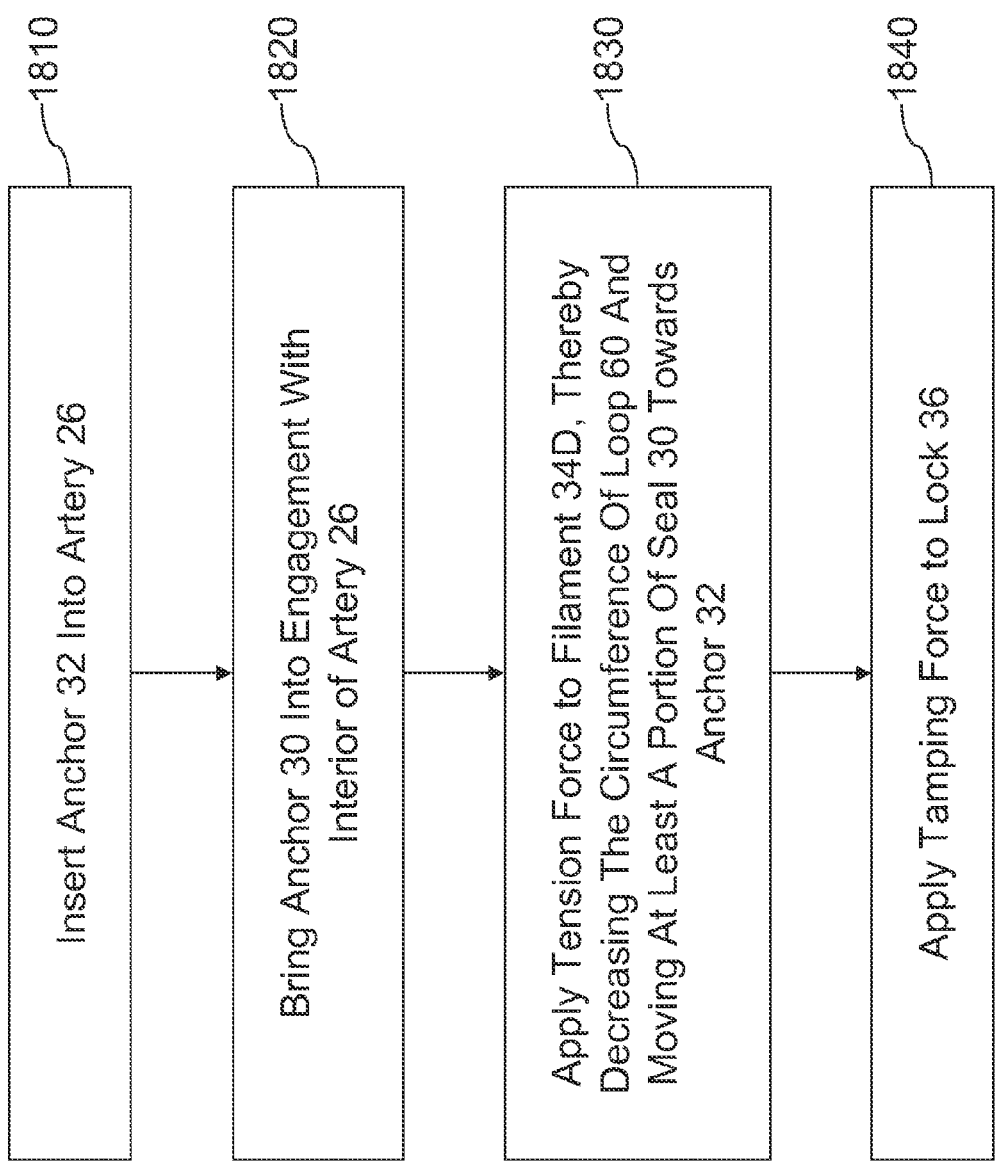
FIG. 18 depicts a flow chart for a method of sealing a percutaneous puncture in a wall of an artery according to an embodiment of the present invention.

In an exemplary embodiment, there is a method of sealing a percutaneous puncture in a body passageway, such as, for example, artery 26, of a living being. Referring by way of example to the flow chart of FIG. 18, at step 1810, anchor 32, coupled to filament loop 60, is inserted in the artery 60 through percutaneous puncture 24. At step 1820, the anchor 32 is brought into engagement with an interior of the artery 26, such as depicted by way of example in FIG. 1B. At step 1830, a tension force is applied to a portion of the filament (e.g., filament 34D) so that a force is applied to the loop 60 tending to decrease the circumference of the loop. At step 1840, a tamping force is applied to the lock 36 in a direction towards the loop 60 and in a direction away from the direction of the applied tension to filament portion 34D. The tension applied during step 1830 is maintained during application of the tamping force. The result of these steps is to reduce the circumference of the loop 60, thereby moving a portion of the seal 30 towards the anchor 32. This tamping force may be applied by tamper 106 as detailed above, or by any other device, system or method applicable. The applied tamping force is sufficient to overcome the frictional engagement forces so that the lock 60 slides along filament 34D in a direction towards anchor 32. In embodiments of the method utilizing the exemplary closure device detailed herein, the lock 60 resists movement along filament 34D in a direction opposite the direction of the tamping force. This has the effect of preventing the circumference of the loop 60 from expanding relative to the circumference of the loop 60 after application of the tamping force and the tension force.

In an embodiment, there is a method of sealing a puncture in a cardiac wall of a living being, such as the wall of the left ventricle of a human heart. The method comprises inserting an anchor coupled to a filament into an inner cavity of a heart, bringing the anchor into engagement with an interior wall of the inner cavity, and moving at least a portion of a plug toward the anchor via the application of a tension force to a portion of the filament, thereby sealing the puncture as a result of contact of the plug with heart tissue at the puncture. In an exemplary embodiment of this method, the puncture in the cardiac wall is sealed using any of the devices, systems and methods detailed herein, in part or in whole, as would be applicable to accomplish the method.

In an exemplary embodiment, the carrier tube 102 is modified or otherwise configured to act as a second catheter that is configured to extend through a first catheter. This first catheter extends from a percutaneous incision at or near a human groin to the heart, and the second catheter likewise extends such a distance. The distal end of the second catheter corresponds to the distal end of the carrier tube 102, and the proximal end of the second catheter corresponds to the proximal end of the carrier tube 102. In some embodiments, some or all elements of the deployment instrument 100 detailed herein are utilized with this second catheter. Indeed, in an exemplary embodiment, the deployment instrument 100 is configured with a carrier tube 102 or carrier tube assembly that has sufficient length to extend from the groin to the left ventricle, and a tamper 106 and filament 34 dimensioned accordingly. In such an exemplary embodiment, the distal end of the deployment instrument 100 is inserted into the first catheter, and force is applied to the carrier tube 102 to drive the distal end of the carrier tube 102 forward through the first catheter. The bypass tube may be retained outside of the body of the patient as in some of the exemplary methods detailed herein. Positioning of the distal end of the carrier tube 102/the anchor 32 relative to the heart may be accomplished via an angioscan or any other non-invasive imaging system. After the anchor 32 is positioned, sealing of the puncture is performed according to the corresponding method steps detailed herein. In an exemplary embodiment, shears or clippers are positioned with the deployment device to sever the filament 34 at a suitable location.

It is noted that in other embodiments of the present invention, the method of sealing a puncture in a cardiac wall entails some or all of the steps as detailed in the other references incorporated by reference herein, modified if and as necessary to implement application of the teachings therein to a cardiac wall puncture. It is further noted that in other embodiments of the present invention, the devices and systems used to seal a puncture in a cardiac wall entails some or all of the respective devices and systems as detailed in the other references incorporated by reference herein, modified if and as necessary to implement application of the teachings therein to a cardiac wall puncture. In an embodiment, the plugs, locks and/or filament configurations disclosed herein may be substituted for the plugs, locks and/or filament configurations of the '827 and/or the '681 patent. Further, the installation methods disclosed in those two patents may be utilized to install the closure devices disclosed herein (in a modified form as necessary to accommodate the closure devices disclosed herein). In this regard, the teachings of the '827 patent and the '681 patent are hereby incorporated by reference for combination with the closure devices disclosed herein.

Figure 22A:
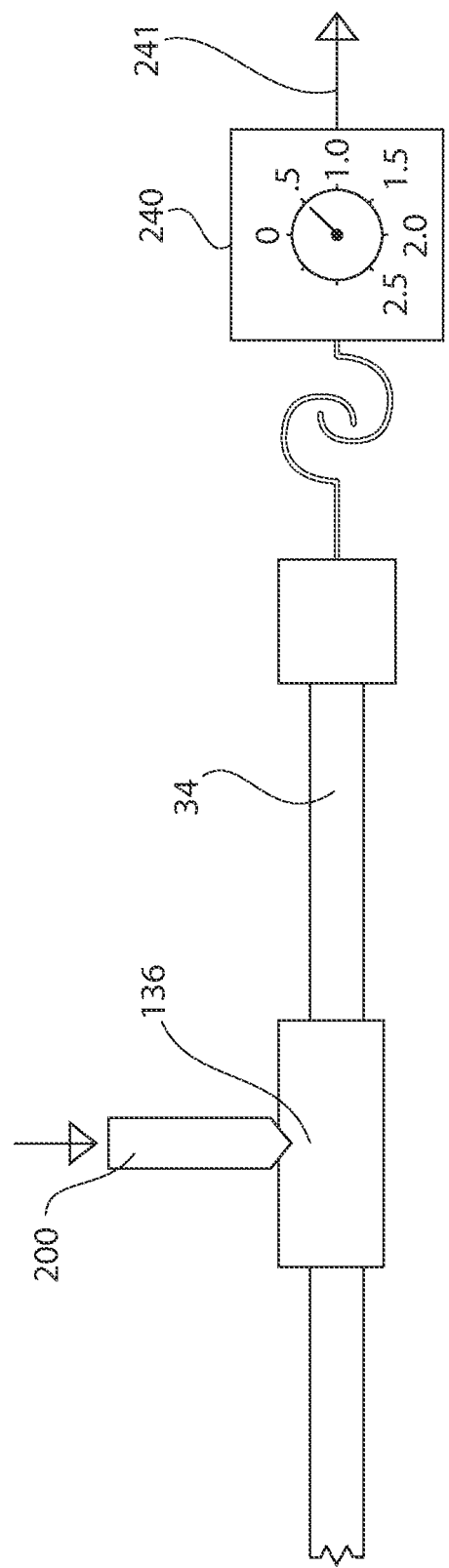
FIGS. 22A-22B depict an exemplary embodiment in which the lock is crimped whereby the requisite friction force between the lock and the filament is controlled.
Figure 22B:
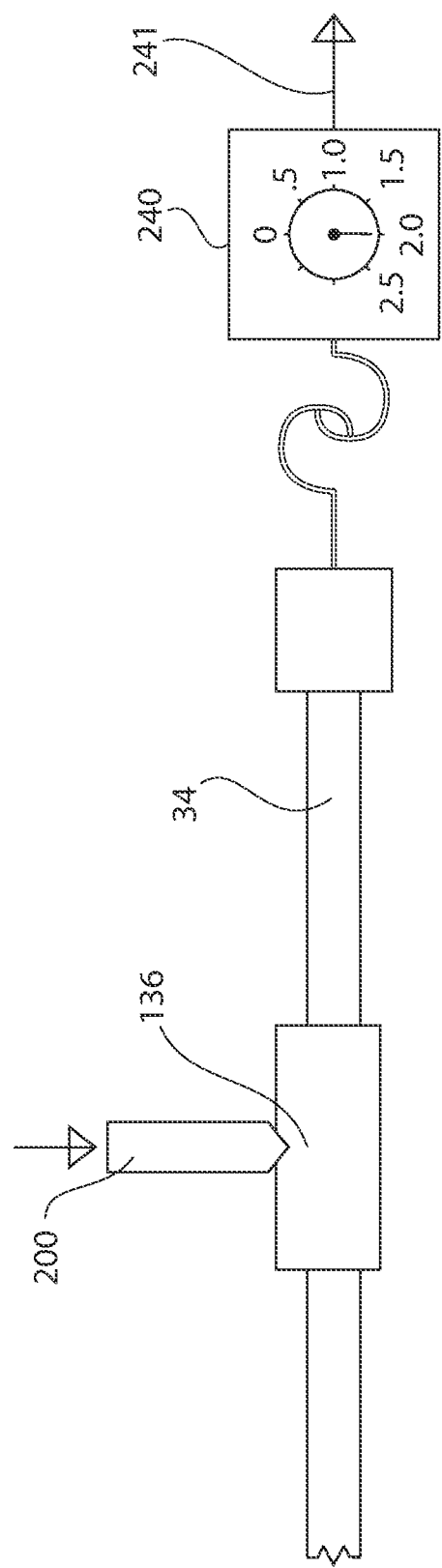

In an exemplary embodiment, there is a method of applying a crimp to an embryonic lock so that the resulting friction force necessary to be overcome to move the resulting lock relative to the filament may be controlled. In an exemplary method, the filament 34 is linked to a force gage as shown in FIG. 22A. A force is applied to the force gage 240 and thus the filament 34 in the direction of the horizontal arrow 241 while the embryonic lock 136 is crimped with variable crimp depths (i.e., distance crimp 200 is driven into embryonic lock 136). Increasing crimp depth increases the friction force between the filament 34 and the resulting lock 36 that must be overcome to move the components relative to one another. Thus, by gradually increasing the crimp depth during the crimping process, the friction force required to be overcome is also gradually increased, as may be seen by comparing FIG. 22A to FIG. 22B. As may be seen, the force gage 240 registers a higher force in FIG. 22B to move the two components relative to one another because the crimp 200 has been driven further into the embryonic lock 136. By testing/measuring the friction force as the crimp 200 is driven into the embryonic lock 136 (either continuously or in a crimp/test/crimp/test/regime) for various crimp depths and halting further crimping upon a determination that the friction force has fallen with in an acceptable range, a consistent requisite friction force may be established for each closure device 20, ensuring quality control if this method is executed for each closure device 20. This alleviates tolerancing issues because the testing is performed on each individual component.

Figure 23:
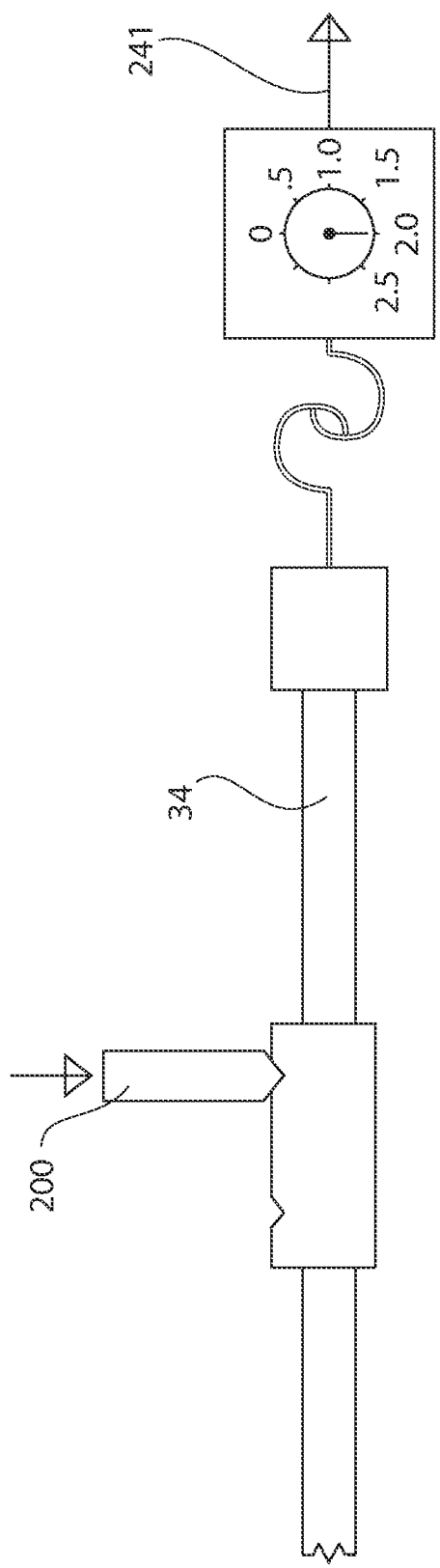
FIG. 23 depicts another exemplary embodiment in which the lock is crimped whereby the requisite friction force between the lock and the filament is controlled.

In an alternate method, instead of varying crimp depth as just detailed, additional crimps are added to the embryonic lock 136 to increase the friction force as may be seen by way of example in FIG. 23. Using a force gage 240, the friction force may be measured in the same way as detailed above. By testing/measuring the friction force as the crimp 200 is driven into the embryonic lock 136 at a new location and halting further crimping upon a determination that the friction force has fallen with in an acceptable range, a consistent requisite friction force may be established for each closure device 20, ensuring quality control if this method is executed for each closure device 20.

Figure 24A:
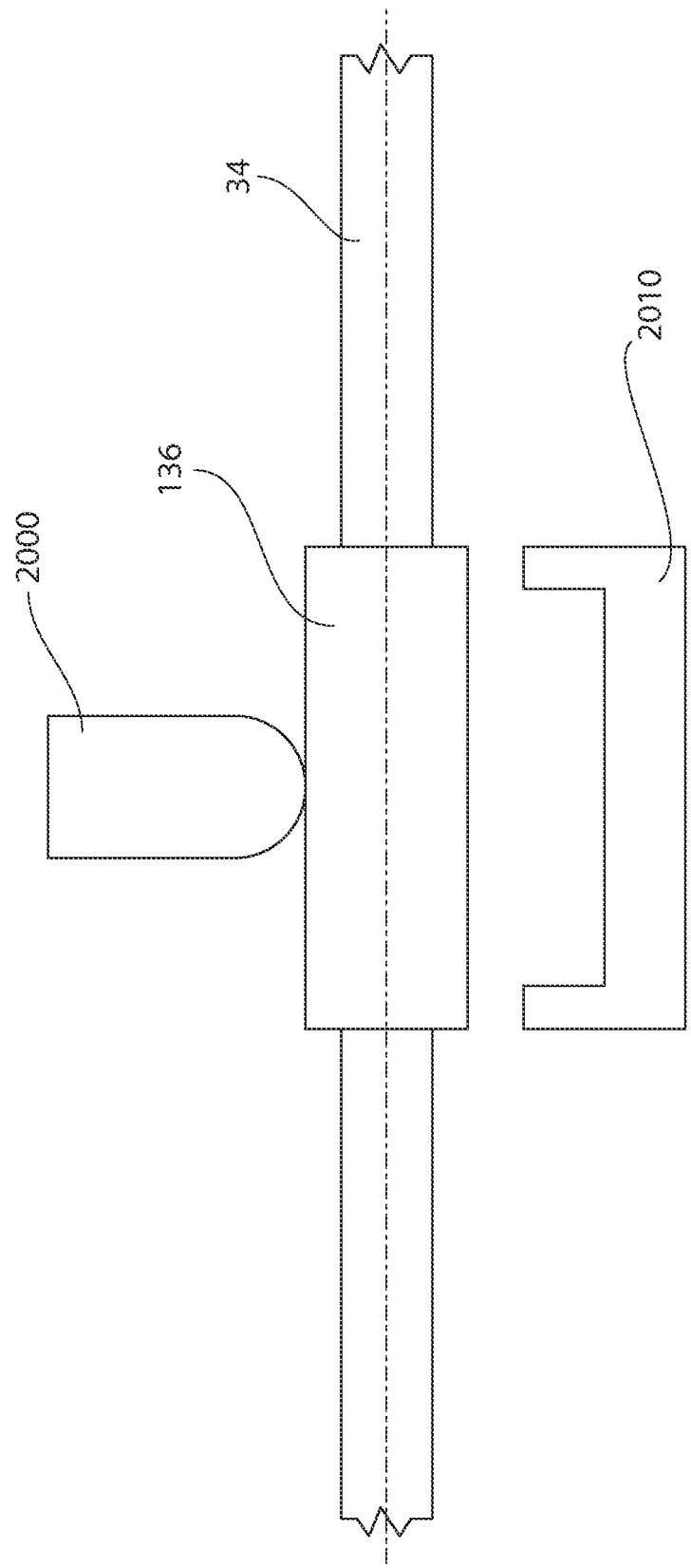
FIGS. 24A-25B depict another exemplary embodiment in which the lock is bent whereby the requisite friction force between the lock and the filament is controlled.
Figure 24B:
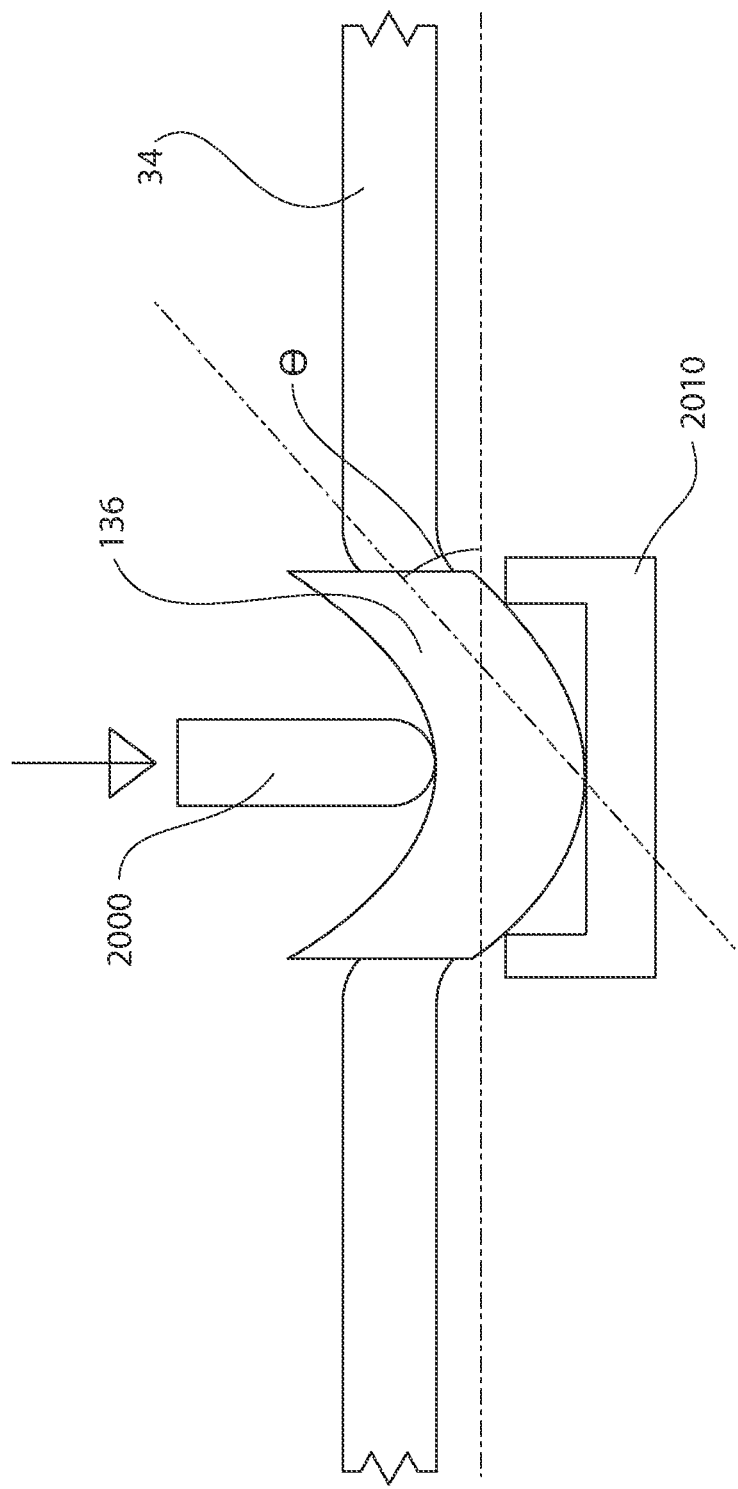
Figure 25A:
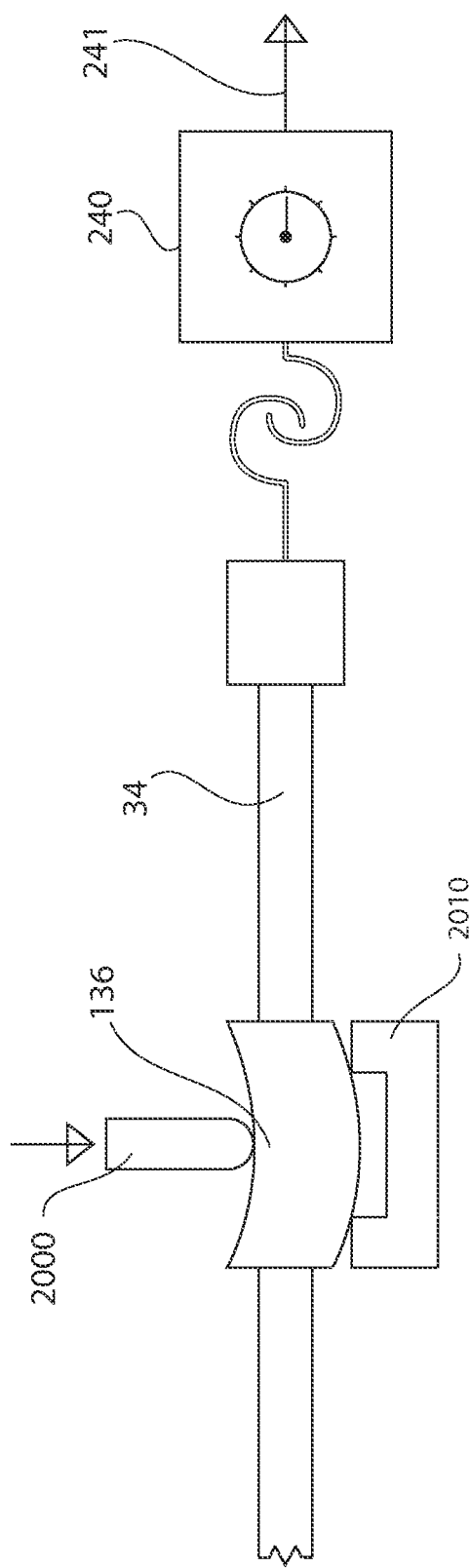
Figure 25B:
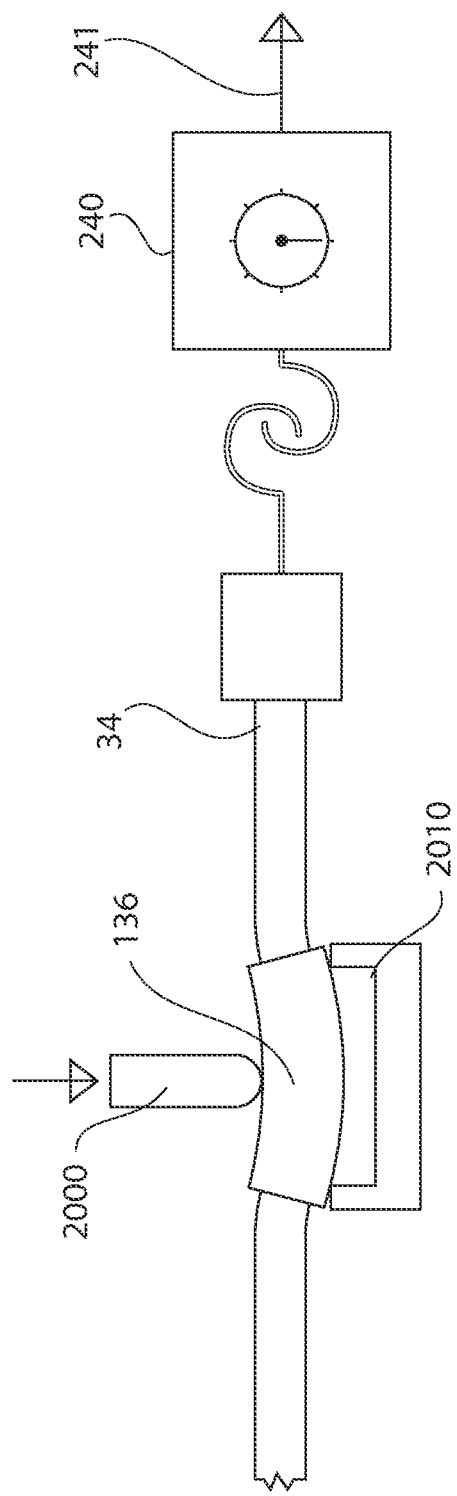

In yet another alternative embodiment, as depicted in FIGS. 24A and 24B, the embryonic lock 136 is bent to increase the friction force between the lock and the filament. FIG. 24A depicts a bending rack 2010 and a bending mandrel 2000. A downward force is applied on the bending mandrel 2000, which force is reacted against by the bending rack 2010, to bend the embryonic lock 136, as is depicted by way of example in FIG. 24B. As the angle θ of the bend increases (as seen by comparing FIG. 24A to FIG. 24B) the friction force between the lock and the filament also increases. In an exemplary method, the filament 34 is linked to a force gage as shown in FIG. 25A. A force is applied to the force gage 240 and thus the filament 34 in the direction of the horizontal arrow 241 while the embryonic lock 136 is crimped to produce a varying bend angle θ. Increasing the bend angle θ increases the friction force that must be overcome to move filament 34 relative to the resulting lock 36. Thus, by gradually increasing the bend angle θ during the bending process, the requisite friction force is also gradually increased, as may be seen by comparing FIG. 25A to FIG. 25B. As may be seen, the force gage 240 registers a higher force in FIG. 25B because the embryonic lock 136 has been bent more. By testing/measuring the friction force as the embryonic lock 136 is bent (either continuously or in a bend/test/bend/test regime) for various bend angles and halting further bending upon a determination that the requisite friction force has fallen with in an acceptable range, a consistent friction force may be created for each closure device 20, ensuring quality control if this method is executed for each closure device 20. This alleviates tolerancing issues because the testing is performed on each individual component.

Figure 26A:
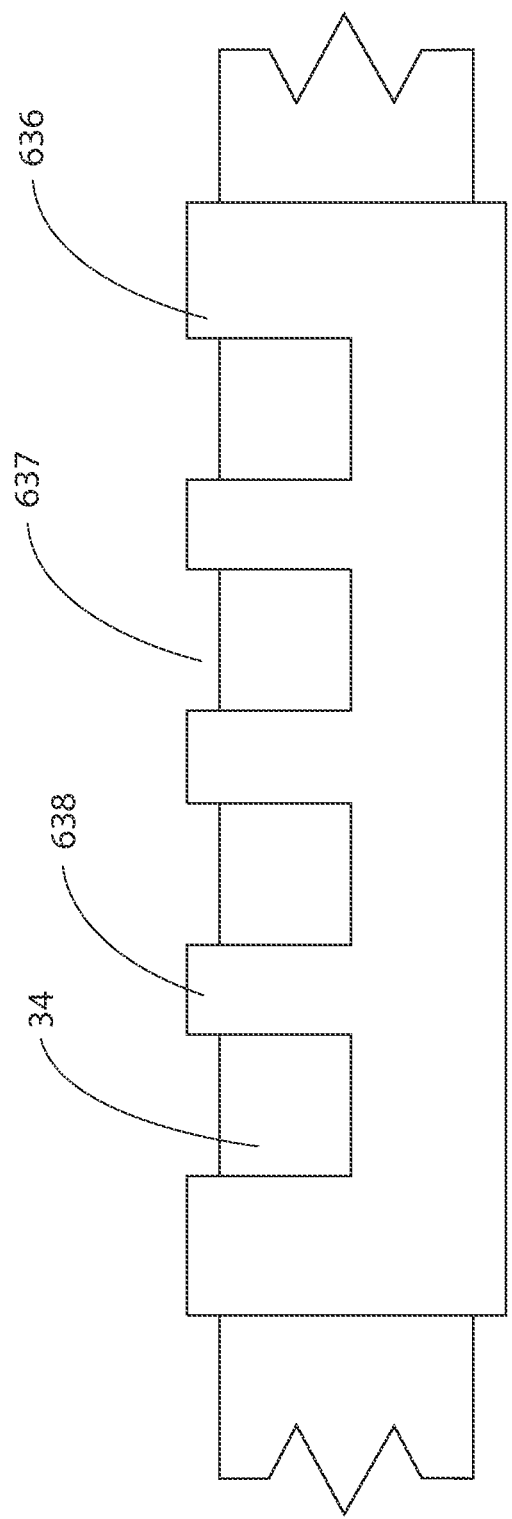
FIGS. 26A-27B depict another exemplary embodiment in which the lock is deformed whereby the requisite friction force between the lock and the filament is controlled.
Figure 26B:
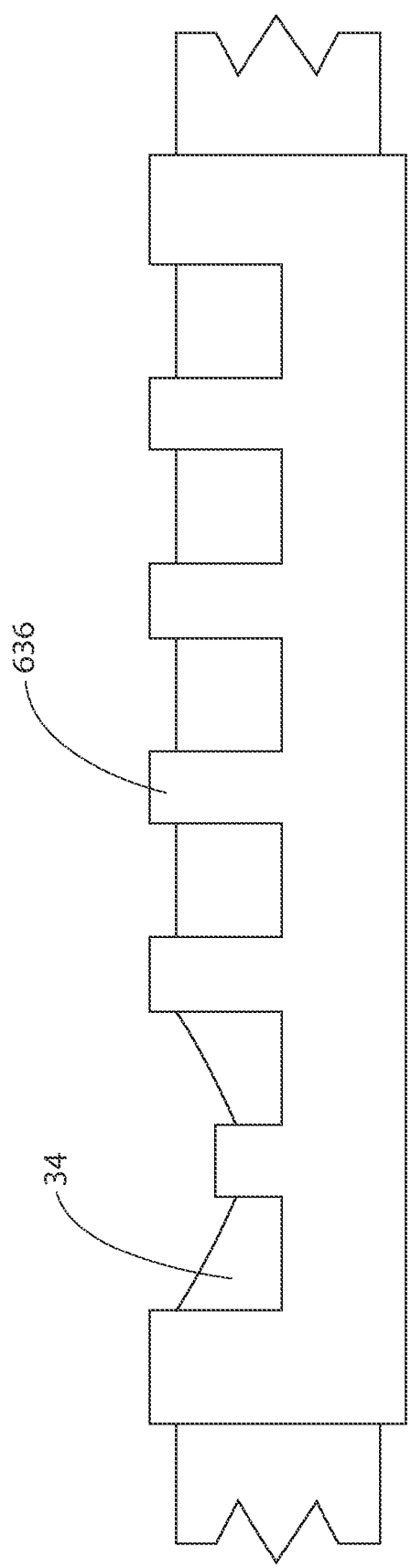
Figure 26C:
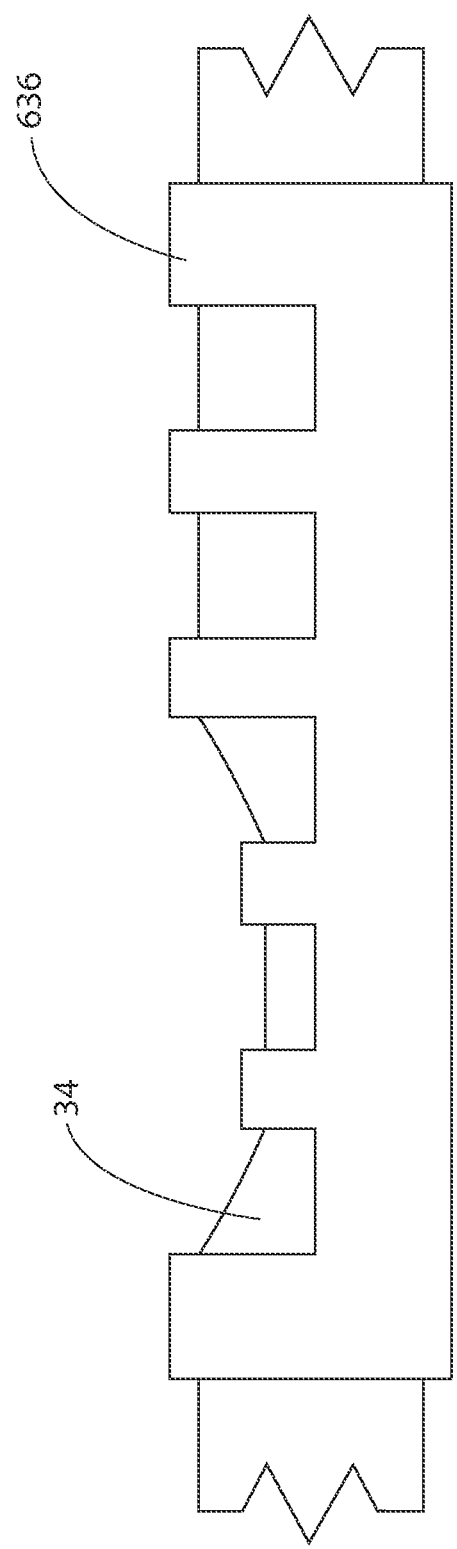
Figure 27A:
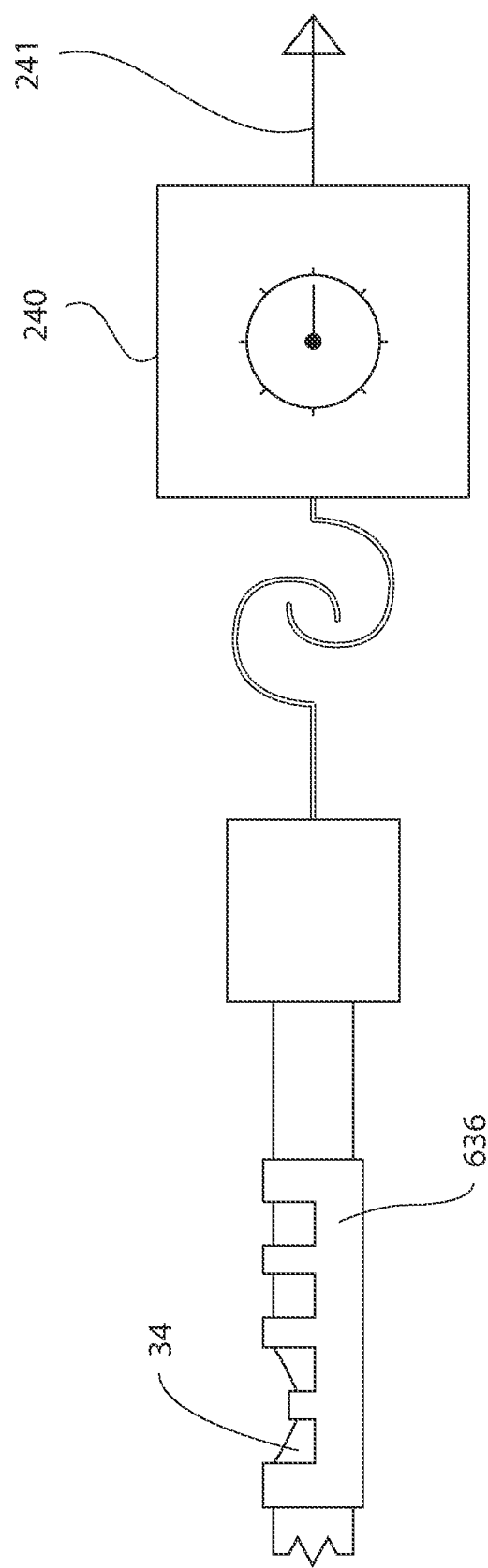
Figure 27B:
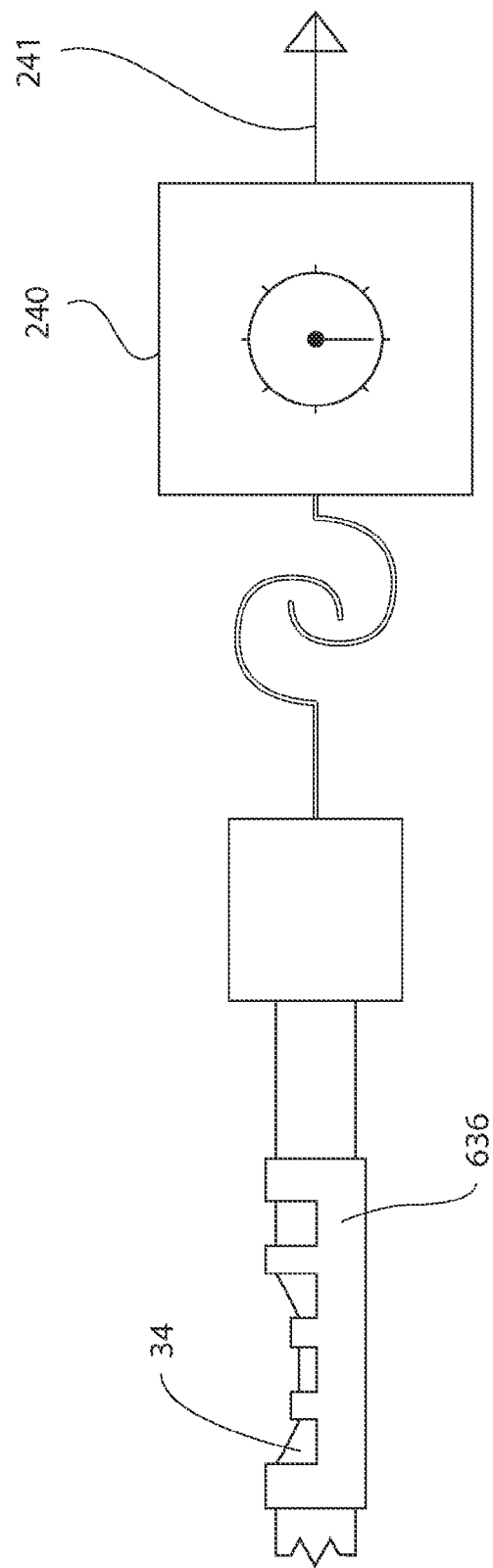

In a variation of a crimping method includes crimping discrete, preprepared portions of an embryonic lock so that the resulting friction force upon movement of the resulting lock and the filament may be controlled. In an exemplary method, an embryonic lock 636 is prepared with slots 637 cut into the embryonic lock 636 as is exemplary depicted in FIG. 26A. Then, one or more of the resulting arches 638 is crimped or otherwise compressed, one, two, three, four, etc., at a time. For example, in a method that includes crimping/compressing one arch at a time, after a first crimping/compressing operation, the embryonic lock 636 takes on the form as shown in FIG. 26B. Next, a second arch is crimped/compressed, resulting in an embryonic lock 636 taking on the form as shown in FIG. 26C. As each arch 638 is crimped or compressed, the friction force between the resulting lock and the filament 34 is increased. As with some other embodiments detailed herein, the filament 34 is linked to a force gage as shown in FIG. 27A. A force is applied to the force gage 240 and thus the filament 34 in the direction of the horizontal arrow while the arches of the embryonic lock 636 are compressed. Increasing the number of arches crimped/compressed increases the friction force between the filament 34 and the resulting lock. Thus, by gradually increasing the number of arches crimped/compressed, the friction force is also gradually increased, as may be seen by comparing FIG. 27A to FIG. 27B. As may be seen, the force gage 240 registers a higher force in FIG. 27B because more arches have been crimped/compressed in the embryonic lock 636. By testing/measuring the friction force as the arches are compressed (either continuously or in a compress/test/compress/test regime) for various arch compressions and halting further crimping upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the depth of crimping/compression of the arches may be controlled. By measuring the resulting force for various depths in an analogous manner as detailed above with respect to FIGS. 22A and 22B, quality control can be further enhanced.

Figure 28:
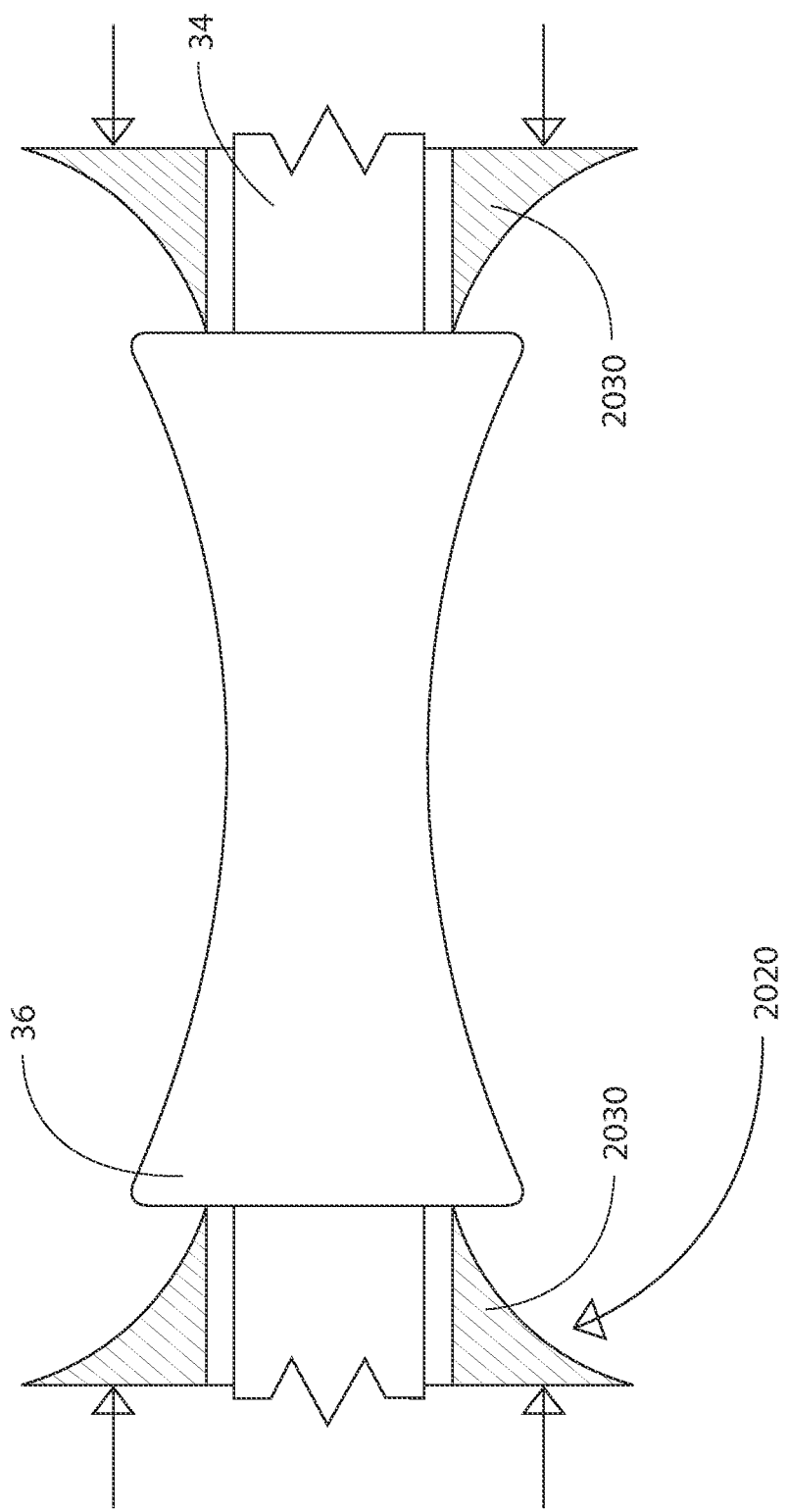
FIGS. 28-29B depict another exemplary embodiment in which the lock is deformed whereby the requisite friction force between the lock and the filament is controlled.
Figure 29A:
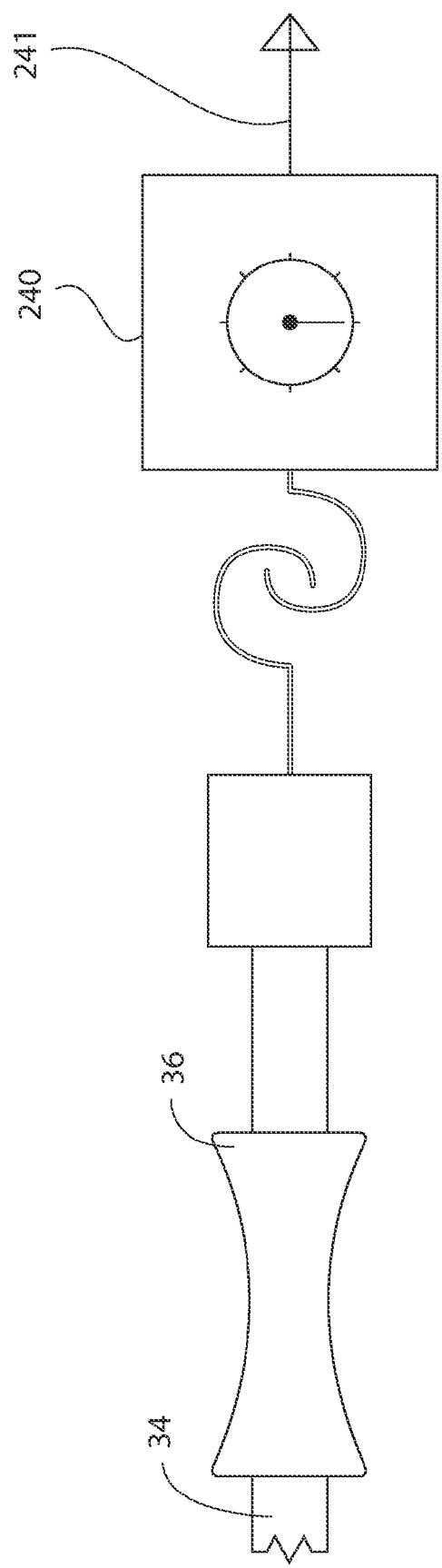
Figure 29B:
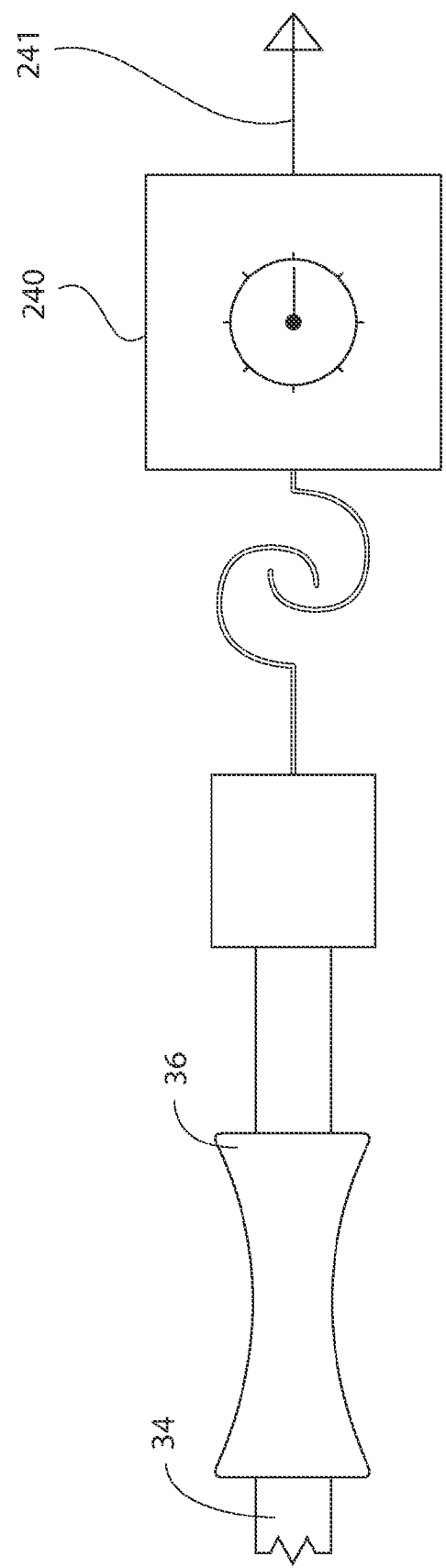

Another embodiment of the present invention includes a method and a device for unduing a crimping operation. As may be seen in FIG. 28, a decrimping device 2020 includes jaws 2030 that fit around filament 34. The jaws are driven towards each other (or in embodiments where jaws 2030 are only located on one side of the lock 36, the jaws 2030 are driven towards a reaction plate or the like. The jaws decrimp, at least partially, the crimp applied to the lock 36. This has the effect of reducing the friction force that must be overcome to move the lock 36 relative to the filament 34 as the crimp on the lock 36 is undone. In an exemplary method, the filament 34 is linked to a force gage as shown in FIG. 29A during the decrimping operation. A force is applied to the force gage 240 and thus the filament 34 in the direction of the horizontal arrow while the lock 36 is decrimped with variable decrimping (i.e., the amount that the jaws 2030 are driven towards each other is varied). Increasing the amount that the jaws 2030 are driven towards each other increases the bore diameter of the lock 36 and thus decreases the friction force required to be overcome to move the filament 34 relative to the resulting lock 36. Thus, by gradually increasing the depth that the jaws 2030 are inserted during the decrimping process the friction force is also gradually decreased, as may be seen by comparing FIG. 29A to FIG. 29B. As may be seen, the force gage 240 registers a lower force in FIG. 29B because the jaws 2030 have been driven further towards each other than in FIG. 29A, thereby increasing the bore diameter of the lock 36 relative to that of FIG. 29A. By testing/measuring the friction force as the jaws 2030 are driven towards each other (either continuously or in a decrimp/test/decrimp/test regime) for various depths and halting further driving upon a determination that the friction force has fallen with in an acceptable range, a consistent requisite friction force may be created for each closure device 20, ensuring quality control if this method is executed for each closure device 20. This alleviates tolerancing issues because the testing is performed on each individual component.

It is noted that the method just described may be used to rehabilitate a lock that was crimped too much (i.e., bring it back into specifications) and/or as a standard part of the process of manufacturing the closure device 20. That is, it could be standard procedure to "over crimp" the lock 36 and then decrimp the lock so that the friction force falls within the desired range. It is further noted that the decrimping device 2020 may be combined with the crimping device detailed above with respect to FIG. 22 for manufacturing efficiency purposes.

Figure 30A:
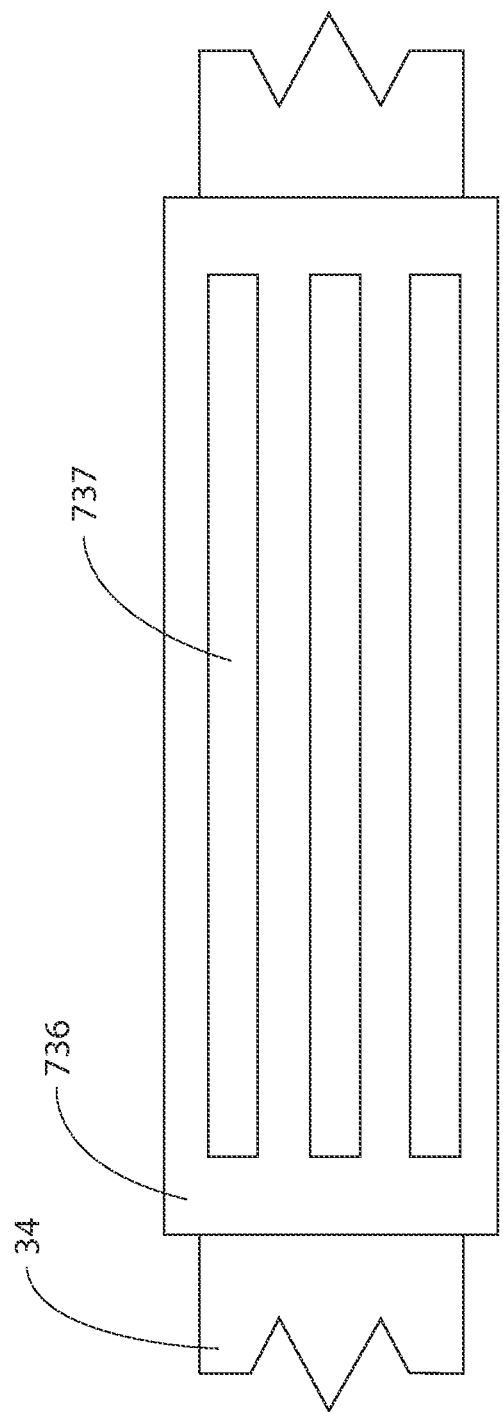
FIGS. 30A-30B depict another exemplary embodiment in which the lock is twisted whereby the requisite friction force between the lock and the filament is controlled.
Figure 30B:
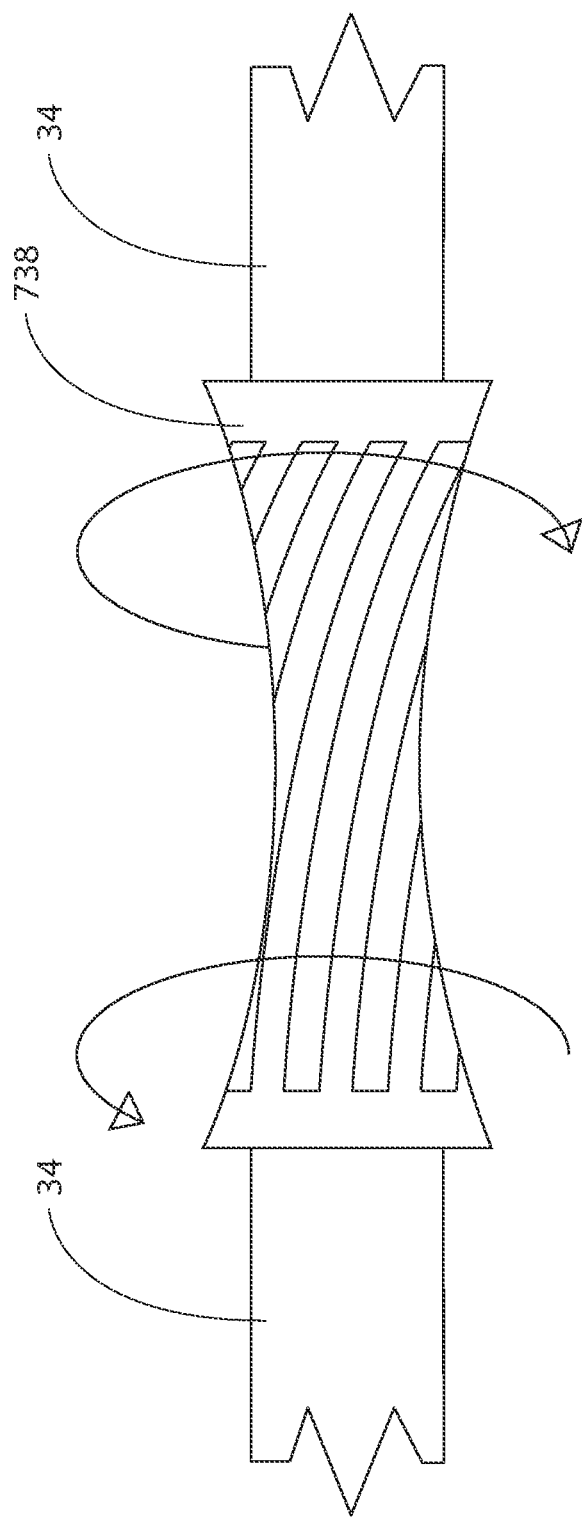

An alternate embodiment includes twisting an embryonic lock to reduce the interior bore diameter so that the resulting friction force required to be overcome to move the resulting lock relative to the filament may be controllably increased. In an exemplary method, an embryonic lock 736 is prepared with slots 737 cut into the embryonic lock 736 as is exemplary depicted in FIG. 30A. Then, the embryonic lock 736 is twisted to reduce the interior diameter, thereby compressing the filament 34, as may be seen in FIG. 30B. As with some other embodiments detailed herein, the filament 34 may be linked to a force gage. A force is applied to the force gage as detailed herein while the embryonic lock 736 is twisted. Increasing the twist angle of the embryonic lock 736 increases the friction force between the filament 34 and the resulting lock. Thus, by gradually increasing the twist angle, the friction force is also gradually increased. As will be understood, the force gage will register a higher force the more that the embryonic lock 736 is twisted. By testing/measuring the friction force as the embryonic lock 736 is twisted (either continuously or in a twist/test/twist/test regime) and halting further twisting upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the embryonic lock 736 may be over twisted and then detwisted to arrive at the desired friction force. Thus, this embodiment is analogous to that detailed above with respect to the decrimping device. It is noted that in some embodiments, the embryonic lock 736 will be twisted 20 degrees, then the friction force will be tested, followed by an another 20 degrees of twisting, etc. This process will be repeated until the friction force that must be overcome to move the components relative to one another falls within a range of about 0.4 to 0.6 pounds.

In an embodiment, the lock 736 may be twisted such that the interior diameter of the lock 736 is reduced from 0.015 inches to 0.013 inches to result in one pound of force being required to overcome the friction force between the filament and the lock. Further, the interior diameter of the lock 736 may be reduced to 0.012 inches to result in five pounds of force being required to overcome the friction force between the filament and the lock.

Figure 31A:
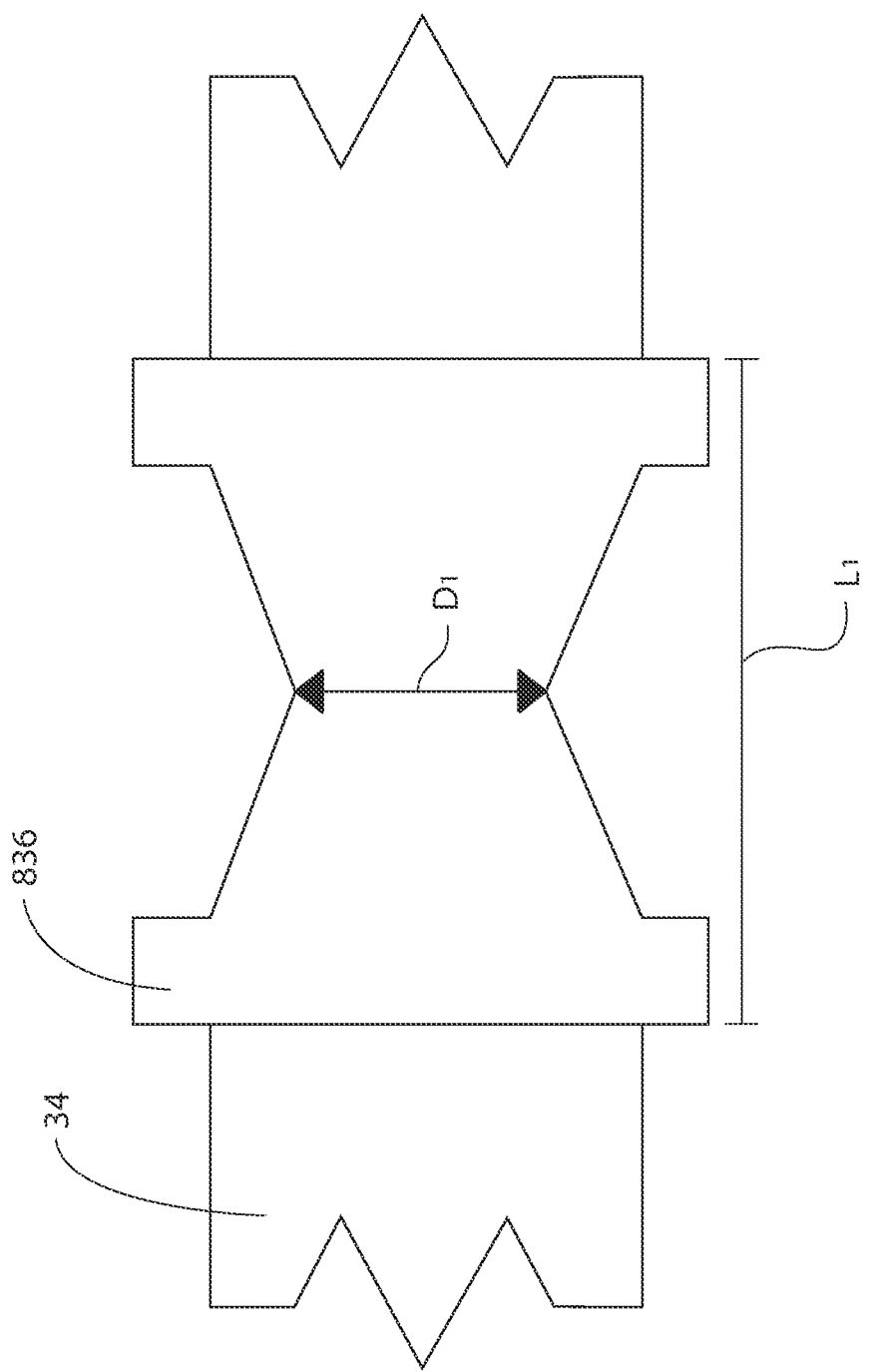
FIGS. 31A-31B depict another exemplary embodiment in which the lock is compressed whereby the requisite friction force between the lock and the filament is controlled.
Figure 31B:
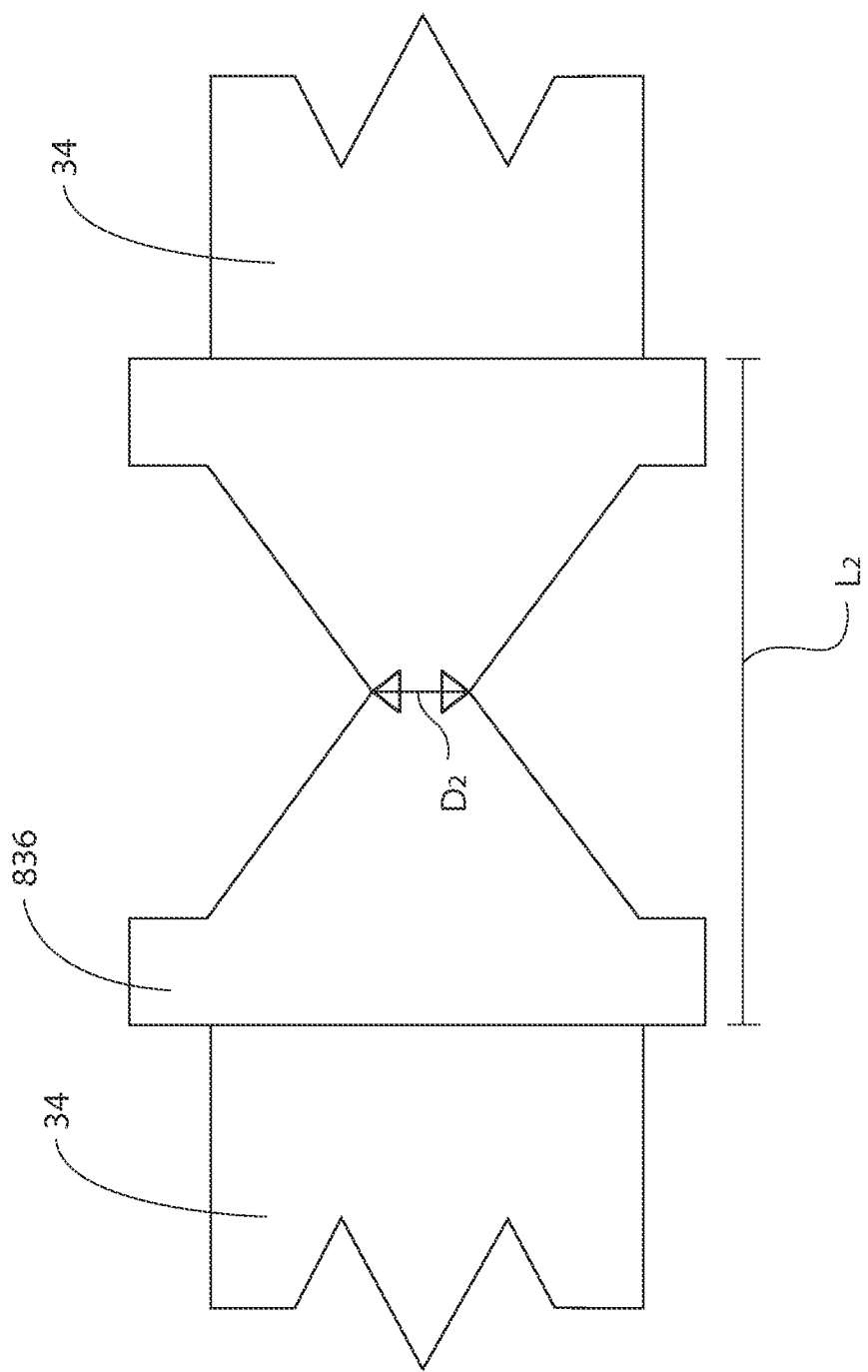

Yet another alternate embodiment includes compressing an embryonic lock in the longitudinal direction to reduce the interior bore diameter so that the resulting friction force upon movement of the resulting lock and the filament may controllably increased. In an exemplary method, an embryonic lock 836 as may be seen in FIGS. 31A and 31B having a configuration that lends itself to relatively easy longitudinal compression coupled with a corresponding reduction in the interior diameter of the bore is compressed from a length L1 (where the embryonic lock 836 has an interior bore diameter of D1) ultimately to a length L2, which is less than L1 (where the embryonic lock 836 has an interior bore diameter of D2, which is less than D1). As with some other embodiments detailed herein, the filament 34 may be linked to a force gage. A force is applied to the force gage as detailed herein while the embryonic lock 836 is compressed. Increasing the compression of the embryonic lock 836 increases the friction force between the filament 34 and the resulting lock because the interior bore diameter is reduced.

Thus, by gradually compressing the embryonic lock, the friction force is also gradually increased. As will be understood, the force gage will register a higher force the more that the embryonic lock 836 is compressed. By testing/measuring the friction force as the embryonic lock 836 is compressed (either continuously or in a compress/test/compress/test regime) and halting further compression upon a determination that the friction force has fallen with in an acceptable range, a consistent requisite friction force may be created for each closure device 20, ensuring quality control if this method is executed for each closure device 20. This alleviates tolerancing issues because the testing is performed on each individual component. It is noted in other embodiments, the embryonic lock 836 may be over compressed and then decompressed to arrive at the desired friction force. Thus, this embodiment is analogous to that detailed above with respect to the decrimping device.

It is noted that in some embodiments, the locks disclosed herein may be made of titanium or a titanium alloy, iron or an iron alloy (e.g., an iron-magnesium alloy), stainless steel 302, 307, 316 and 316L or other types of stainless steel, a cobalt chromium alloy, PLLA/PLG, or any other material that provides acceptable results when configured as a lock as detailed herein.

Figure 32A:
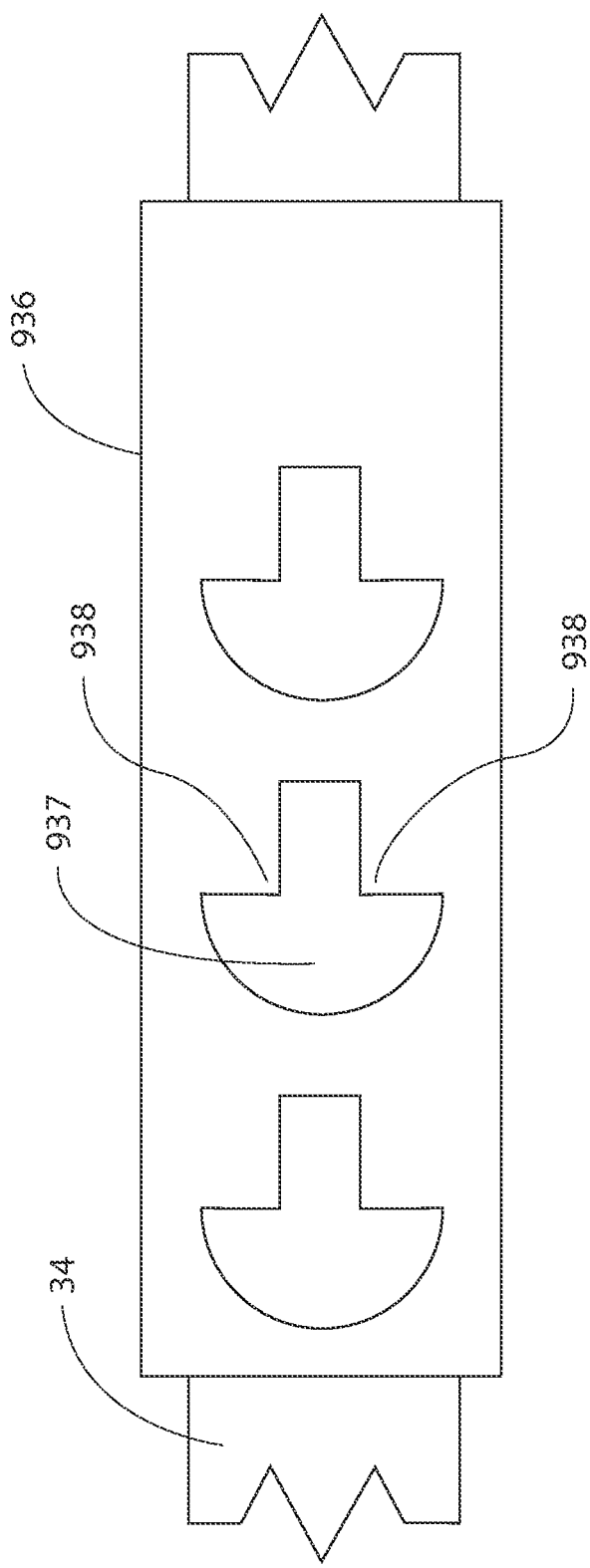
FIGS. 32A-33 depict another exemplary embodiment in which the lock is deformed whereby the requisite friction force between the lock and the filament is controlled.
Figure 32B:
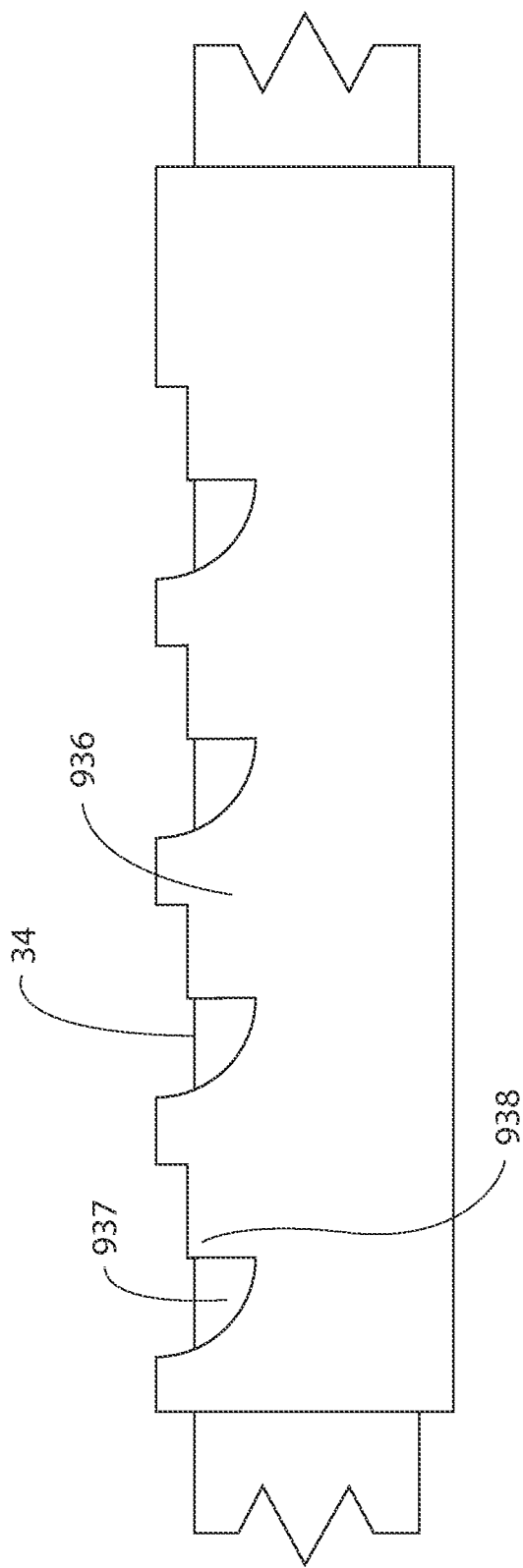
Figure 33:
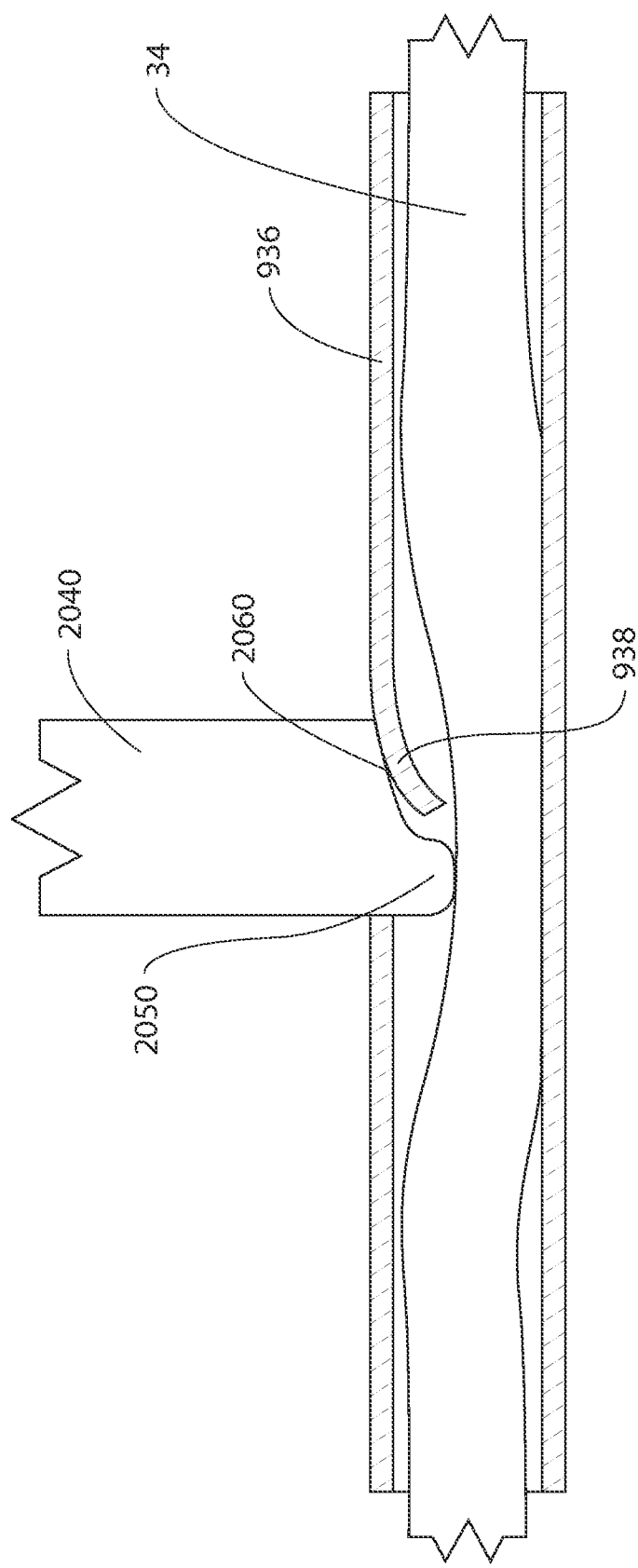

Another variation of a crimping method includes crimping discrete, preprepared portions of an embryonic lock so that the resulting friction force required to move the resulting lock relative to the filament may be controlled. In an exemplary method, an embryonic lock 936 is prepared with holes 937 cut (e.g., laser cut) into the embryonic lock 936 as is exemplary depicted in FIGS. 32A and 32B (FIG. 32B being a side-view of FIG. 32A). Then, the corners 938 of one or more of the resulting holes 937 are crimped or otherwise compressed, one, two, three, four, etc., at a time using a crimping mandrel 2040 as seen in FIG. 33. FIG. 33 depicts a crimping mandrel 2040 including a head 2050 and a wedge 2060. The lateral dimensions of the crimping mandrel 2040 are configured such that the area around the head 2050 slidably fits into the hole 937 such that the hole 937 aligns the crimping mandrel 2040 (more particularly, the semicircle section aligns the crimping mandrel 2040). Driving the crimping mandrel 2040 into the hole 937 causes the wedge 2060 to crimp down the corners 938 as may be seen in FIG. 33.

In a method that includes crimping/compressing the corners 938 of one hole 936 one at a time, after a first set of corners 938 are crimped, if necessary a second set of corners are crimped, followed by a third, etc., as necessary. As each set of corners 938 is crimped, the requisite friction force required to be overcome to move the resulting lock relative to the filament 34 is increased. As with some other embodiments detailed herein, the filament 34 is linked to a force gage. A force is applied to the force gage 240 and thus the filament 34 while the sets of corners of the embryonic lock 636 are crimped. Increasing the number of corners crimped increases the friction force between the filament 34 and the resulting lock. Thus, by gradually increasing the number of corners compressed, the friction force is also gradually increased. By testing/measuring the friction force as the corners are crimped (either continuously or in a crimp/test/crimp/test regime) for various crimping actions and halting further crimping upon a determination that the friction force has fallen with in an acceptable range, a consistent friction force may be created for each closure device 20, ensuring quality control if this method is executed for each closure device 20. This alleviates tolerancing issues because the testing is performed on each individual component.

Further, an embodiment of the method just detailed includes fully bottoming out the head 2050 of the crimping mandrel 2040 on the filament 34 (i.e., driving the crimping mandrel 2040 downward onto the filament 34 until the filament 34 is substantially fully compressed) during each crimping action. By properly dimensioning the crimping mandrel 2040, tolerancing of the filament and/or the embryonic lock can be discounted, at least with respect to a braided filament 34. That is, if the head 2050 substantially fully compresses the filament, the amount that the corners 938 will be crimped relative to the filament will correspond to a sufficient amount of crimping of the corners to establish a requisite friction force for each individual closure device without testing. That is, in some exemplary embodiments, by bottoming out the head of the crimping mandrel 2040, the depth of crimping is controlled because the amount that the filament 34 can be ultimately compressed relative to the crimping should be about the same regardless of tolerancing of the filament 34 and/or the embryonic lock. Also, in some embodiments, the "D" shape allow the head to have sufficient strength and, as noted above, permits guiding/alignment of the crimping mandrel 2040 with the embryonic lock 936. In some exemplary embodiments using such a method, the crimping mandrel 2040 can be calibrated to establish various requisite friction forces by varying the head to wedge distance and/or varying the angle of the wedge of the mandrel 2040.

It is noted in other embodiments, the depth of crimping of the corners may be controlled. By measuring the resulting force for various depths in an analogous manner as detailed above with respect to FIGS. 22A and 22B, quality control can be further enhanced.

Figure 34:
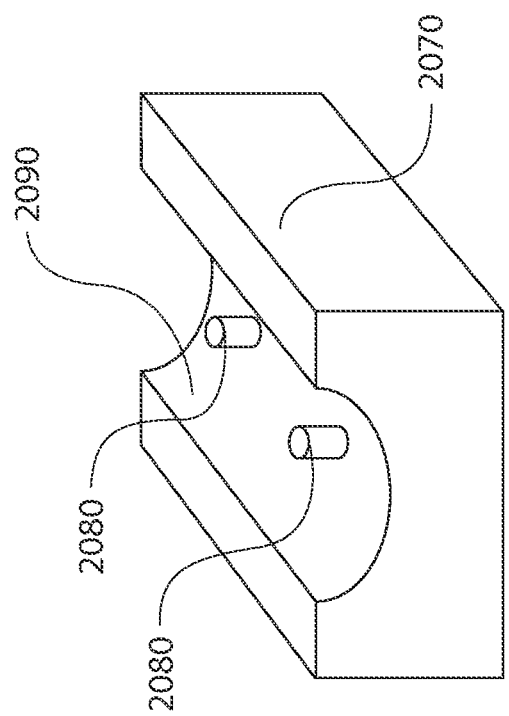
FIG. 34 depict a fixture used during crimping of some exemplary locks.
Figure 35:
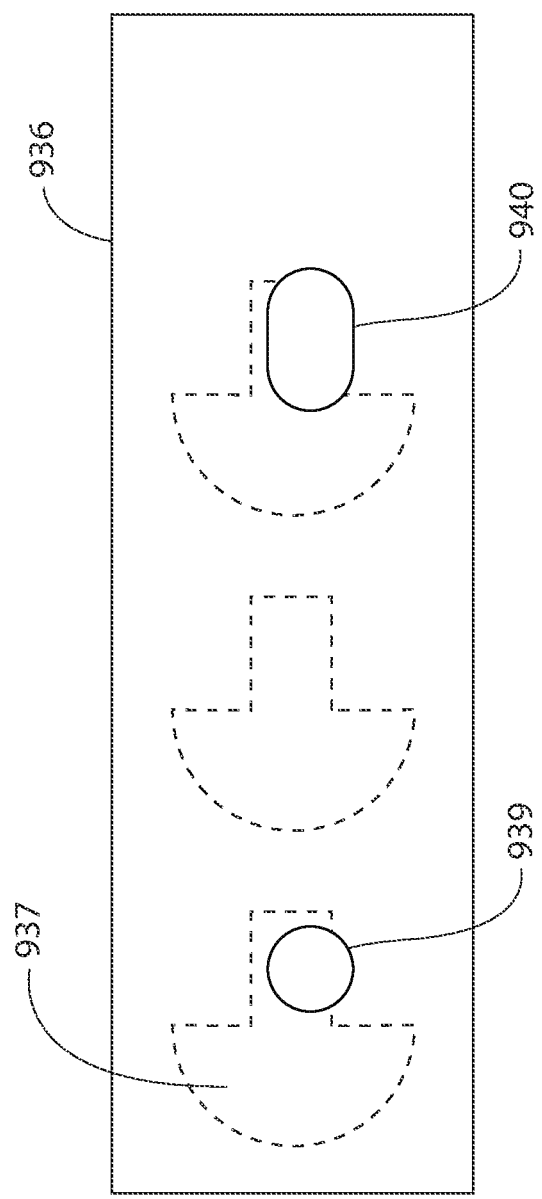
FIG. 35 depicts a lock that interfaces with the fixture of FIG. 34.

FIG. 34 depicts a holding fixture 2070 that may be used to hold the embryonic lock 936 in place during crimping. However, in other embodiments, the fixture 207 may be used with other embryonic locks. As may be seen in FIG. 34, the fixture 2070 includes two studs 2080 that protrude from the curved surface 2090 of the fixture 2070. These studs 2080 fit into corresponding holes in the embryonic lock 936 (or other embryonic lock as detailed herein and variations thereof) as depicted in FIG. 35. Specifically, opposite the holes 937, holes 939 and 940 are positioned in the embryonic lock 936. Hole 939 is a circular hole while hole 940 is a slotted hole to relieve the tolerancing in the longitudinal direction. Any size and/or shape hole may be used providing that the embryonic lock 936 is held in place. Alternatively, the holes in the embryonic lock 936 may be circular and one of the studs 2080 may be a square or rectangle pin or the like.

Figure 36:
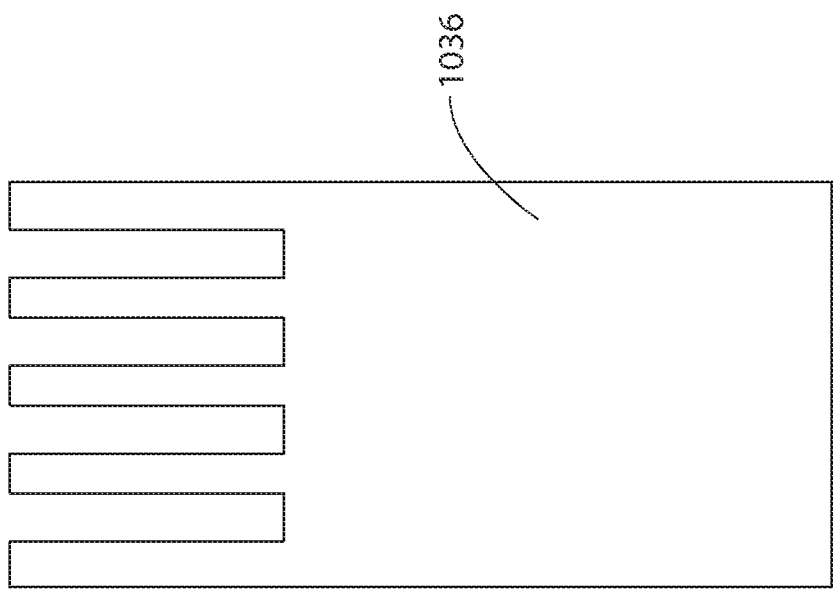
FIG. 36-37 depict alternate embodiments of a lock.

With respect to the embodiment depicted above with respect to FIG. 16A, it is noted that the end portions of the embryonic lock 3360 need not be pointed. That is, in some embodiments, the ends may be blunt (flat). Along these lines, FIG. 36 depicts an alternate embodiment of an embryonic lock 1036. Embryonic lock 1036 may be substituted for embryonic lock 3360 referenced herein in FIGS. 16A and 16B and 16C.

Figure 37:
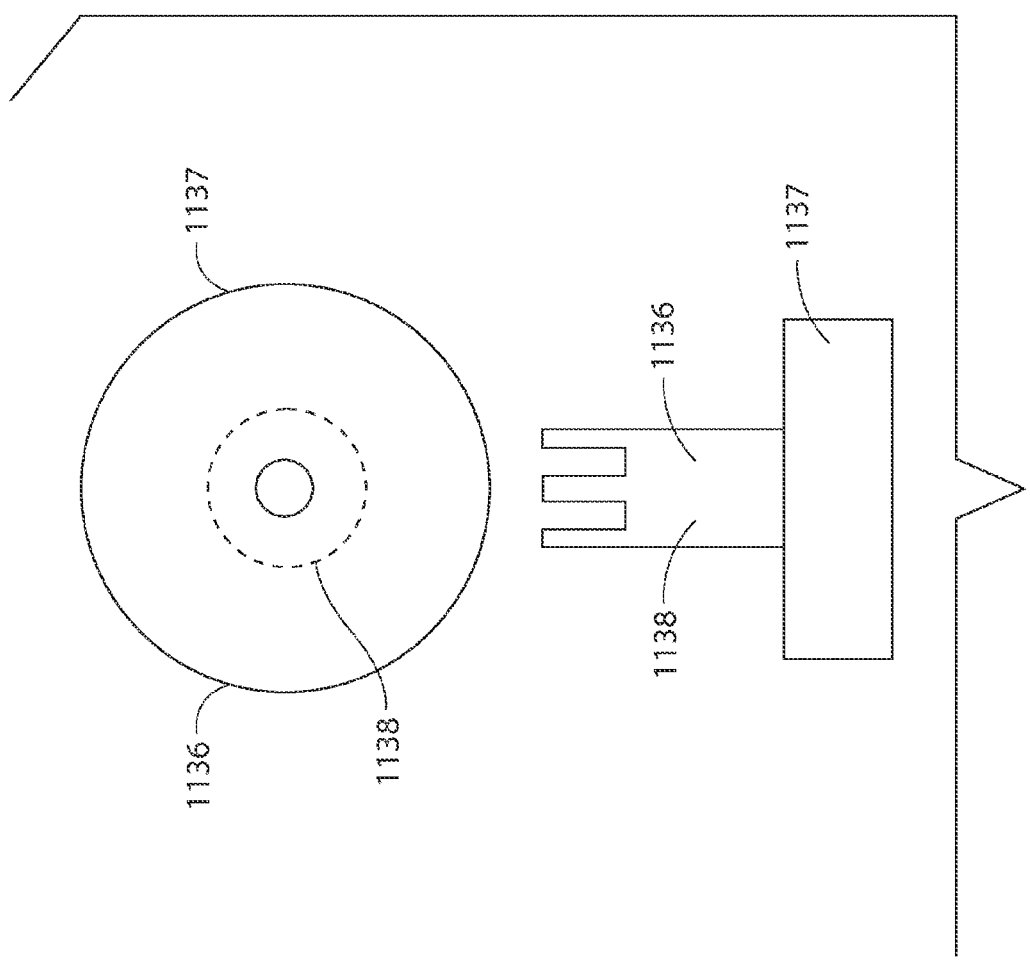
Figure 38:
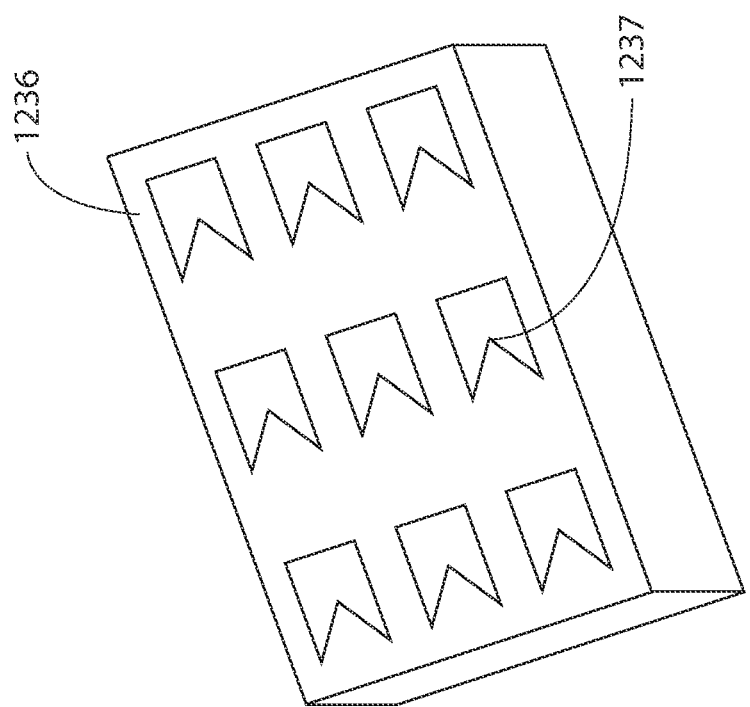
FIGS. 38-42 depict exemplary embodiments of embryonic locks.

FIG. 37 depicts an alternate embodiment of an embryonic lock 1136 with a protruding side 1137. In an exemplary embodiment, the protruding side 1137 is in the form of a cylinder that extends from the main body 1138 of the embryonic lock 1136.

FIGS. 38-42 depict an alternate embryonic lock that may be used in some embodiments of the present invention. As may be seen from these figures, initially, the embryonic lock 1236 is in the form of a rectangular plate including pointed tabs 1237 etched therein. In other embodiments, the pointed tabs 1237 may be stamped therein or the embryonic lock 1236 may be formed through lithography to include the pointed taps 1237. The embryonic lock 1236 depicted in FIG. 38. may be 2 mm by 2 mm square.

Figure 39:
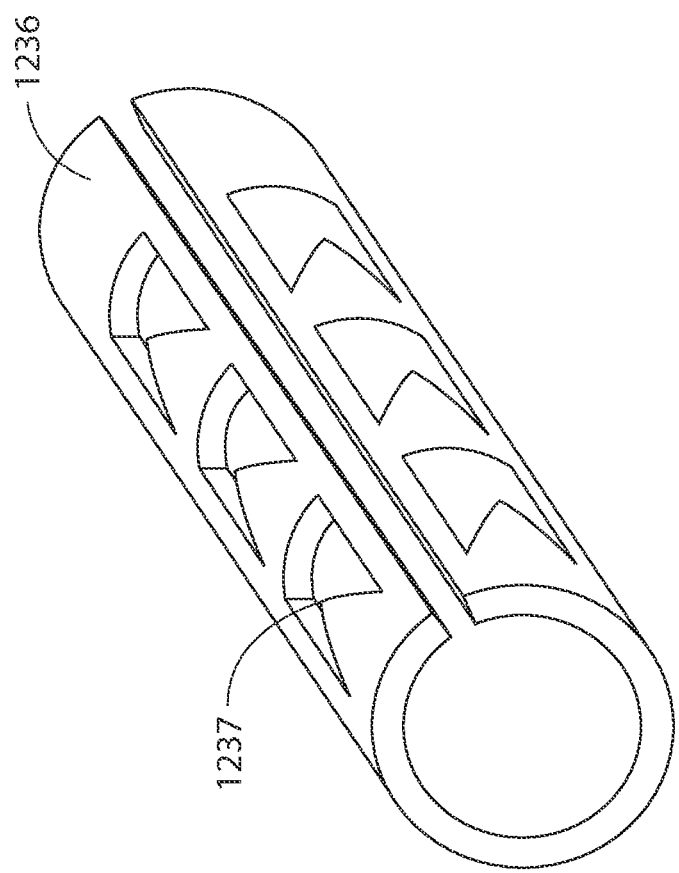
Figure 40:
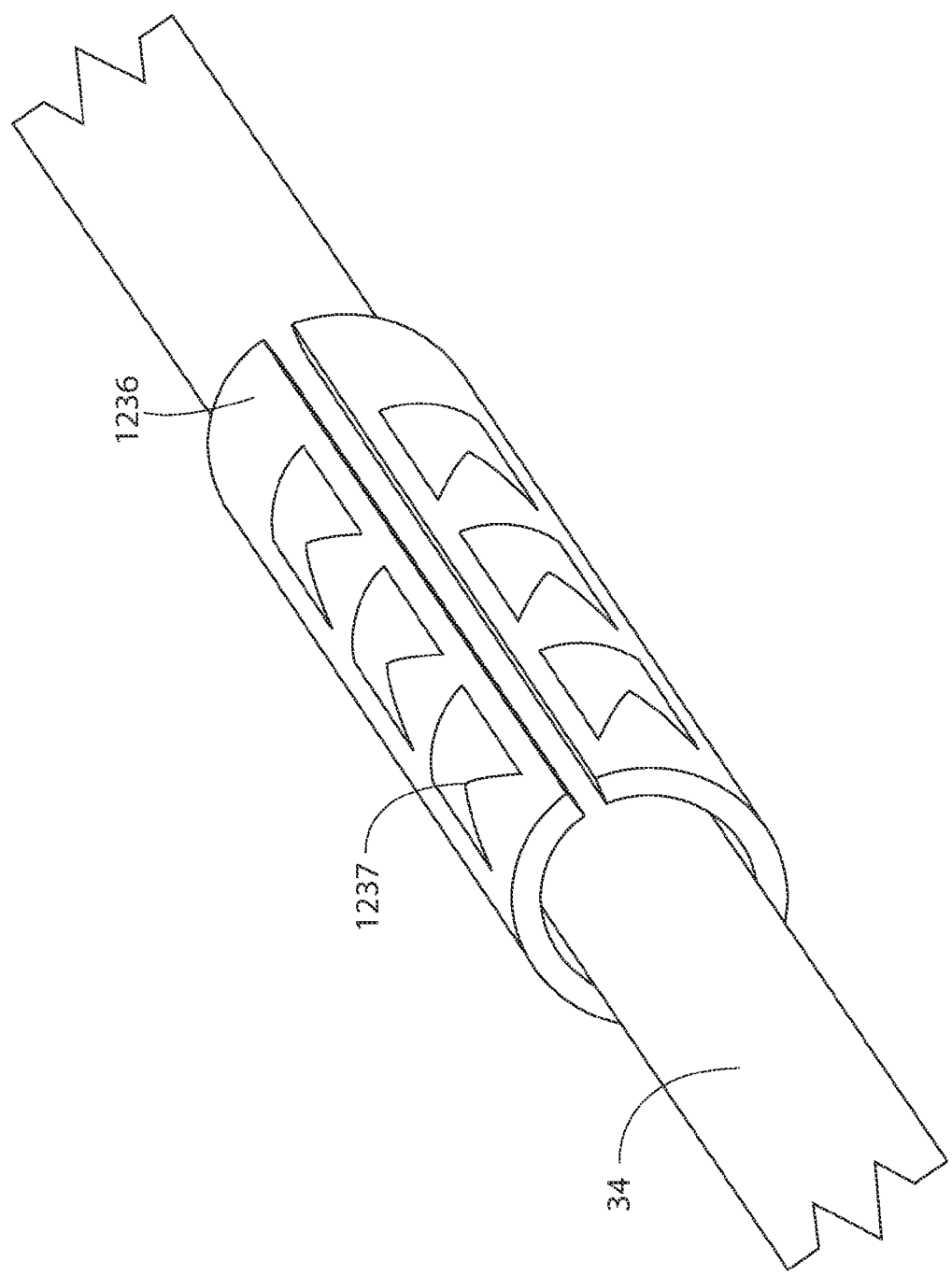
Figure 41:
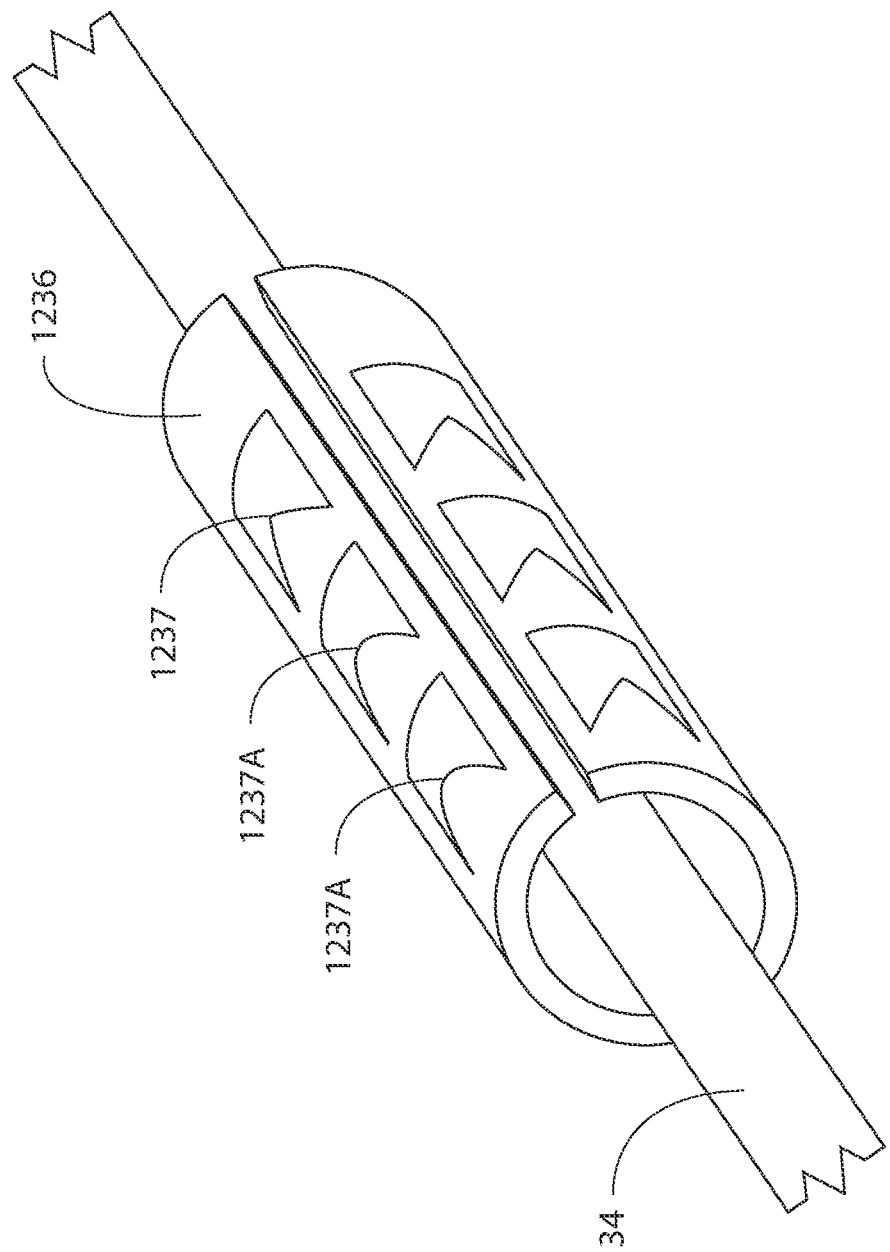
Figure 42:
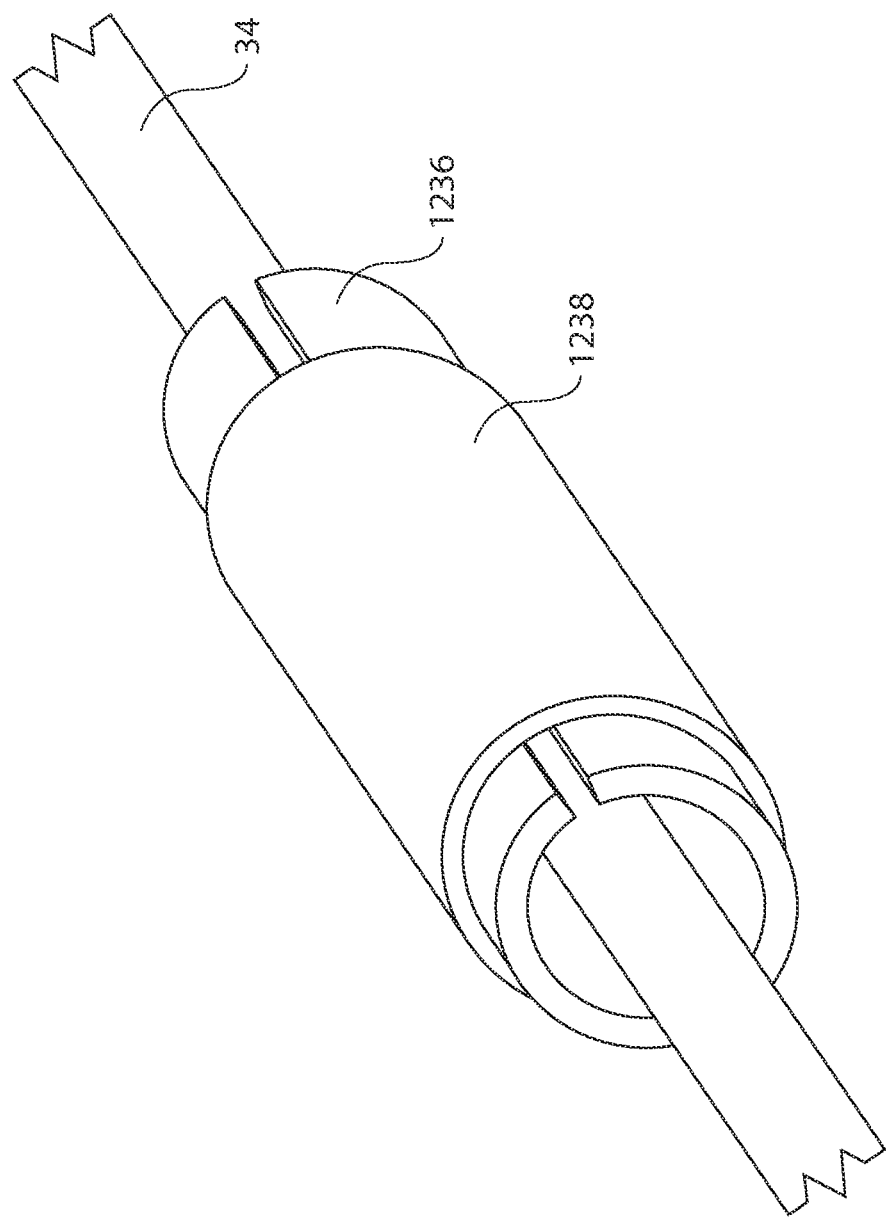

Next, the embryonic lock 1236 is rolled into the configuration seen in FIG. 39, after which a filament 34 is threaded through the resulting bore of the embryonic lock 1236 as depicted in FIG. 40. After this threading step, the embryonic lock 1236 is "armed" by bending/crimping at lest some of the pointed tabs 1237 inward, resulting in armed pointed tabs 1237A, as may be seen in FIG. 41. This arming step may be controlled to vary the resulting friction force between the resulting lock and the filament 34 as detailed above with respect to, for example, FIGS. 26A-26C. After the arming step, a cover 1238 may be placed around the rolled embryonic lock 1236 to maintain the rolled configuration of the embryonic lock 1236. This cover 1238 may be a stainless steel cylinder that creates an interference fit with the rolled embryonic lock 1236.

It is noted that the pointed tabs 1237 may instead be bent before the rolling step. Thus, the rolling step may be controlled to vary the resulting friction force between the resulting lock and the filament 34 in a manner analogous to that detailed above.

Figure 43:
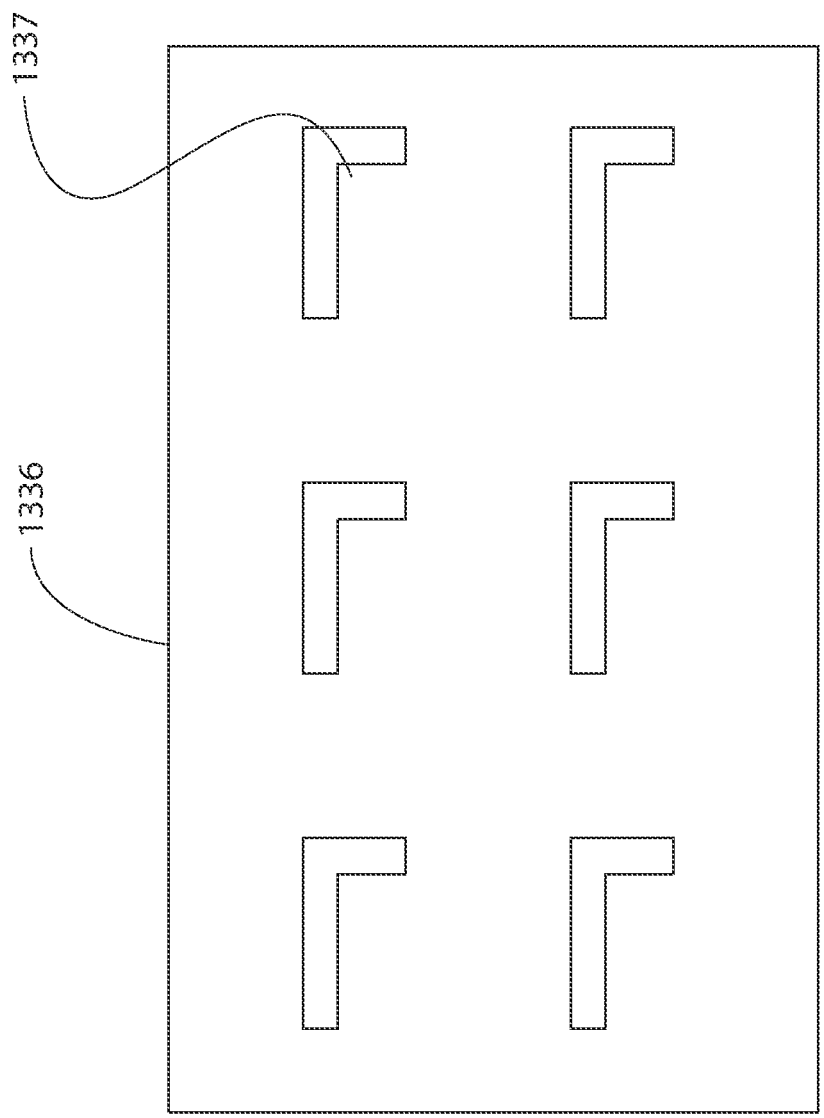
FIGS. 43-47 depict additional exemplary embodiments of embryonic locks.

FIG. 43 depicts an alternate embryonic lock 1336 that substantially parallels that of 1236 except that the pointed tabs 1337 have the configuration seen in the figure.

Figure 44:
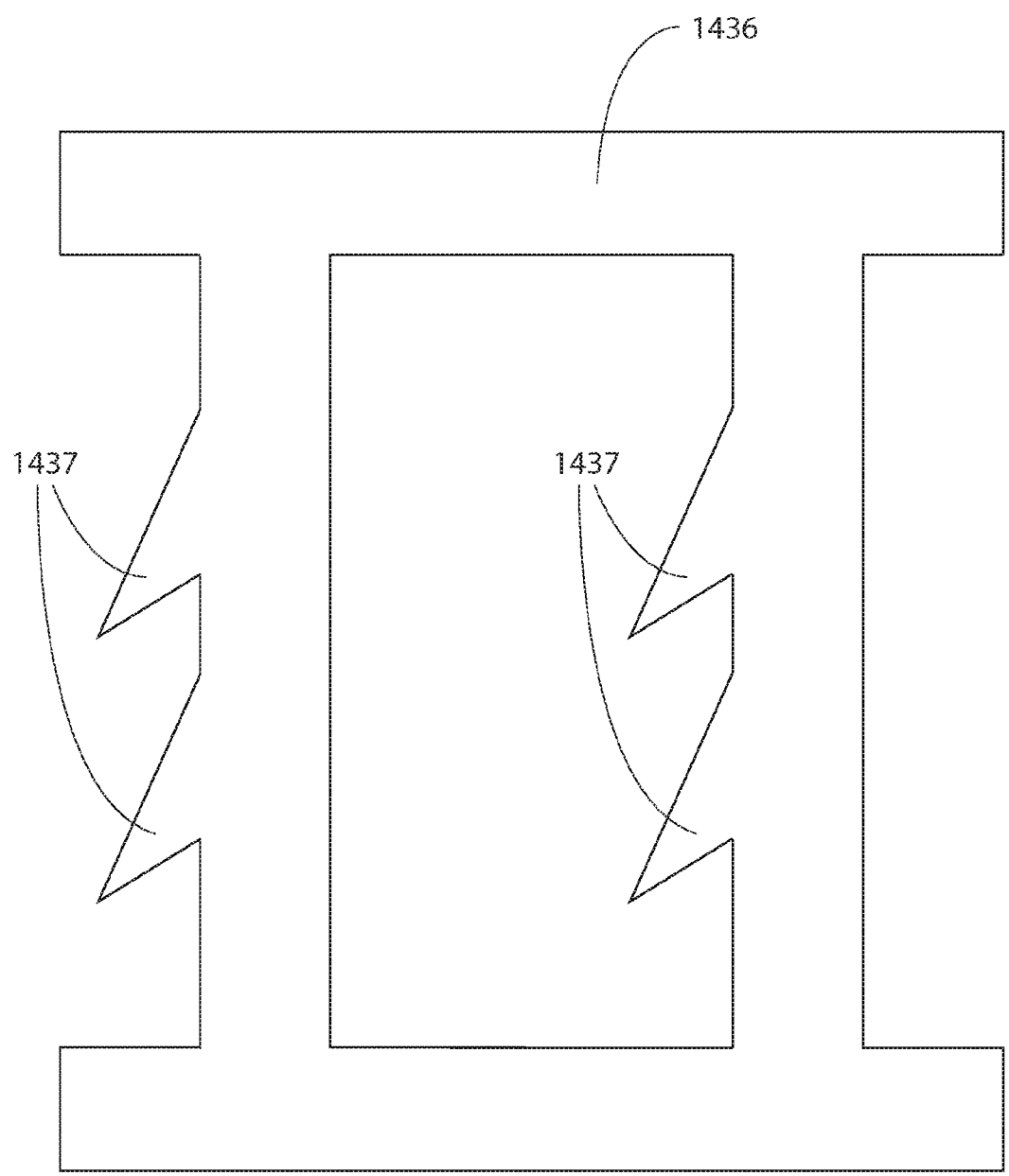

FIG. 44 depicts yet another alternate embryonic lock 1436 that may be incorporated into the closure device 20 detailed herein. As may be seen from FIG. 44, initially, the embryonic lock 1436 is in the form of a plate including one or more pointed tabs 1437 etched therein. In other embodiments, the embryonic lock 1436 may be formed with the tabs 1437 through stamping or through lithography. The embryonic lock 1436 may be incorporated into the closure device as detailed above with respect to the embryonic lock 1236.

Figure 45:
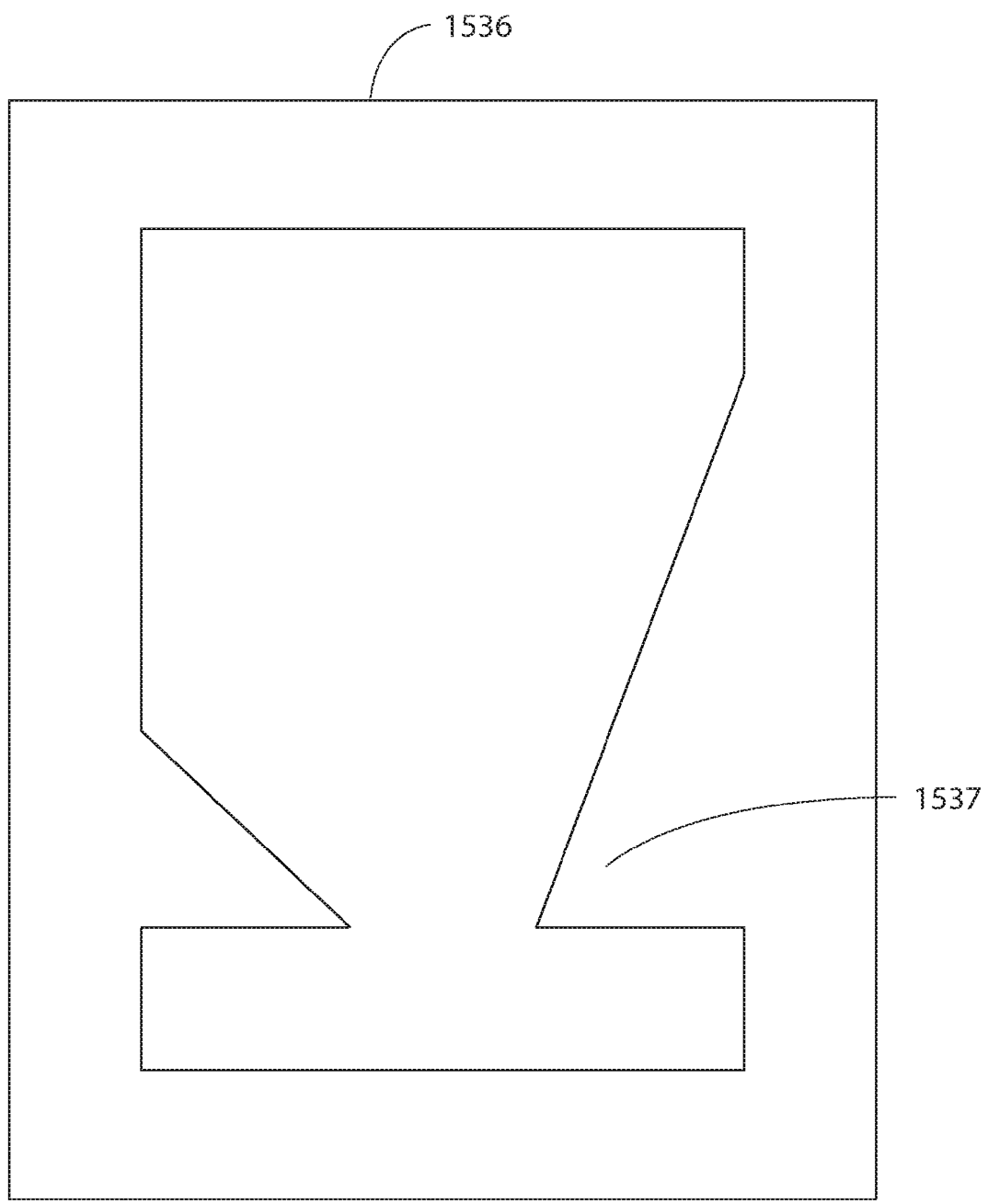

FIG. 45 depicts yet another alternate embryonic lock 1536 that may be incorporated into the closure device 20 detailed herein. As may be seen from FIG. 45, initially, the embryonic lock 1536 is in the form of a plate including one or more pointed tabs 1537 etched therein. In other embodiments, the embryonic lock 1536 may be formed with the tabs 1537 through stamping or through lithography. The embryonic lock 1536 may be incorporated into the closure device as detailed above with respect to the embryonic lock 1236.

In some embodiments, the plates of the embryonic locks presented herein with respect to FIGS. 38-45 may be 2 mm by 3 mm or 3 mm by 3 mm with a thickness of 2-5 mils. When rolled, the interior diameter (bore diameter) may be about 20-30 mils, and the outer diameter may be about 30-40 mils.

Figure 46:
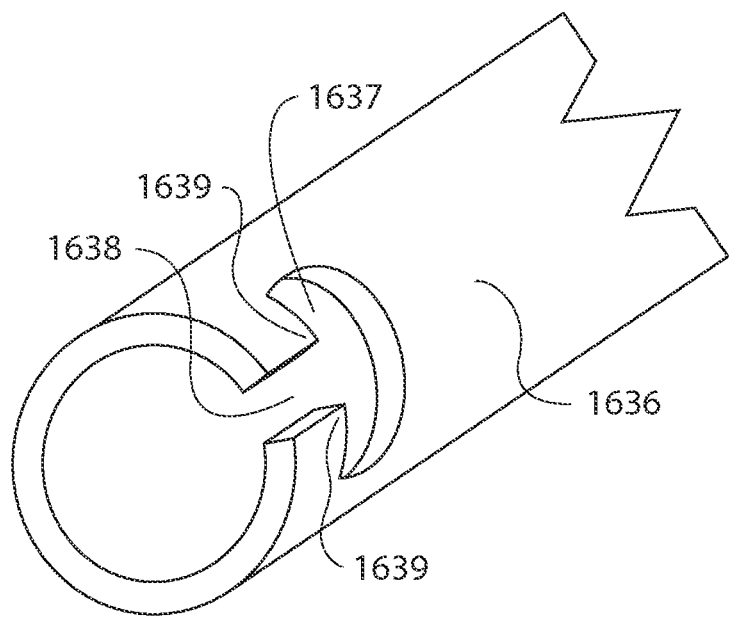
Figure 47:
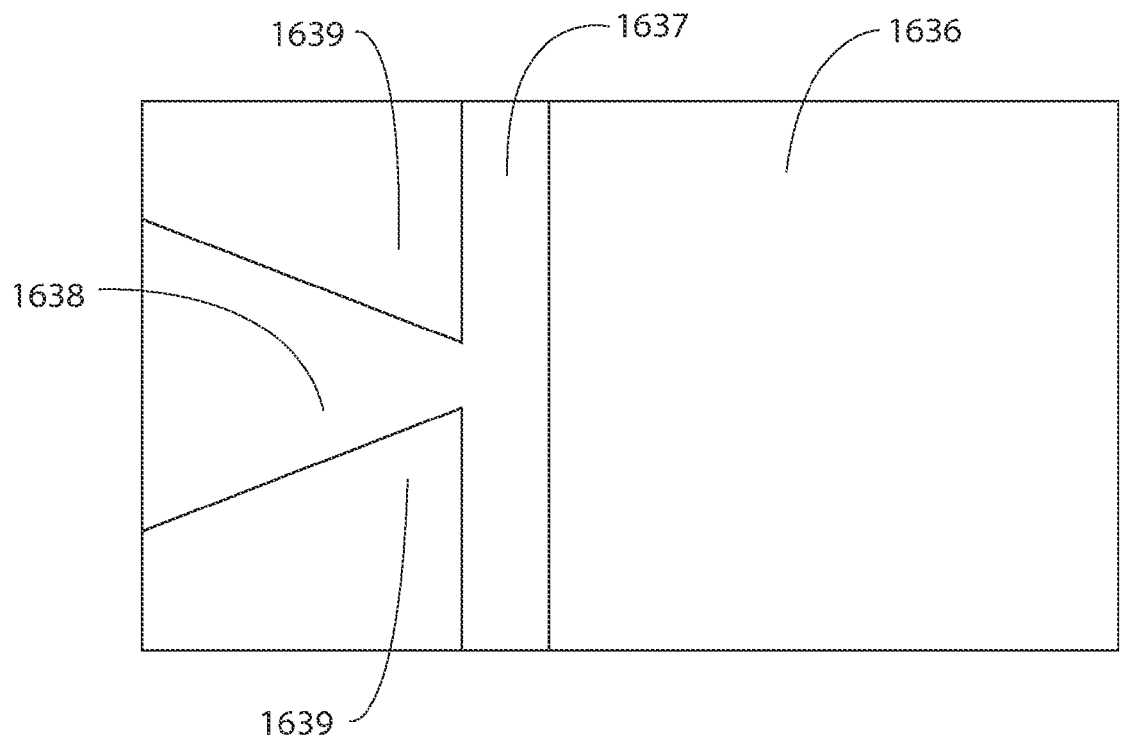
Figure 48:
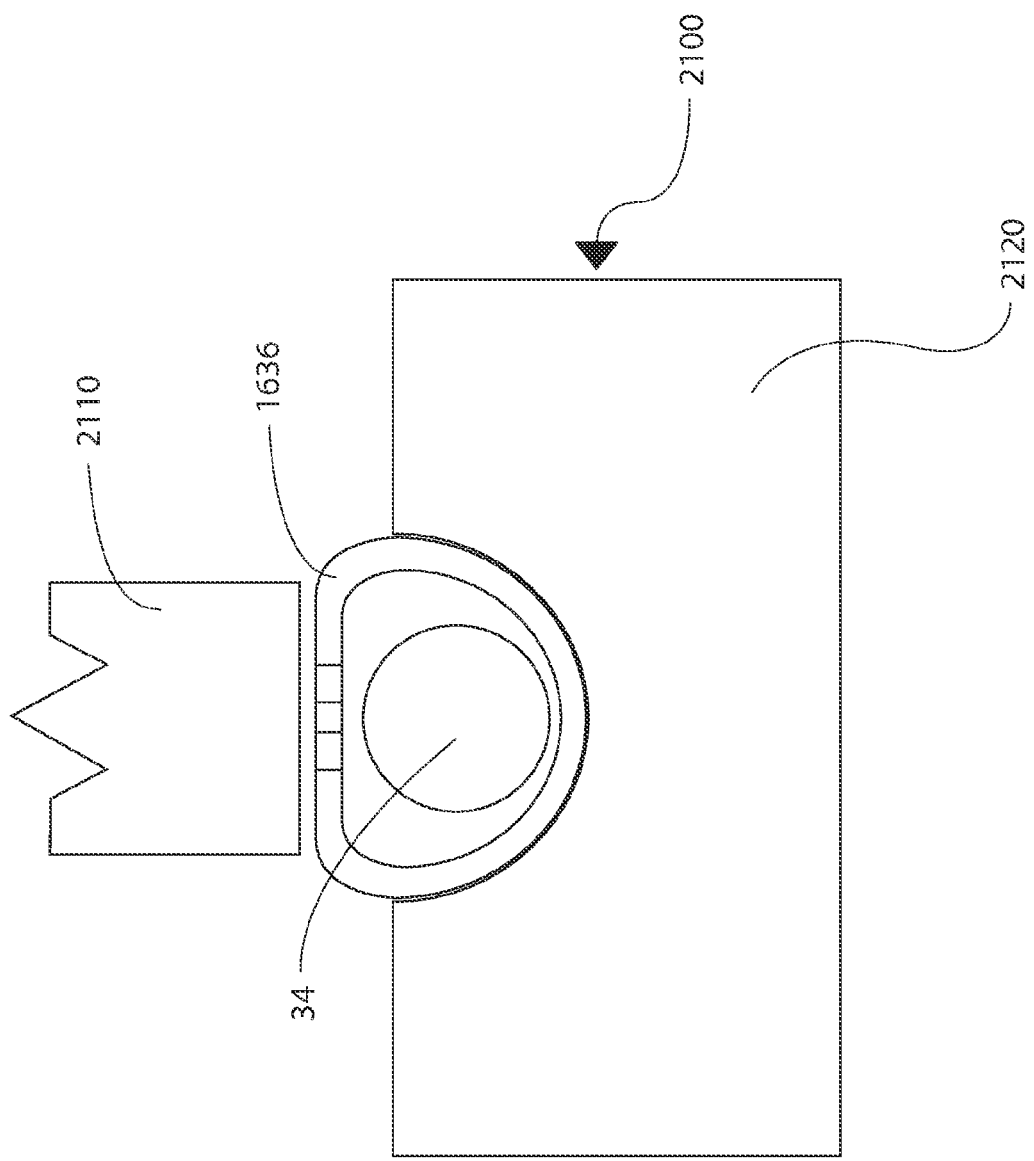
FIG. 48 depicts an exemplary embodiment in which the lock is deformed whereby the requisite friction force between the lock and the filament is controlled.
Figure 49:
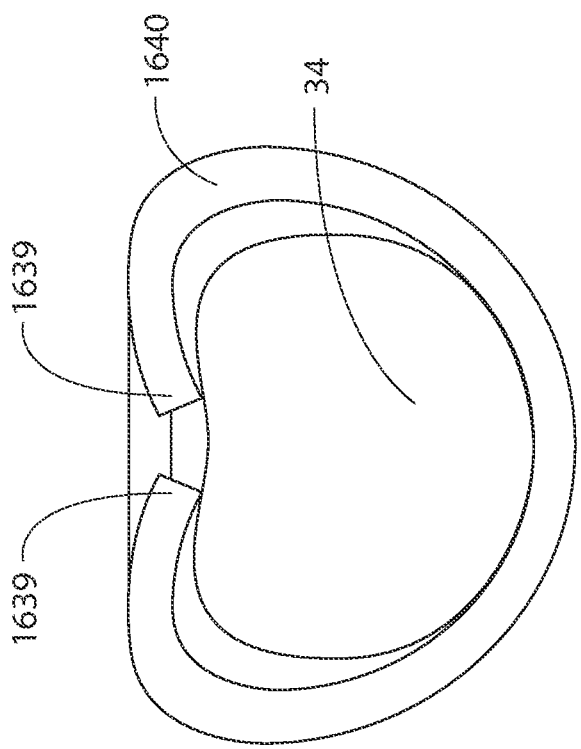
FIGS. 49-52 depict additional exemplary embodiments of a lock.

FIGS. 46 and 47 depict yet another alternate embryonic lock 1636 that may be incorporated into the closure device 20 detailed herein. As may be seen from FIGS. 46 and 47 (FIG. 47 being a top view of the embryonic lock 1636), initially, the embryonic lock 1636 has the form depicted in these figures. A slot 1637 and a slot 1638 is etched or laser cut, etc., into the embryonic lock 1636. Inner diameter (bore diameter) of the embryonic lock 1636 may be about 0.025 inches and the outer diameter of the embryonic lock 1636 may be about 0.040 inches. Next, the embryonic lock 1636 is placed into crimping fixture 2100 whereby mandrel 2110 is pressed downward onto the slots 1637 and 1638 as may be seen in FIG. 48 to bend the tabs 1639 inward towards the filament 34 as may be seen in FIG. 49. This results in the lock 1640 as may be seen in FIG. 49. As may be seen, cradle 2120 reacts against the force of mandrel 2110.

Similar to the embodiment detailed above with respect to FIG. 33, mandrel 2110 and the slots 1637 and 1638 may be dimensioned such that the slots 1637 and/or 1638 guide the mandrel 2110 during the crimping operation.

It is noted that in some embodiments, the tabs 1639 may be pre-bent inward before crimping. It is further noted that the wall thickness of the embryonic lock 1636 may be varied and/or the dimensions of the slots 1637 and 1638 (including angles seen in the FIGs.), and thus the resulting tabs 1639 may be varied as appropriate.

Figure 50:
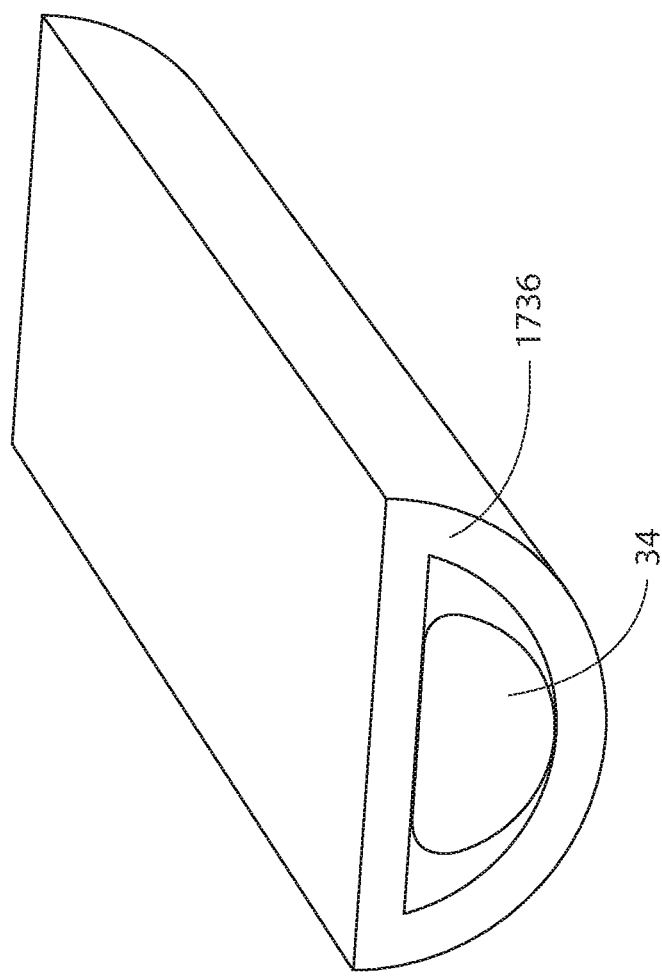
Figure 51:
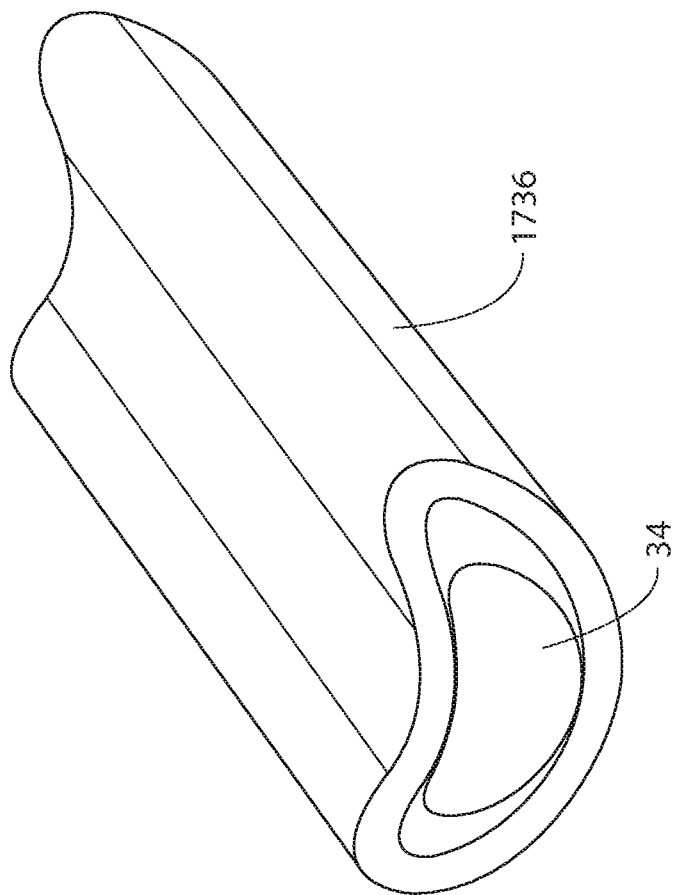

In yet another embodiment, the entire embryonic lock is crimped, as may be seen in FIGS. 50 and 51, where element 1736 is a crimped lock.

Figure 53:
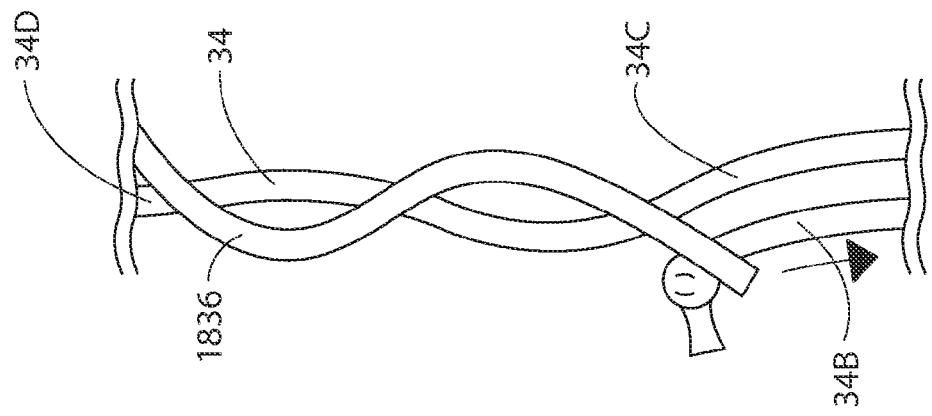
FIGS. 53-55 depict use of the lock of FIG. 52.
Figure 52:
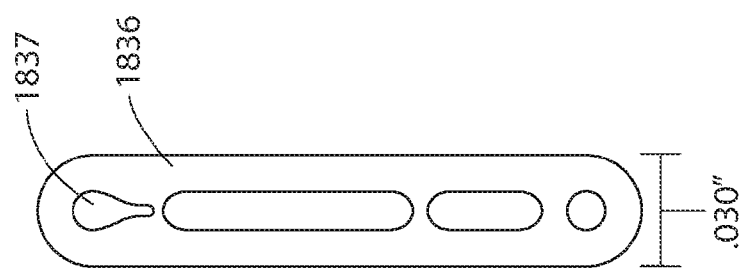
Figure 54:
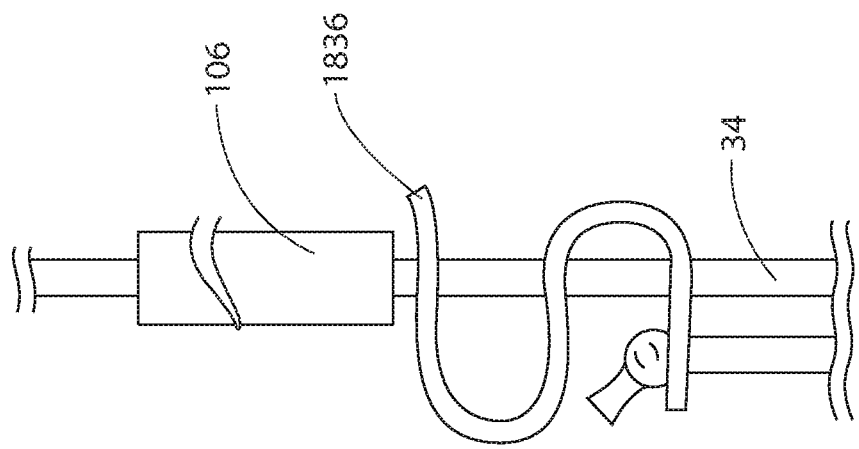
Figure 55:
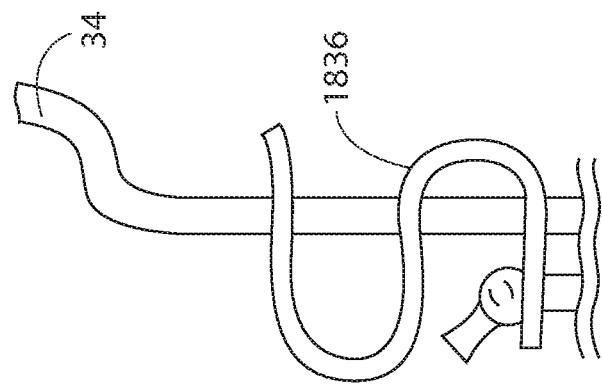

FIG. 52 depicts an alternate embodiment of a lock. Specifically, as may be seen, there is a lock 1836 in the form of a flexible elongated thin plate with various holes therethrough. Filament 34 is woven through the holes of the lock 1836 as may be seen in FIG. 53, with sections 34B and 34C and 34D corresponding to sections 34B and 34C and 34D detailed above. As may be seen in FIG. 53, tensioning the filament 34 results in the lock 1836 deforming from its original flat position. Tamper 106 is used in conjunction with a tension force applied to the filament 34 as may be seen in FIG. 54 to further deform the lock 1836 to the configuration seen in FIG. 55. As may be seen, lock 1836 includes hole 1837 that has a section that is wider than another section, to holes 536C and 536D depicted in lock 536 above in FIGS. 14A-14C. Specifically, a portion of the hole 1836 is narrower than the natural outer diameter of filament 34, and thus provides a limited resistance to movement of filament 34 through the slot. The filament 34 locks into the lock 1836 in the same way that the filament 34 locks into the lock 536 detailed above. In an embodiment, hole 1837 becomes gradually narrower, thus locking the filament 34 in place. In another embodiment, hole 1837 has a relatively constant width.

Figure 56:
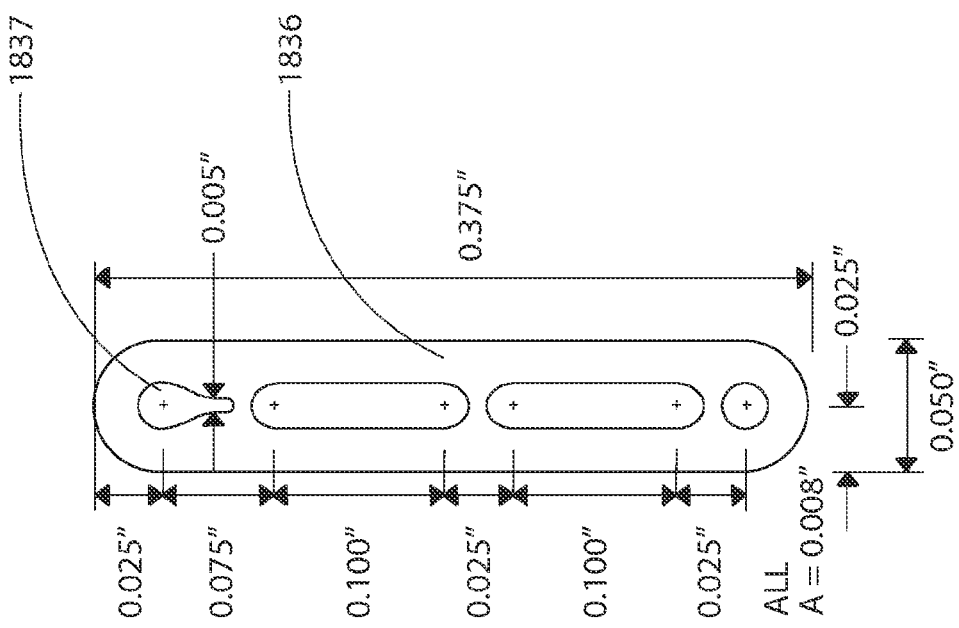
FIG. 56-58 depict additional exemplary embodiments of locks.

FIG. 56 depicts exemplary dimensions of the lock 1836. In an exemplary embodiment, the lock 1836 is 0.002, 0.003, 0.004 or 0.005 inches thick. The hole 1837 tapers to have a width of about 0.005 inches at its base. In an exemplary embodiment, the holes depicted in FIG. 56 are 0.016 inches wide, while in other embodiments, the holes are about 0.025 inches wide (i.e., the bottom hole has a radius of 0.0125 inches). In an exemplary embodiment, the lock 1836 is pre-bent into a slight "S" shape as may be seen in FIG. 53. This helps ensure that the ultimate bent shape of the lock 1836 takes the form as depicted in the figures and permits easier threading of the filament 34 through the holes. It is further noted that in some embodiments, one or more of the elongated holes depicted in FIG. 56 are shorter by about 0.040 inches than that depicted in FIG. 56.

In an exemplary embodiment, the hole 1837 may also be one-sided such that the interior of the hole 1836 favors locking in one direction of filament 34 movement and sliding in the other direction of filament 34 movement. This may, in some embodiments, prevent dragging of the hole 1836 with the filament 34 as the hole 1837 is bent as the lock 1836 is bent.

Figure 57:
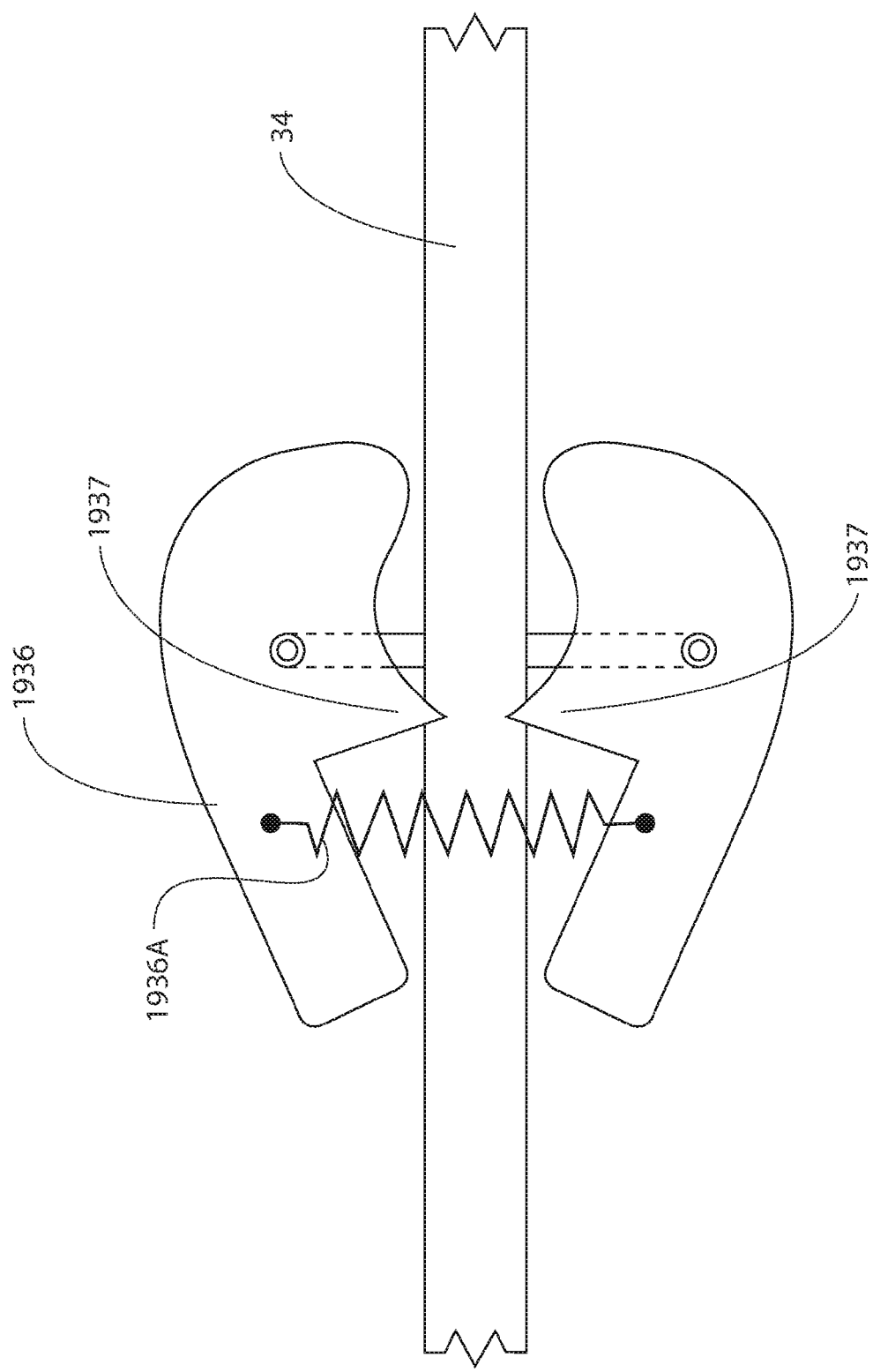
Figure 58:
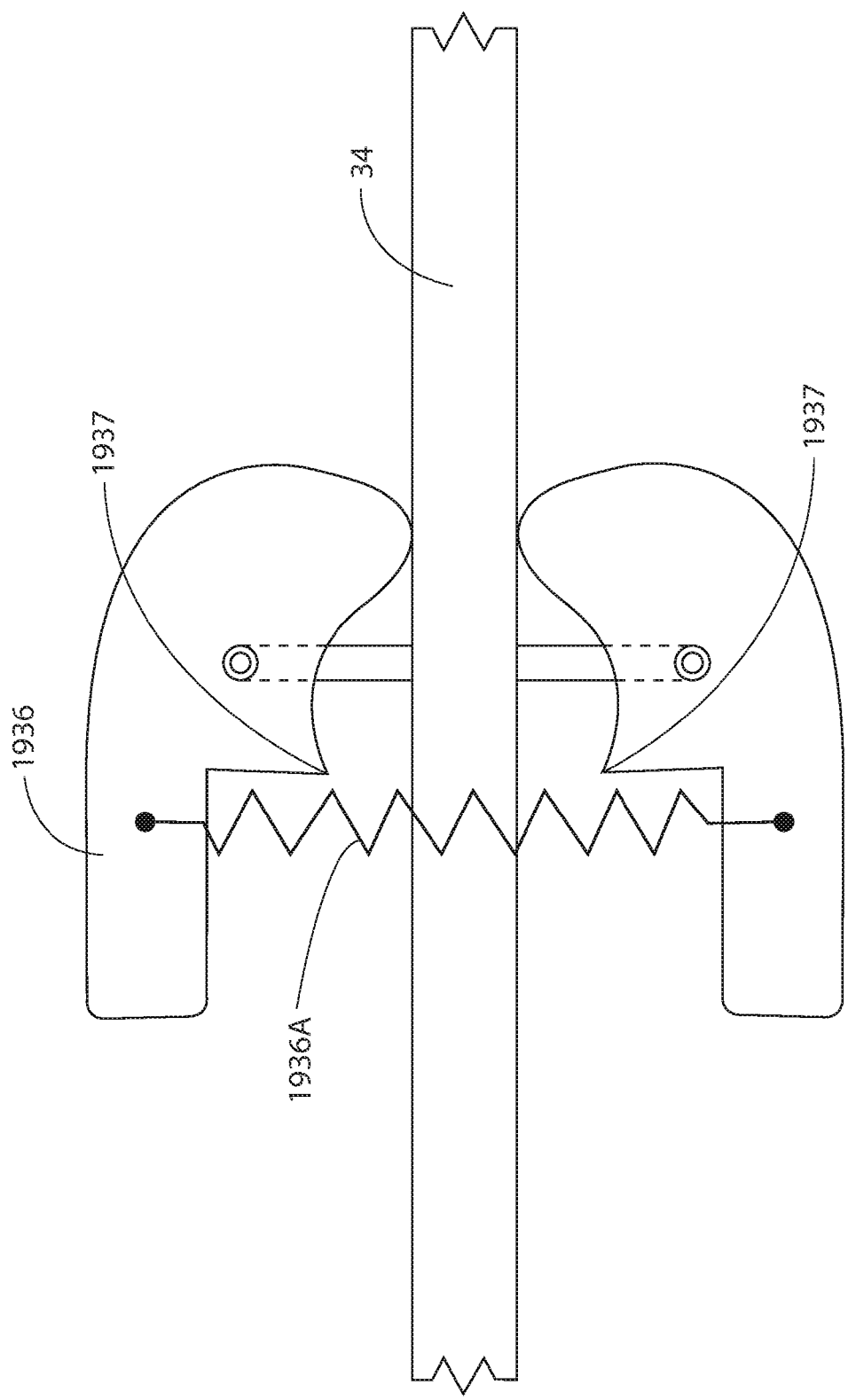
Figure 59:
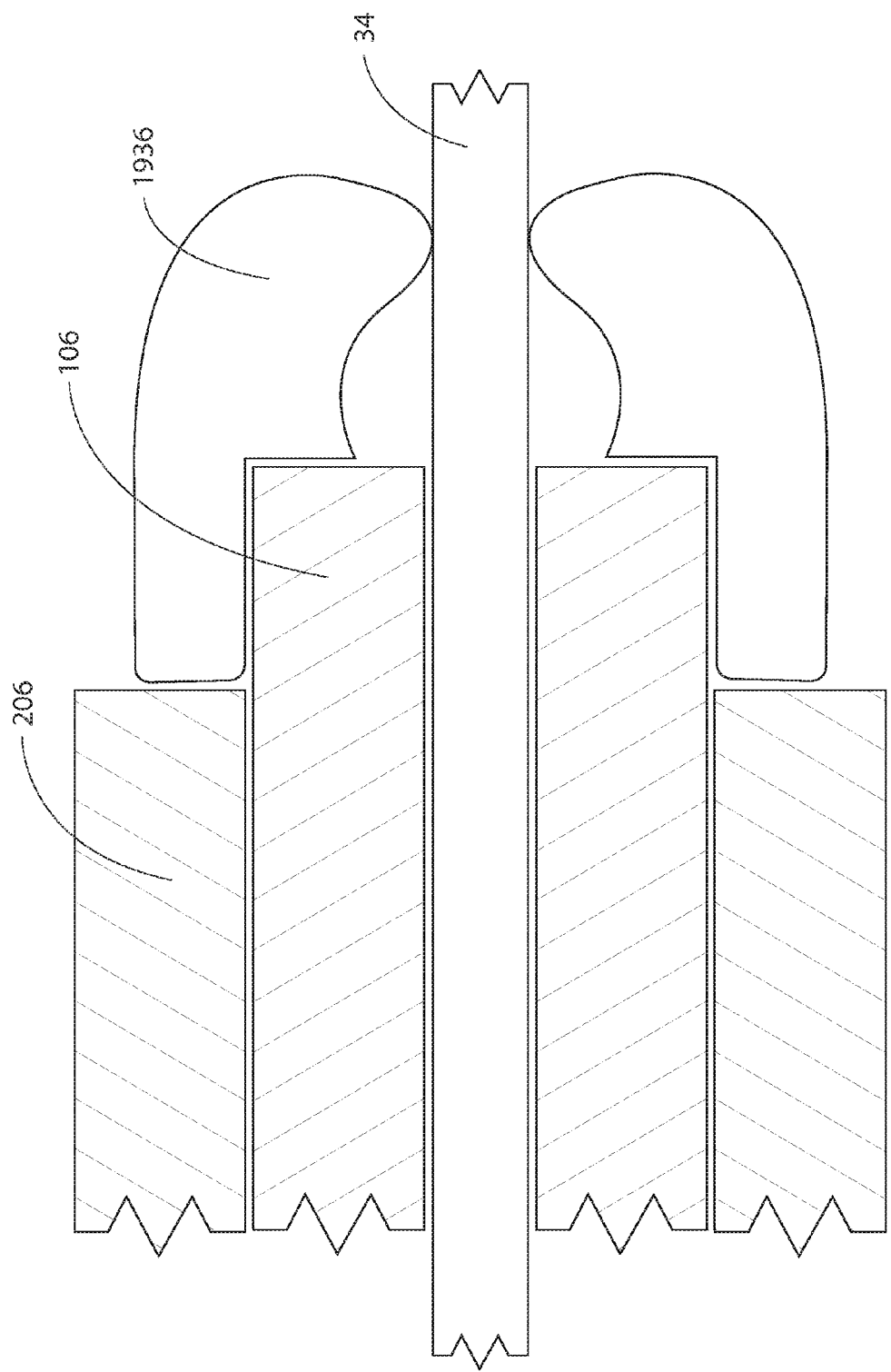
FIG. 59 depicts tampers used to position the lock of FIG. 58.

FIGS. 57 and 58 depict an alternate embodiment of a lock 1936 that clips onto the filament 34 upon release from tamper 106. Specifically, lock 1936 is configured to be biased to conform to the configuration depicted in FIG. 57 vis-à-vis the filament 34 from that depicted in FIG. 58. In an exemplary embodiment, the lock 1936 is spring-loaded by springs 1936A so that it springs to the configuration depicted in FIG. 57, whereby nips 1937 compress the filament 34, thereby increasing the friction force between the lock 1936 and the filament 34 required to be overcome to move the lock 1936 (relative to the friction force, if any, resulting from the configuration depicted in FIG. 58, where the filament easily slides through the lock 1936). In an exemplary embodiment of deploying the lock 1936, the lock 1936 is initially positioned on a tamper 106 as depicted in FIG. 59. As can be seen, tamper 106 holds the lock 1936 in the position depicted in FIG. 58, where little if any friction force must be overcome between the lock 1936 and the filament 34 to move the lock 1936 relative to filament 34. After the lock 1936 is positioned as desired by driving the tamper 106 towards the anchor 32 (i.e., to the right with respect to FIG. 59), the tamper 106 is withdrawn in the opposite direction. The little friction force between the lock 1936 and the filament 34 is sufficient to drag the lock 1936 from the tamper 106, thereby ejecting the lock 1936 from the tamper 106. Alternatively or in addition to this, a second tamper 206 is pushed along the first tamper 106 to drive the lock 1936 from the tamper 106, as depicted in FIG. 59, while applying a tension to filament 34 in the opposite direction of which the second tamper 206 is moved. After the lock 1936 is ejected from the tamper 106 (either through use of tamper 206 or via the little friction that exists between the lock 1936 and the filament before the lock 1936 takes the configuration depicted in FIG. 57), the lock springs to the configuration depicted in FIG. 57, thereby increasing the friction force that must be overcome between the filament 34 and the lock 1936 to move the lock 1936 relative to the filament 34. The tamper may then be advanced again towards the anchor 32 using the tamper 106 to push the lock 1936 along the filament 34 while applying tension to the filament 34 in the opposite direction in a manner analogous to the deployment of the other locks detailed herein.

Figure 60:
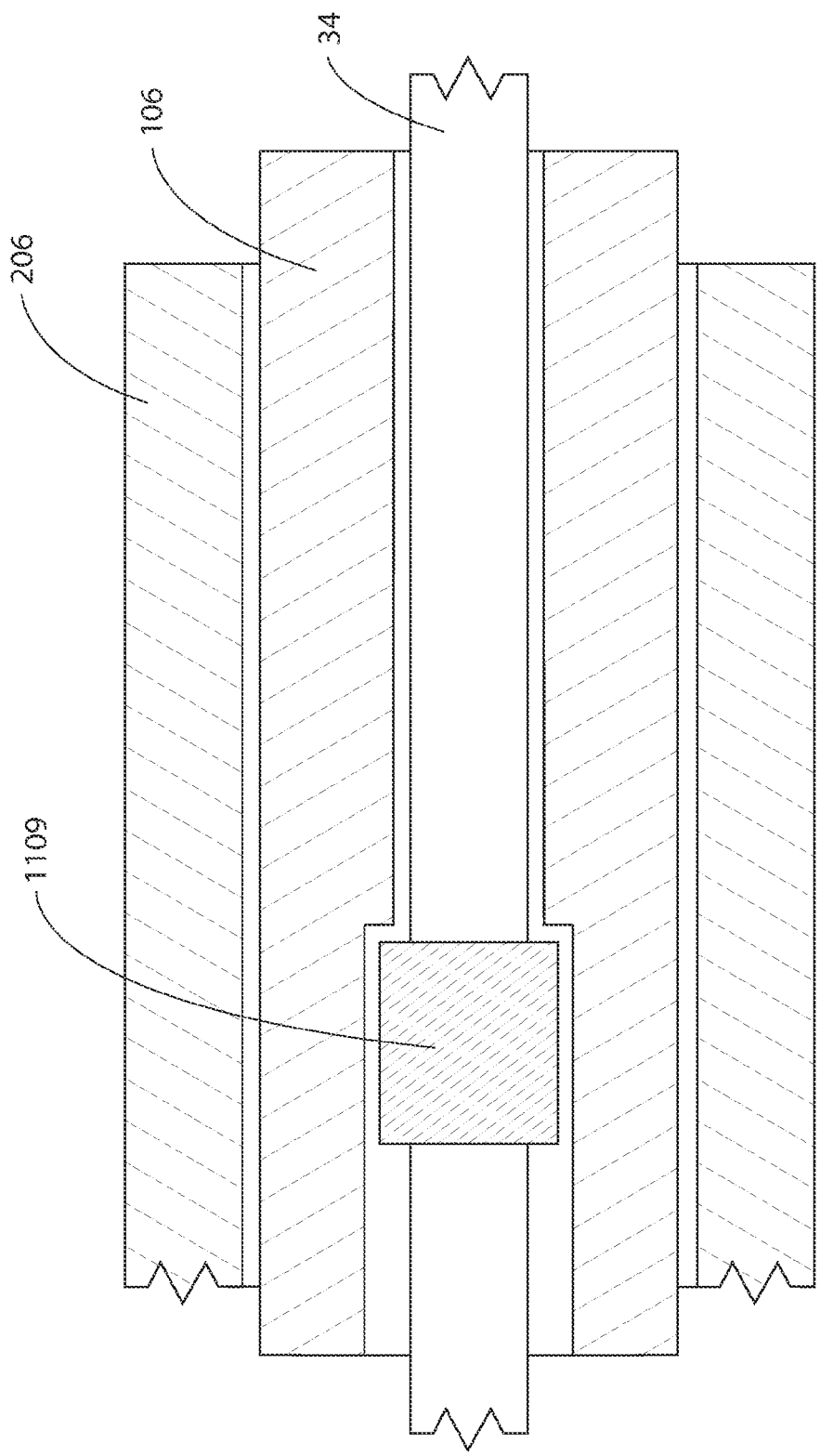
FIG. 60 depicts a portion of one of the tampers of FIG. 59.

In an exemplary embodiment utilizing the dual tampers 106 and 206, a crimp 1109 (or, in an alternative embodiment, a knot) is provided in filament 34 as depicted in FIG. 60 to prevent the tamper 106 from sliding as the tamper 206 is moved relative to the tamper 106 in the event that friction forces develop between the two tampers.

In yet an alternative exemplary embodiment, the lock 1936 is not spring loaded to conform from one configuration to another configuration. Instead, the lock 1936 is a static lock with a nip at the interface of the lock 1936 and the filament 34 that results in a friction force that must be overcome to move the lock 1936 relative to the filament 34 analogous to the friction forces that must be overcome with respect to other embodiments of locks as disclosed herein. Thus, in some embodiments, the lock 1936 functions and is positioned in an analogous manner to the locks detailed above.

Figure 61:
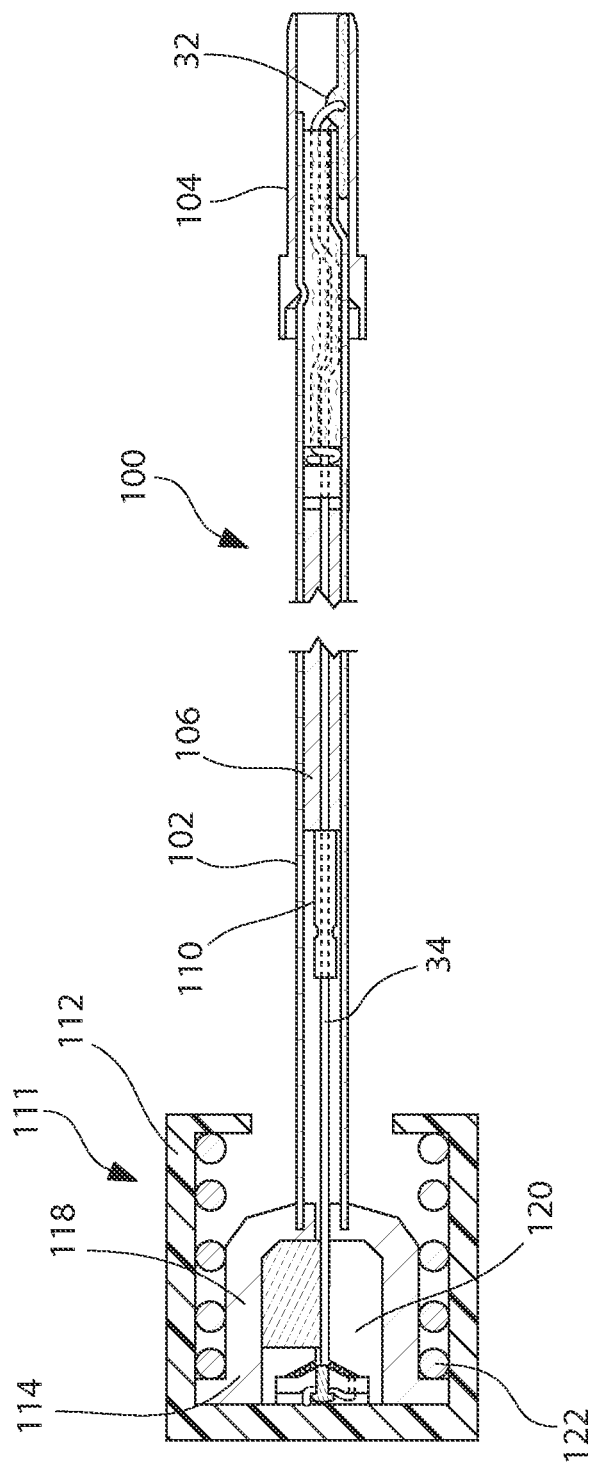
FIG. 61 depicts a deployment instrument according to an exemplary embodiment of the present invention.

An exemplary embodiment of the present invention includes a deployment instrument 100 including an exemplary tensioner assembly 111 as may be seen in FIG. 61. A portion of the procedure involving deployment of the closure device 20 in a recipient using the exemplary tensioner assembly 111 of FIG. 61 will now be described. As may be seen in FIGS. 61 and 62, the tensioner assembly 111 is located at the proximal end (relative to the recipient) of the deployment instrument 100. The tensioner assembly 100 includes a frame 112 in which a hub assembly 114 is slidably retained. The frame 112 serves as a handle that the user may grasp during application of the closure device 20 to the recipient. In some embodiments, the handle is provided with knurling or tread grips or the like to facilitate grasping by the user. The hub assembly 114 includes a hub 118 and a tensioner insert 120. The hub assembly is spring loaded by spring 122 in the proximal direction of the deployment instrument 100. That is, with respect to FIG. 61, the spring 122 forces the hub assembly 114 to the left, relative to the frame 112. Another way of describing this is that the spring 122 forces the frame 112 to the right, relative to the hub assembly 114.

The proximal end of the carrier tube 102 is connected to the hub 118 of the hub assembly 114 as may be seen. Collectively, carrier tube 102 and hub assembly 114 form a carrier assembly. Thus, the spring 122 indirectly spring loads the carrier tube 102 in the proximal direction of the deployment instrument 100 relative to the frame 112. In an exemplary embodiment, the spring 122 permits the tension on filament 34 to be controlled/ensures that sufficient tensioning and not too much tensioning is applied to the filament during deployment of the closure device 20, as will now be detailed.

Figure 62:
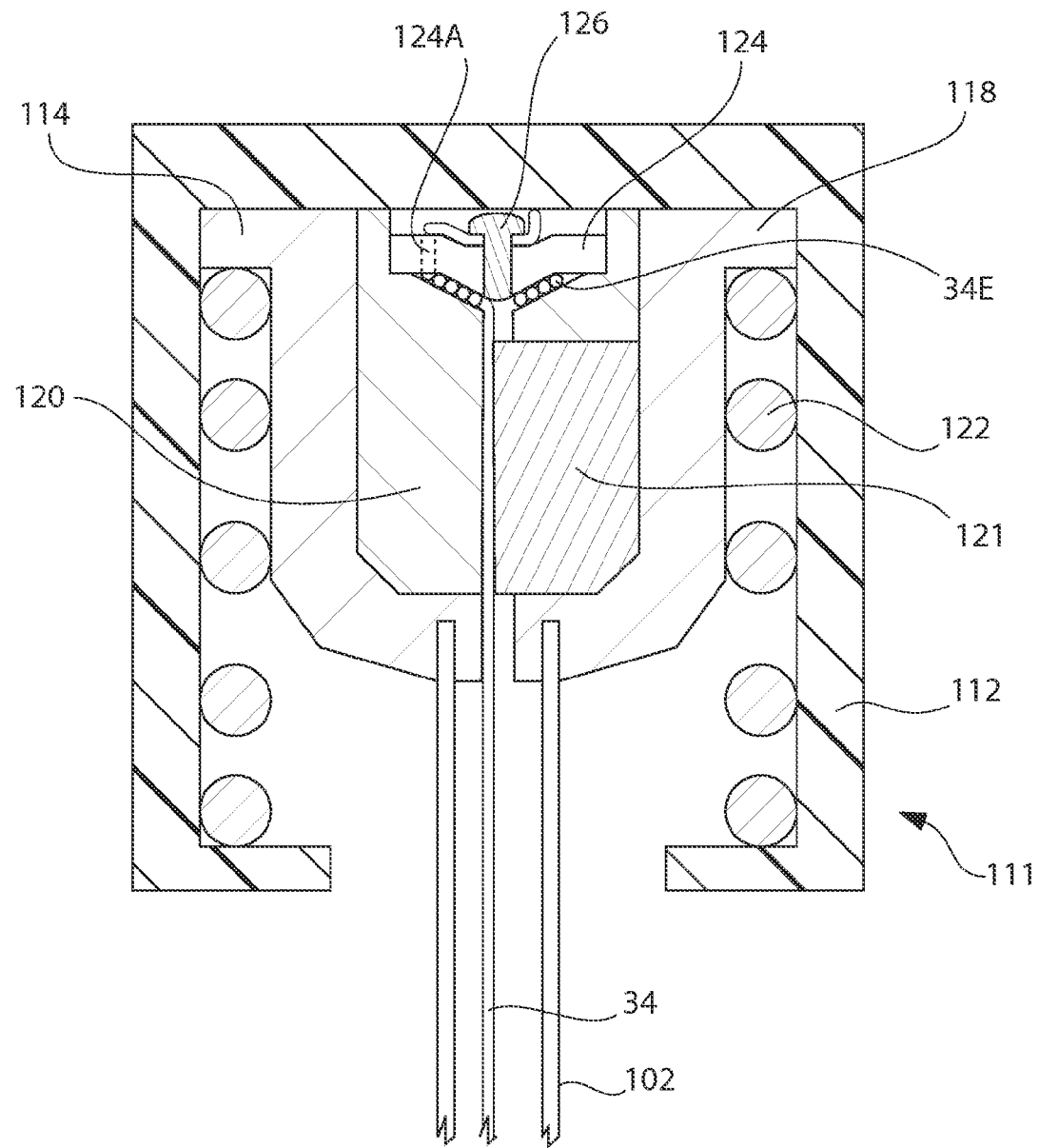
FIGS. 62-68 depict exemplary embodiments of a tensioner assembly usable in the deployment instrument of FIG. 61.

Referring to FIG. 62, the tensioner assembly 111 includes a suture recess between the tensioner insert 120 and a filament cap 124 in which filament 34 is wound in a coil section 34E, from which the filament 34 travels through the carrier tube 102 to the closure device 20. The end of the filament 34 is threaded through a hole 124A in the filament cap 124 and is trapped between the filament cap 124 and a filament lock 126 to hold the end of the filament 34 in place. Filament lock 126 may be held to filament cap 124 via a screw fit or a snap fit or through the use of an adhesive or a weld, etc.

As may be seen in FIG. 62, a friction block 121 is located in a cut-out section of the tensioner insert 120. In an exemplary embodiment, the friction block 121 is a silicon block that is dimensioned such that when inserted in the hub 118 along with tensioner insert 120, a compressive force on filament 34 is applied by the friction block 121 and the hub 118. In some exemplary embodiments, as will be described in greater detail below, as the filament 34 (filament from section 34E) is drawn from the spool of the tensioner assembly 111, the user feels a relatively constant resistance and/or a relatively consistent resistance as compared to other deployment instruments 100 (i.e., the resistance felt with one deployment instrument 100 used during a given procedure will be about the same as that felt during a prior procedure with another deployment instrument 100). That is, the friction block 121 in combination with the tensioner insert 120 and hub 118 function to control the force required to at least initially withdraw the filament 34 from the spool.

During application of the closure device 20, the user pushes the carrier tube 102 of the deployment assembly 100 through the introducer sheath by applying a force on the frame 112 in the distal direction (towards the recipient) until the user estimates that the anchor 32 is located in the blood vessel. Once the anchor 32 has been properly deployed in the vessel, the plug 30 (or plug 70) is deployed into the puncture tract. To that end, the introducer sheath and the deployment instrument 100 are held together and withdrawn as a unit from the puncture. In an exemplary embodiment, the introducer sheath and the deployment instrument 100 snap together such that it is only necessary to apply a force to one of those components in the proximal direction (relative to the patient). The components may include alignment indicia that facilitate alignment of the two components. For example, the deployment instrument 100 and the introducer sheath may include arrows that, once aligned (e.g., the tips contact each other and the respective directions of the arrows are parallel to each other).

Figure 63:
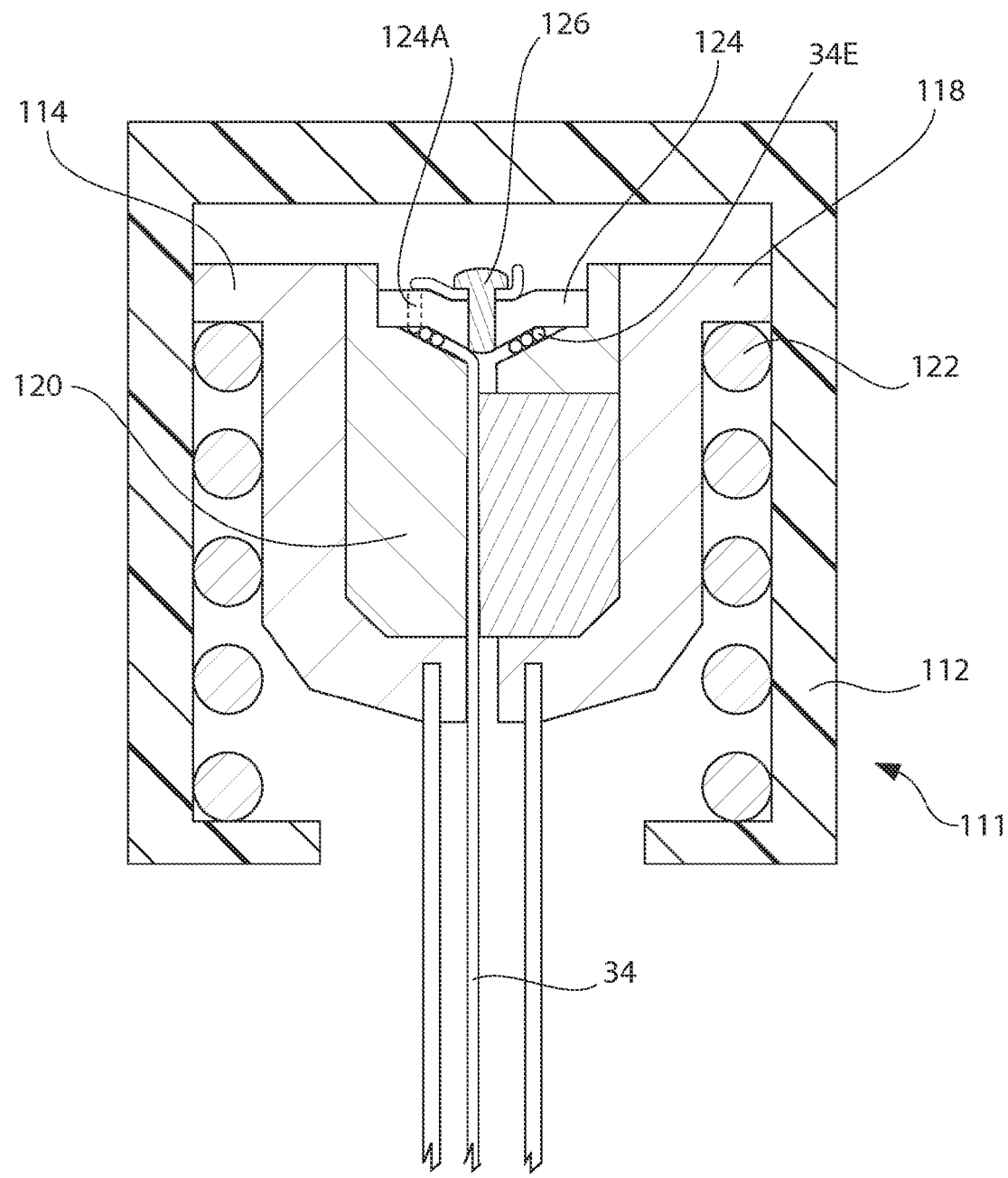
Figure 64:
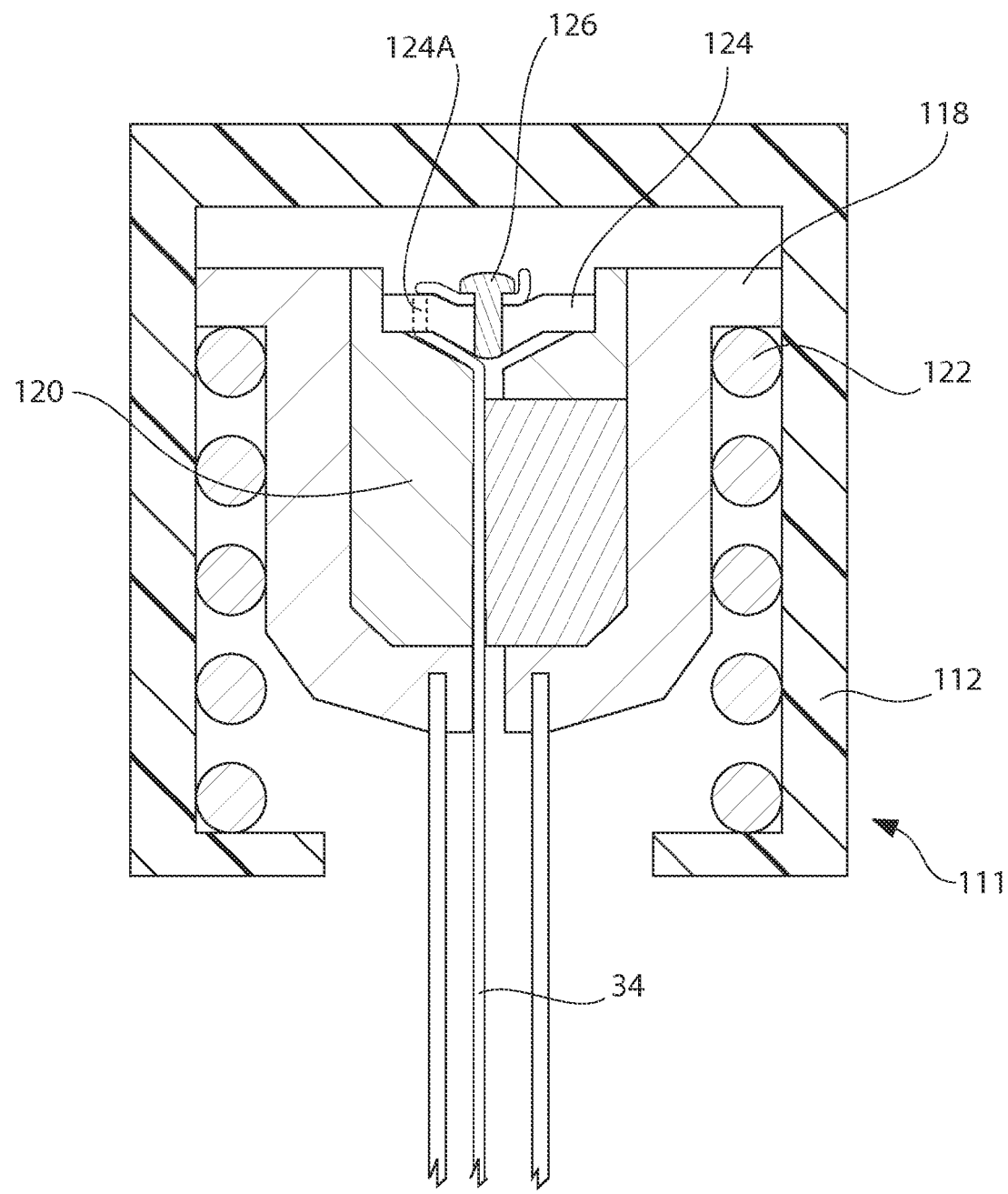

This action causes the anchor 32 to engage or catch onto the inner surface of the artery 26 wall contiguous with the opening 24A. The introducer sheath and the deployment instrument 100 are then pulled further outward. Inasmuch as the anchor 32 is trapped (anchored) against the interior of the artery wall, the continued retraction of the introducer sheath and deployment instrument 100 causes the filament 34 to pull the plug 30 (or plug 70) out of the carrier tube 102 of the deployment instrument 100 and into the puncture tract 24B. Also, once the anchor 32 catches on the wall of the artery 26, the filament 34 (filament from section 34E) will be drawn from the spool of the tensioner assembly 111. Some resistance will be felt, at least in embodiments utilizing the friction block 121 described above (as opposed to other embodiments where no drag force is applied to the filament as a result of compression of the filament by the friction block, such as in the case where no friction block 121 is used and a bore or other space of the tension insert 120 through which the filament 34 passes is oversized relative to the filament 34). This resistance may require the user to apply about ¾ths of a pound of force to the deployment instrument 100 to pull the filament 34 out of hub 118. The user continues to pull the deployment instrument 100 and the introducer sheath away from the recipient with a force sufficient to overcome the friction resulting from the compressive force applied to the filament 34 by the friction block 121. At a given distance of the deployment instrument 100 and the introducer sheath from the recipient, the filament 34 will be completely unwound from the spool. FIG. 63 depicts the tensioner assembly 111 in the state where the filament 34 is about ½ way unwound from the spool and FIG. 64 depicts the tensioner assembly 111 in the state where all of the filament 34 has been unwound from the spool. The tension on filament 34 is high enough to unwind the filament from the spool, and compresses spring 122 by a corresponding amount.

At this point, when the deployment instrument 100 is located a first linear distance from the vessel wall, because the end of the filament 34 is trapped between filament cap 124 and the filament lock 126, continued pulling of the delivery instrument 100 away from the recipient (past the first distance), when the user holds the frame 112 to pull the delivery instrument 100, causes the filament 34 to become more tensioned because the "unwinding" of the filament 34 from the spool has stopped (there is no more filament from section 34E to be unwound) and the end of the filament 34 is held in place as it is attached to the deployment instrument 100. Accordingly, this increase in tension as the user moves the deployment instrument 100 from the first distance from the vessel wall causes frame 112 to move relative to hub assembly 114 and thus causes spring 122 to further compress. The force compressing the spring 122 is substantially equal to the tension in the filament 34. As the tension of the filament 34 progressively increases as the user continues to pull the deployment instrument 100 away from the recipient (via pulling on the frame 112), the spring 122 continues to be compressed, thus resulting in a gradual increase in the tension of the filament 34 as the deployment instrument 100 is continued to be pulled away from the recipient. This as compared to the relatively sudden increase in tension that would exist if the hub assembly 114 were instead rigidly fixed to the tensioner assembly 111 and/or the spring 122 were not present. In this regard, the spring 122 provides a dampening or cushioning effect with respect to the force applied to the inner wall of the blood vessel or other body passageway which reacts against the anchor 32 at the time that the filament 34 is fully unwound from the spool. Thus, there should be no sudden increase in the force/pressure on the wall at the location of the anchor 32. Instead, there should be a gradual increase in the force/pressure on the wall at the location of the anchor 32. In an exemplary embodiment, the hub assembly 114 may travel about eight (8) millimeters upon the application of about two (2) pounds of tension force in the filament 34 before bottoming out (i.e., the hub assembly 114 cannot move further to the right/the frame 112 cannot move further to the left with respect to FIG. 61). Thus, an embodiment provides a mechanically induced increasing tension force applied to the filament that increases with increasing distance of the deployment instrument away from the puncture at a rate of less than about 1.5 pounds per 4 mm of increased distance of the deployment instrument away from the puncture. Accordingly, in an exemplary embodiment, pulling the deployment instrument 100 away from the puncture while the filament is connected to the deployment instrument results in an initial contact of the anchor to the wall of the body passageway followed by a gradual increase in pressure applied to the wall by the anchor while tension in the filament is less than about two (2) pounds. Thus, via a mechanical device of the deployment instrument 100, a sudden increase in pressure applied to the wall of a body passageway by the anchor 32 is avoided.

Figure 65:
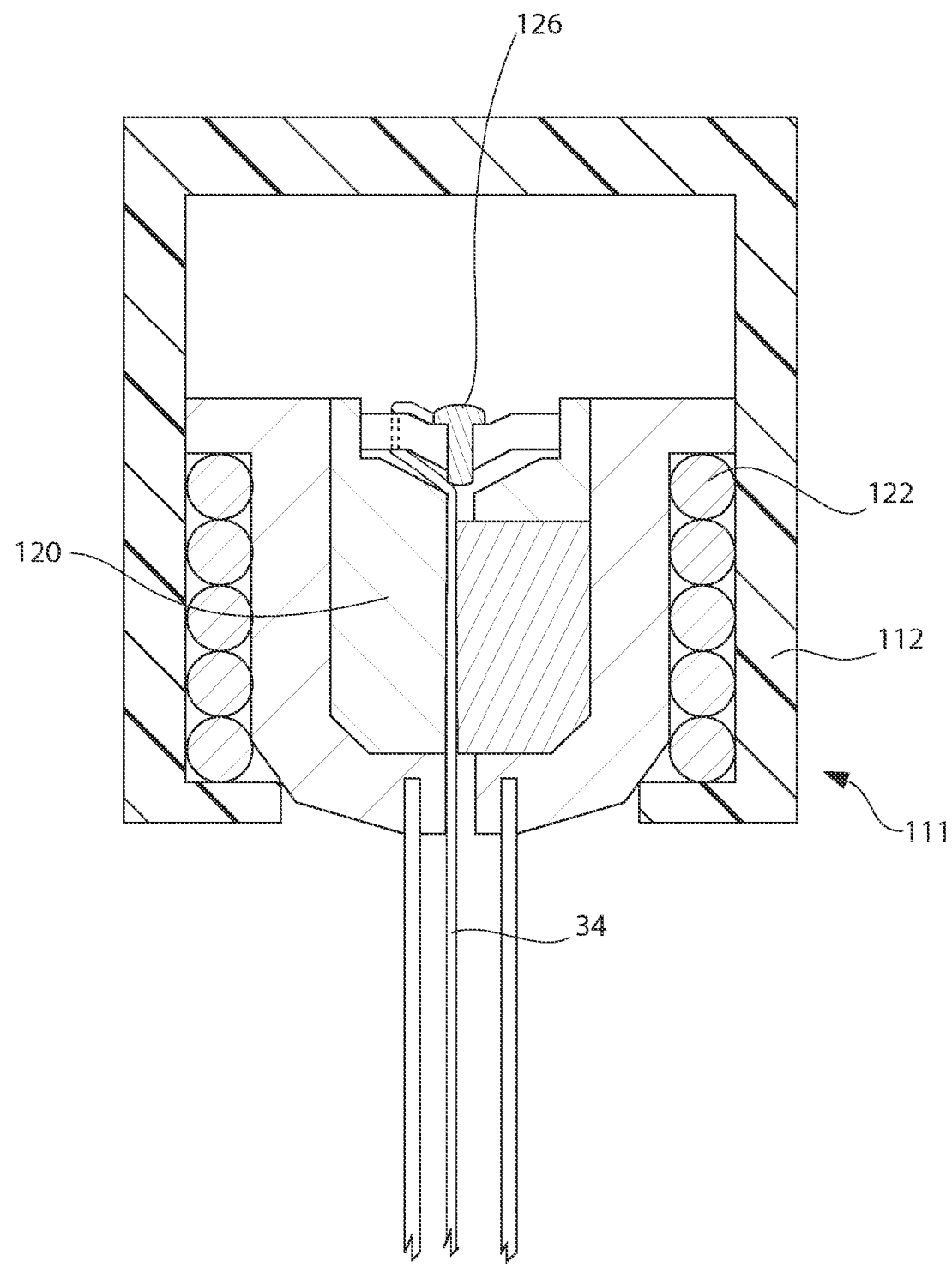

FIG. 65 depicts spring 112 fully compressed upon the application of two (2) pounds of tension force in the filament 34 by the user while filament 34 is connected to anchor 32 (which, as noted above, is lodged in the artery 26). By bottoming out the hub assembly 114, and not pulling on the deployment instrument 100 too much more after that, the user can ensure that he or she has applied about two (2) pounds of tension force on the filament 34, and not too much more. This ensures that sufficient tension has been applied to the filament to properly deploy the closure device 20, and not too much more. Also, the spring 122 at least partially reduces what otherwise might be a spike in the force applied to the wall of the artery 26 upon the filament 34 becoming completely unwound from the spool and becoming unslackened due to movement of the deployment instrument 100 away from the recipient.

In an exemplary embodiment, the user feels/senses the gradual increase in tension as the spring 122 is compressed (as compared to the relatively static tension resulting from friction block 121), and thus is provided an indication that the deployment instrument 100 will soon reach the mechanical limits of its withdrawal away from the recipient, after which any further withdrawal will be due to the plastic and/or elastic nature of the filament and the recipient. In some embodiments, the spring 122 is a linearly compressible spring, and thus the gradual increase in tension as the spring 122 is compressed is linear. Non-linear compressible springs may also be used, in which case the gradual progressive increase in tension is not linear. In an exemplary scenario of use, the user continues pulling the deployment instrument 100 away from the recipient until the spring 122 bottoms out, and then halts further movement of the deployment instrument 100 away from the recipient. Alternatively, the user can continue to pull the deployment instrument 100 away from the recipient, thereby further increasing the tension in the filament 34. Even with respect to this latter scenario, the indication afforded to the user by the spring 122 provides the user with an opportunity to adjust the deployment procedure to avoid injury to the recipient and/or damage to the closure device, etc.

It is noted that as the delivery assembly 100 is pulled away from the recipient, and by the time that the spring 122 has bottomed out, the pulley arrangement of the filament 34 connecting the anchor 32 and the plug 30 causes the plug 30 to be moved into engagement with the exterior of the artery wall contiguous with the puncture. The tension in the filament 34 resulting from pulling the deployment instrument 100 away from the recipient causes the filament 34 to somewhat deform the plug, i.e., cause it to deform radially outward and, in some embodiments, twist. Because the spring 122 permits the tension on filament 34 to be controlled/ensures that sufficient tensioning and not too much tensioning is applied to the filament during deployment of the closure device 20, the user is provided with some reassurance that the proper amount of tensioning has been applied to the filament 34 to deform the plug and properly deploy the closure device 20.

It is further noted that in some embodiments of the present invention, the movement of the carrier tube 102 relative to the housing 112 as a result of the tension applied to filament 34 results in the tip of the carrier tube 102 being pulled out beyond the end of the introducer sheath. That is, the carrier tube 102 will move relative to the introducer sheath in embodiments where the introducer sheath abuts or otherwise contacts the housing 112 such that the housing 112 and the introducer sheath move in unison together (e.g., in the case where the introducer sheath and the housing 112 mechanically mate with one another) during a portion of the deployment procedure of the closure device. By dimensioning the introducer sheath and the carrier tube 102 to have certain lengths, and by designing the delivery assembly 100 to permit the hub assembly 114 to travel a sufficient distance relative to the housing 112, the tip of the carrier tube 102 may extend beyond the end of the introducer sheath upon full or even partial compression of spring 122. In an exemplary embodiment, this will permit the plug 30 to be drawn from the carrier tube 102 without contacting the introducer sheath or at least without contacting the interior of the introducer sheath. This may, in some embodiments, eliminate the possibility that the plug 30 might become stuck in the introducer sheath during the deployment procedure as it expands once leaving the carrier tube 102.

Figure 66:
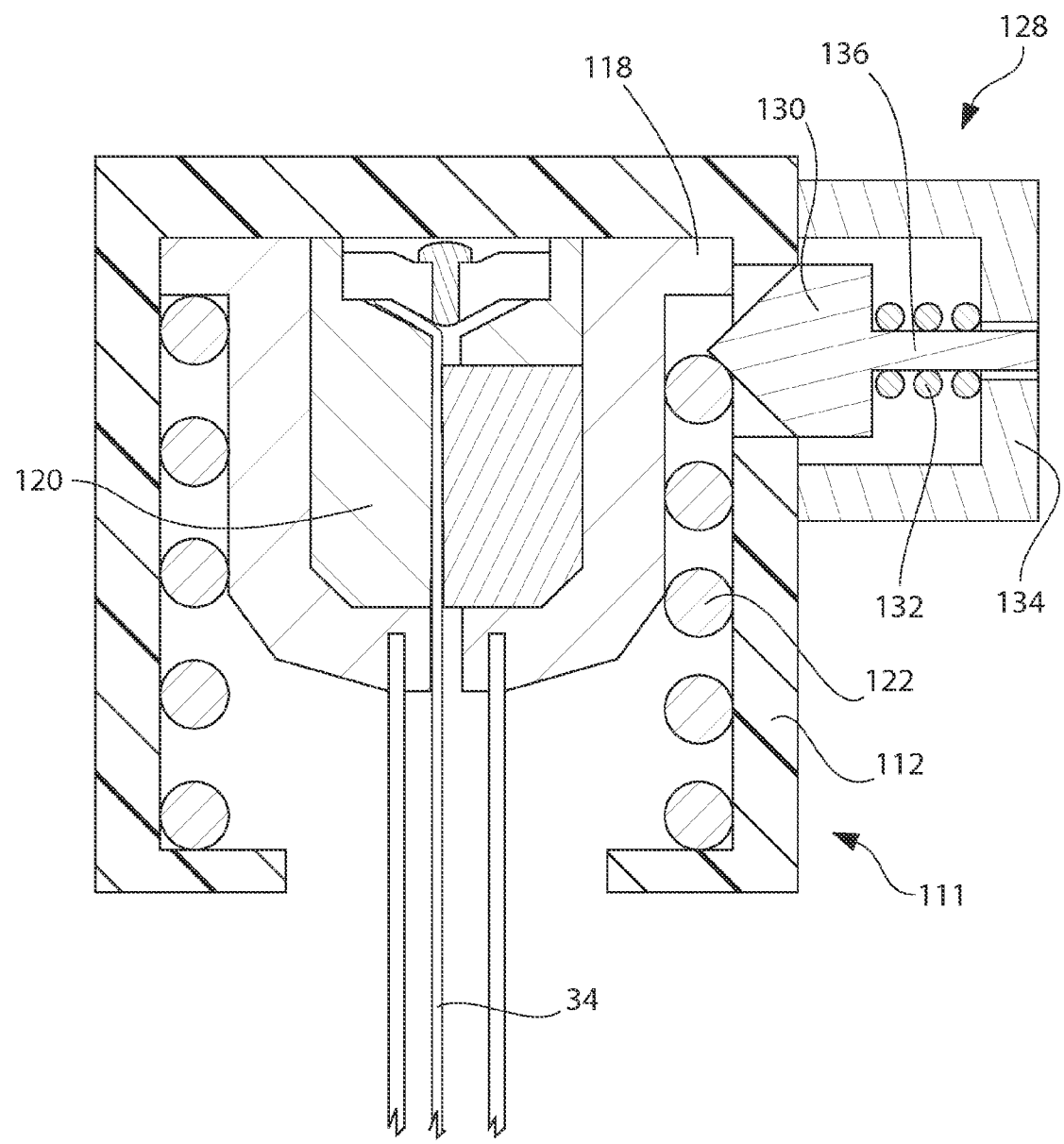
Figure 67:
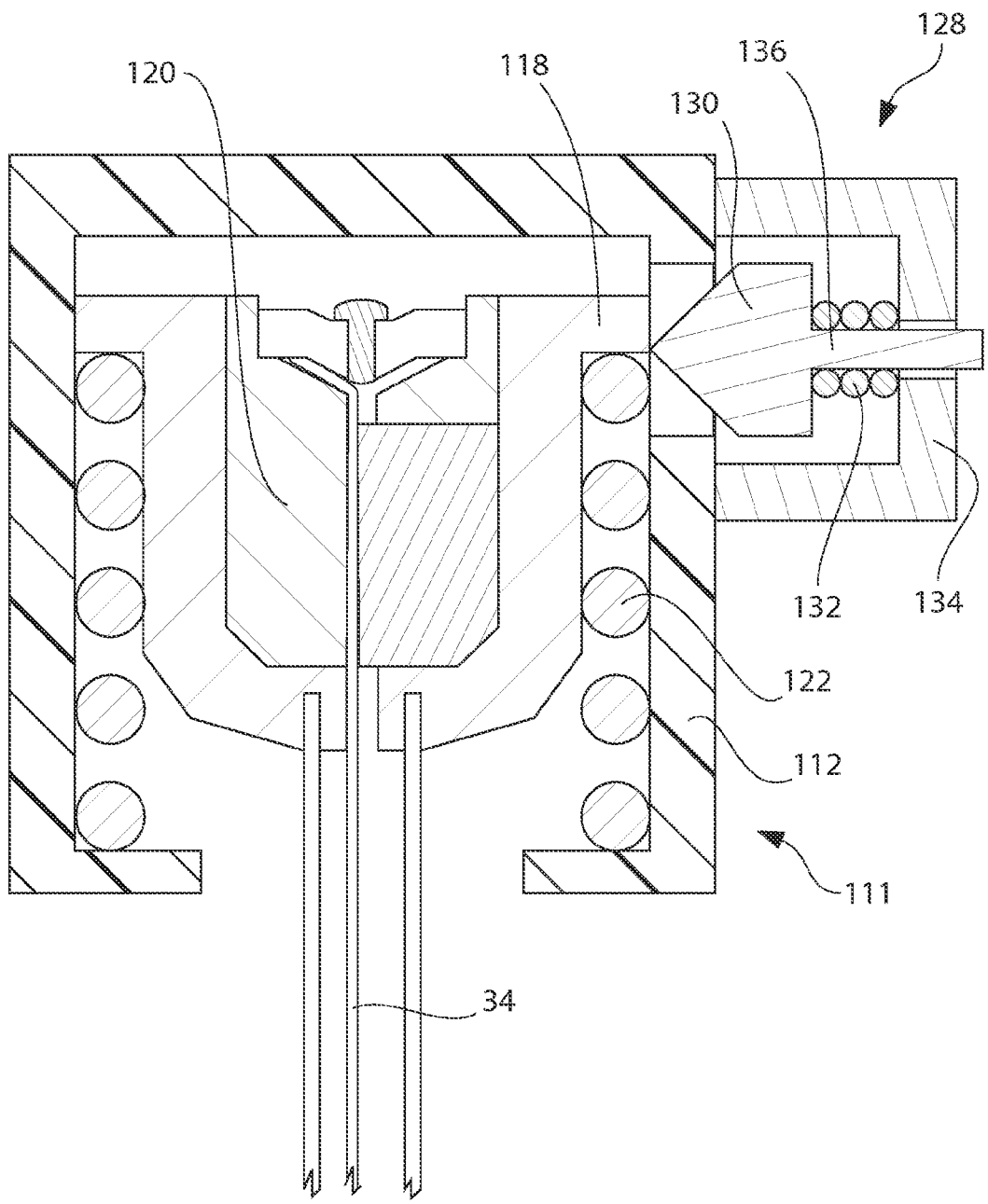
Figure 68:
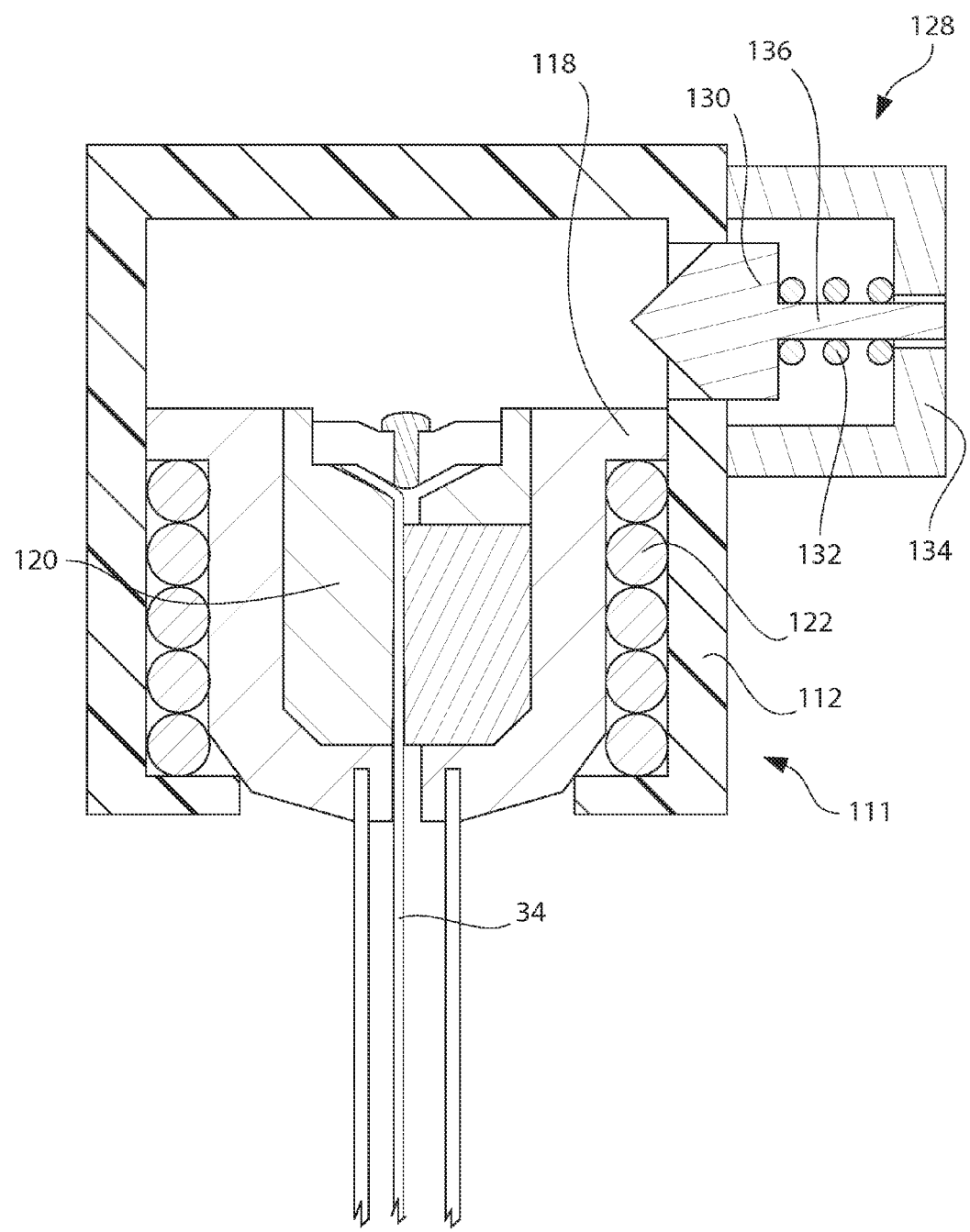

FIGS. 66-68 depict an alternate embodiment of the present invention that includes an indicator 128 that provides an indication to the user that the hub assembly 114 has bottomed out within the frame 112. The indicator includes a stylus 130 that is spring loaded via a spring 132 and is contained in a housing 134 on the side of or embedded in the frame 112. As the hub 118 moves relative to the frame 112/the frame 112 moves relative to the hub 118, the stylus is forced to the right, relative to FIGS. 66-68, as may be seen in FIG. 67. Once the hub 118 clears the stylus (which is or is about the point where the hub 118 bottoms out in the frame), as may be seen in FIG. 68, the stylus springs back to the left (relative to FIGS. 66-68). This makes a clicking noise which may be heard and/or felt by the user. Alternatively or in addition to this, a visual indicator 136 extends out of the housing 134 as the hub 118 passes the stylus 130, as may be seen in FIG. 66. It is noted that in some embodiments, the visual indicator is combined with the audio indicator, as is depicted by way of example in FIG. 67, while in other embodiments, the audio indicator and the visual indicator are separate (and thus, for example, each indicator may have its owned stylus). Still referring to the embodiment of FIGS. 66-68, once the hub 118 passes the stylus, the visual indicator 136 is withdrawn into the housing 134, its disappearance a visual indicator to the user that the hub 118 has or is about to bottom out. This provides the user an indication that he or she should stop moving the deployment instrument 100 away from the recipient and/or continue to do so with additional caution.

In an alternate embodiment, the indicator 128 is configured to provide an indication when the hub 118 has moved away from its bottomed out position. That is, the user may receive two indications—one indication when the hub 118 bottoms out/about bottoms out and one indication when hub 118 moves from its bottomed out position. This provides the user with an indication that, in the first instance, any additional movement of the deployment instrument 100 away from the recipient will not be cushioned by the spring 122, and in the second instance, that the user has decreased the tension on the filament 34 from that present when the hub 118 bottomed out.

Figure 69:
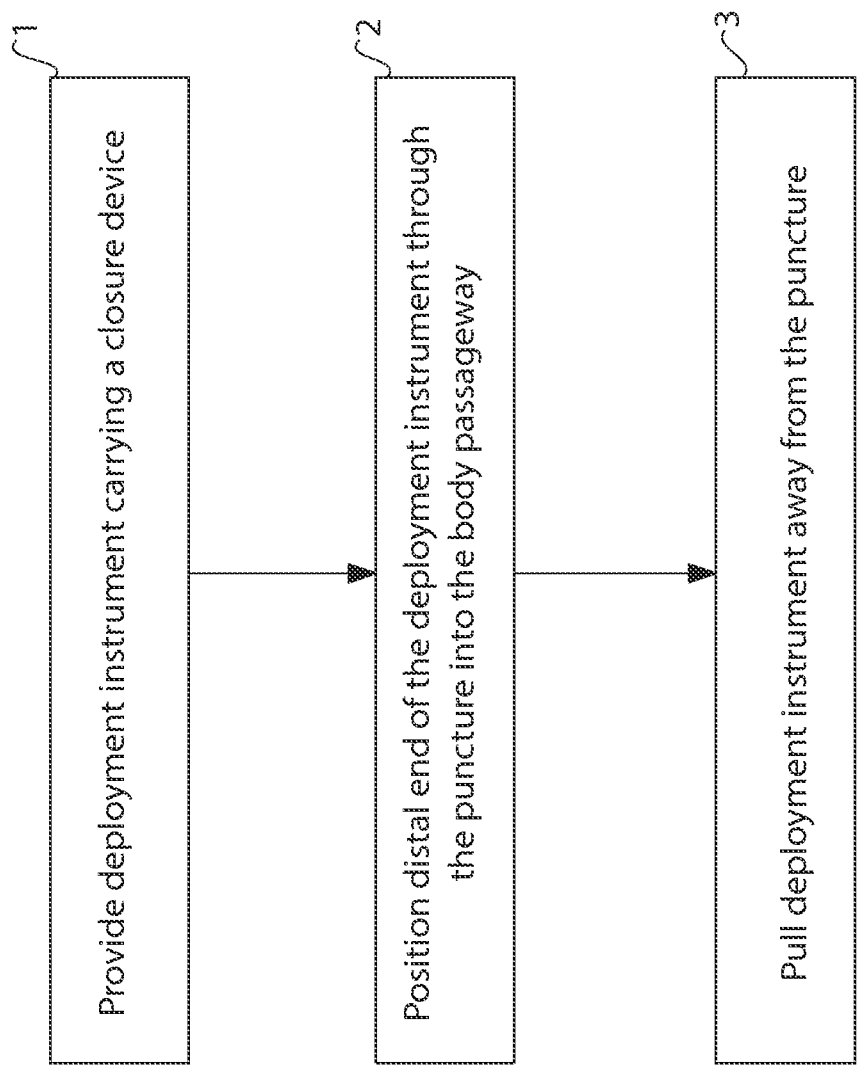
FIG. 69 presents a flowchart of an exemplary method of deploying the closure device.

Accordingly, in an exemplary embodiment, referring to the flowchart of FIG. 69, there is a method of sealing a percutaneous puncture in a wall of a body passageway, comprising, at step 1, providing a deployment instrument 100 including a tensioner assembly 111 and carrying a closure device 20, the closure device 20 including an anchor 32, a plug 30 and a contiguous elongate filament 34 configured to draw the plug 30 towards the anchor 32 upon the application of tension to the filament 34 in a direction away from the anchor 32. At step 2, the distal end of the deployment instrument 100 is positioned through the puncture into the body passageway such that the anchor 32 is located in the body passageway. At step 3 the deployment instrument 100 is pulled away from the puncture while the filament 34 is connected to the deployment instrument. This results in the application of a mechanically induced increasing tension force to the filament 34 that increases with increasing distance of the deployment instrument 100 away from the puncture, thereby drawing the anchor 32 and the seal 30 towards each other and into engagement with the wall of the body passageway at respectively opposite sides of the wall. In an exemplary embodiment, the mechanically induced increasing tension force is a result of spring 122, as detailed above.

It is noted that as the deployment instrument 100 is pulled away from the recipient, the tamper 106 is ejected from the carrier tube 102 because the end of the tamper 106 catches on the tag 100. The user then grips the tamper 106 and applies a force to the tamper 106 in the distal direction (towards the recipient). That is, the tamper 106 is sufficiently exposed from the carrier tube 102 so that the tamper 106 may be manually slid down the filament section 34 by the user (using his or her other hand) so that it enters the puncture tract 24B and engages the proximal side of the lock 36. As noted above, the user applies a manual force to tamper 106 sufficient to overcome the resistance to movement of the lock 36 relative to the filament 34 due to the protrusions 36B. The lock is moved along the filament 34 while applying a tension to the filament 34 in the opposite direction (such that the spring 112 is maintained in a bottomed-out state) until the lock 36 is sufficiently positioned as detailed herein. The tamper 106 is then withdrawn from the puncture and the suture 34 is cut above the lock 36, thus freeing the deployment instrument 100 from the closure device 20.

Figure 70:
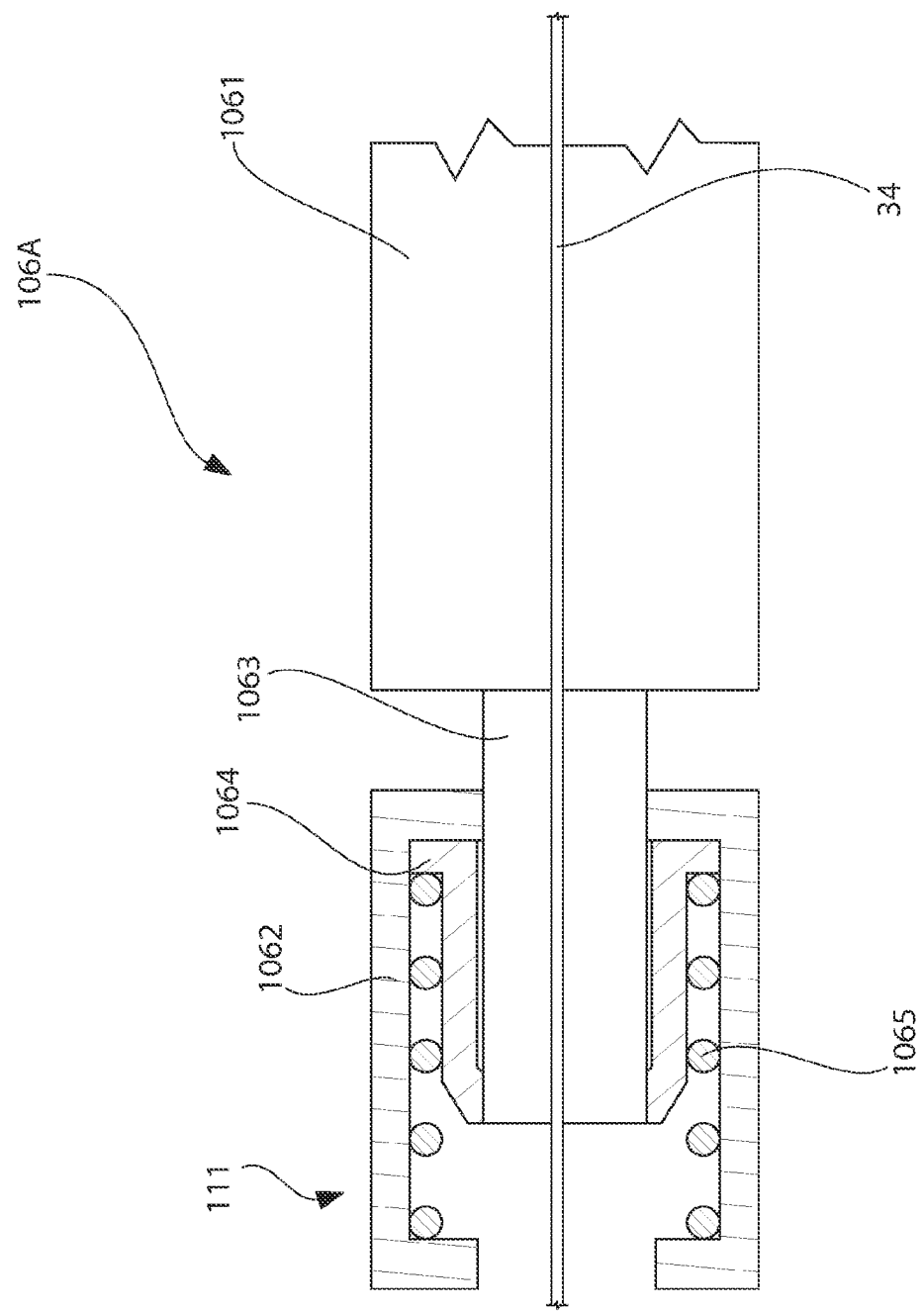
FIGS. 70 and 71 present exemplary embodiments of a tamper according to an exemplary embodiment of the present invention.
Figure 71:
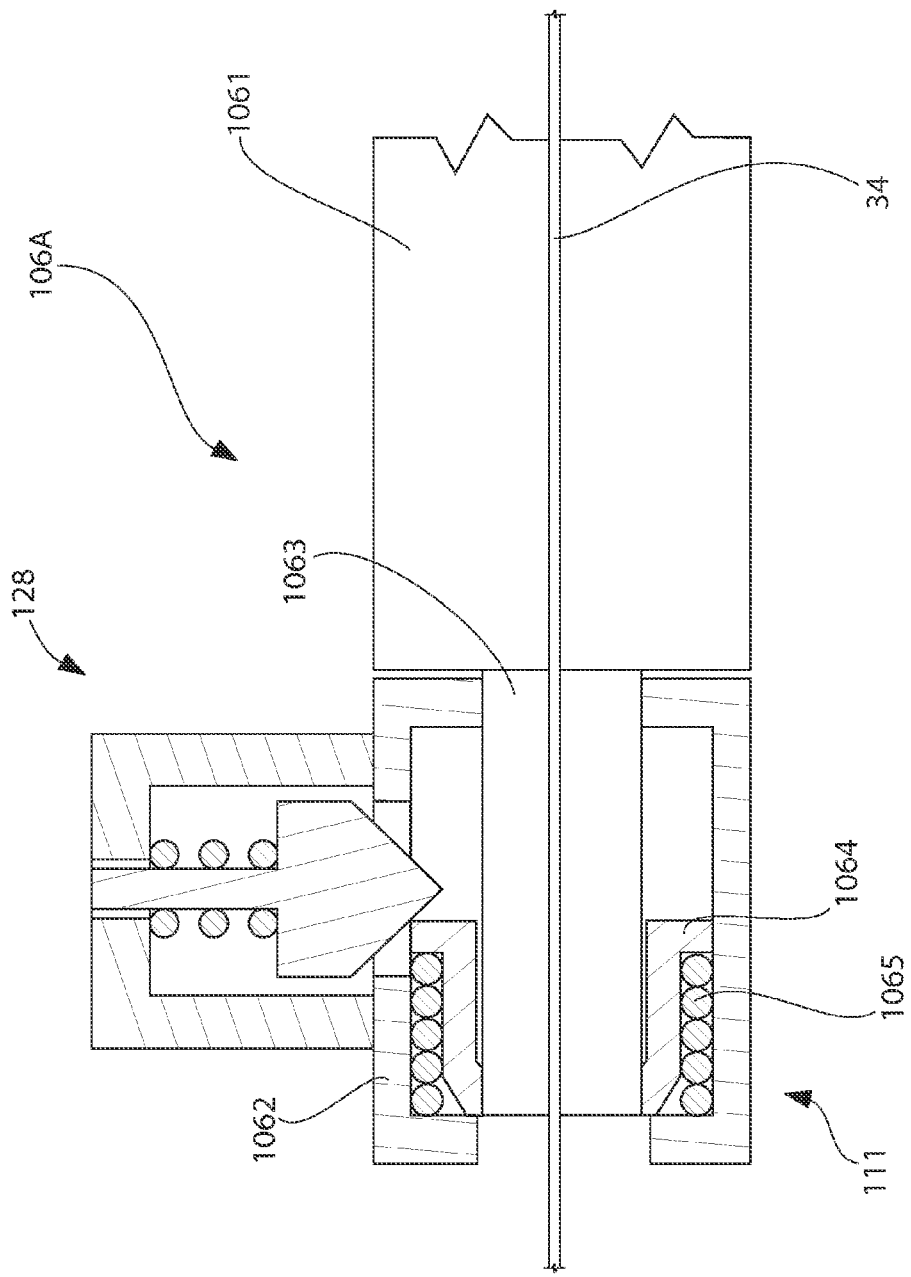

An exemplary embodiment of the present invention includes a deployment instrument 100 including an exemplary tamper assembly 106A as may be seen in FIGS. 70 and 71. A portion of the procedure involving deployment of the closure device 20 in a recipient using the exemplary tamper assembly 106A of FIG. 70 will now be described. As may be seen in FIGS. 70 and 71, the tamper assembly 106A includes a tamper body 1061 (a portion on the proximal end, relative to the recipient, being shown in FIGS. 70 and 71), which substantially corresponds to the tamper 106 detailed above, and has a bore through which the filament 34 extends. Indeed, in an exemplary embodiment, tamper assembly 106A may be substituted for tamper 106 of FIGS. 1A and 2. To this end, the tamper assembly 106A may have outer dimensions that are about equal to or smaller than the tamper 106 detailed above, thus facilitating replacement of tamper 106 with tamper 106A. Accordingly, tamper assembly 106A is configured to fit in carrier tube 102 as is tamper 106.

However, the tamper assembly 106A includes a frame 1062 that is movably connected to the tamper body 1061. Specifically, frame 1062 is movably connected to hub 1064, and hub 1064 is fitted to stud 1063 via an interference fit, stud 1063 being connected to tamper body 1061 as may be seen. The frame 1062 serves as a handle that the user may grasp during application of the closure device 20 to the recipient. In some embodiments, the frame 1062 is provided with knurling or tread grips or the like to facilitate grasping by the user. The hub 1064 is spring loaded by spring 1065 in the proximal direction of the deployment instrument 100. That is, with respect to FIG. 669, the spring 1064 forces the hub 1064 to the right, relative to the frame 1062. Another way of describing this is that the spring 1065 forces the frame 1062 to the left, relative to the hub 1064.

The proximal end of the tamper body 1061 is connected to the hub 1064 of the tamper assembly 106A as may be seen. Thus, the spring 1065 indirectly spring loads the carrier tube tamper body 1061 in the distal direction of the deployment instrument 100 relative to the frame 1062. In an exemplary embodiment, the spring 1065 permits the force by which the lock 36 is tamped to be controlled/ensures that sufficient force and not too much force is applied to the lock during deployment of the closure device 20, as will now be detailed.

During application of the closure device 20, the tamper 106A is ejected from the carrier tube 102 (as is the case with tamper 106) because the end of the tamper 106A catches on the tag 100. In this regard, housing 1062 may be configured to permit tag 100 to catch on the frame 1062. Any compression of spring 1065 resulting from tag 100 catching on frame 1062 is minimal with respect to sufficiently ejecting tamper 106A. Moreover, frame 1062 is configured to not interfere with filament 34 thus permitting the tamper 106A to be easily moved relative to filament 34. The user then grips the tamper 106A and applies a force to the tamper 106A in the distal direction (towards the recipient). The user applies this force by pushing on frame 1062 with a force sufficient to overcome the resistance to movement of the lock 36 relative to the filament 34 due to the protrusions 36B. The lock is moved along the filament 34 while applying a tension to the filament 34 in the opposite direction. In an exemplary embodiment, the user pushes on frame 1062 with sufficient force to move frame 1062 relative to the tamper body 1061 so that the frame 1062 bottoms out with respect to the hub 1064, as may be seen in FIG. 71. This ensures that a minimum force has been applied to the lock 36 during the tamping operation. In an exemplary embodiment, this minimum force is greater than the force required to move lock 36 relative to filament 34. Also, in an alternate embodiment, the compression of the spring 1065 provides an indication to the user that resistance to movement of the tamper assembly 106A in the distal direction is increasing. Moreover, the spring 1065 provides a certain amount of cushioning upon the tamper body 1061 striking the lock 36, as compared to what might otherwise be a sudden spike in the resistance against the tamper body 1061.

In an alternate embodiment of the present invention, the tamper assembly 106A includes an indicator 128 as may be seen in FIG. 71 corresponding to indicator 128 detailed above that provides an indication to the user that the hub 1064 has bottomed out within the frame 1062. As the hub 1064 moves relative to the frame 1062/the frame 1062 moves relative to the hub 1064, the stylus is forced upwards, relative to FIG. 71. Once the hub 1064 clears the stylus (which is or is about the point where the hub 1064 bottoms out in the frame 1062), as may be seen in FIG. 71, the stylus springs back downward (relative to FIG. 70). This makes a clicking noise which may be heard and/or felt by the user. Alternatively or in addition to this, a visual indicator 136 extends out of the housing 134 as the hub 1064 passes the stylus 130. Once the hub 1064 passes the stylus, the visual indicator 136 is withdrawn into the housing 134, its disappearance a visual indicator to the user that the hub 1064 has or is about to bottom out. This provides the user an indication that he or she should stop moving the tamper assembly 106A towards the recipient and/or continue to do so with additional caution.

In an alternate embodiment, the indicator 128 is configured to provide an indication when the hub 1064 has moved away from its bottomed out position. That is, the user may receive two indications—one indication when the 1064 bottoms out/about bottoms out and one indication when hub 1064 moves from its bottomed out position. This provides the user with an indication that, in the first instance, any additional movement of the tamper assembly 106A towards the recipient will not be cushioned by the spring 1065, and in the second instance, that the user has decreased the force with which he or she is pushing the lock 36 from that present when the hub 1064 bottomed out.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with any future claims and their equivalents.

What is claimed is:

1. A method of making a closure device for sealing a percutaneous puncture in a wall of a body passageway, the method comprising:
   coupling a filament to an anchor, the anchor configured to be brought into engagement with the wall of the body passageway, and coupling the filament to an expandable plug such that the filament extends through the anchor and the plug;
   coupling a lock to a lock starting portion of the filament; and
   crimping the lock while the lock is spaced from the plug, wherein crimping the lock includes applying a compressive force to the lock in a direction transverse to a longitudinal axis of the filament, wherein the compressive force is sufficient to deform one or more portions of the lock so that the one or more portions of the lock squeeze the lock starting portion of the filament,
   wherein the lock frictionally engages the filament when the lock slides between the lock starting portion of the filament and the plug, and
   wherein after crimping the lock, the lock is configured to only slide from the lock starting portion towards the plug.

2. The method of claim 1, wherein the compressive force is sufficient to increase the frictional engagement between the lock and the filament.

3. The method of claim 1, wherein the crimping of the lock occurs before the lock slides from the lock starting portion of the filament towards the plug.

4. The method of claim 1, wherein the crimping of the lock occurs before the lock comes into contact with the plug.

5. The method of claim 1, the method further comprising: after crimping the lock, testing the lock to determine a force required to slide the lock along the filament.

6. The method of claim 5, the method further comprising: comparing the determined force to a predetermined value; and
if the determined force is less than or equal to the predetermined value, re-crimping the lock, wherein re-crimping the lock increases the force required to slide the lock along the filament relative to the determined force.

7. The method of claim 6, wherein re-crimping the lock includes re-crimping the lock using a second compressive force greater than the first compressive force.

8. The method of claim 7, wherein the first compressive force is a minimum amount of force applied to the lock along the longitudinal axis of the filament to slide the lock from the lock starting position towards the plug to a second position, and wherein re-crimping the lock includes re-crimping the lock at the second position.

9. The method of claim 1, wherein the compressive force is sufficient to deform one or more portions of the lock so that the one or more portions of the lock protrude into the lock starting portion of the filament.

10. The method of claim 9, wherein the lock includes an opening extending through the lock through which the filament slides, and wherein the one or more portions of the lock protruding into the lock starting portion of the filament extend into the opening.

11. The method of claim 10, wherein the one or more deformed portions of the lock protrude into the opening, thereby forming an interference with the filament as it slides through the opening.

12. A method of making a closure device for sealing a percutaneous puncture in a wall of a body passageway, the method comprising:
coupling a lock to a lock starting portion of a filament; and
applying a compressive force to the lock in a direction transverse to a longitudinal axis of the filament, wherein the compressive force is sufficient to deform one or more portions of the lock so that the one or more portions of the lock squeeze the lock starting portion of the filament;
wherein after applying the compressive force to the lock, the lock is configured to only slide from the lock starting portion towards the wall of the body passageway.

13. The method of claim 12, further comprising:
coupling the filament to an expandable plug such that the filament extends through the plug; and
sliding the lock along the filament towards the plug.

14. The method of claim 13, further comprising:
sliding the lock along the filament towards the plug occurs after applying the compressive force to the lock.

15. The method of claim 13, wherein the compressive force applied to the lock is not applied by the plug.

16. The method of claim 13, wherein applying the compressive force to the lock occurs before the lock comes into contact with the plug.

17. The method of claim 12, further comprising:
testing the lock to determine a force required to slide the lock along the filament;
comparing the determined force to a predetermined value; and
if the determined force is less than or equal to the predetermined value, re-crimping the lock, wherein re-crimping the lock increases the force required to slide the lock along the filament relative to the determined force.

18. The method of claim 12, wherein the compressive force is sufficient to deform one or more portions of the lock so that the one or more portions of the lock protrude into the lock starting portion of the filament.

19. The method of claim 18, wherein the lock includes an opening extending through the lock through which the filament slides, and wherein the one or more portions of the lock protruding into the lock starting portion of the filament extend into the opening.

20. The method of claim 19, wherein the one or more deformed portions of the lock protrude into the opening, thereby forming an interference with the filament as it slides through the opening.

21. A closure device system configured to seal a percutaneous puncture in a wall of a body passageway, the closure device comprising:
a filament coupled to an anchor, the anchor configured to be brought into engagement with the wall of the body passageway;
an expandable plug, the expandable plug configured to fill the puncture; and
a lock, wherein the plug is positioned between the anchor and the lock along the filament, wherein at least the lock is coupled to the filament such that the lock can be moved along a portion of the filament, wherein the lock is crimped while the lock is at a first position along the filament spaced apart from the plug by a distance along the filament so as to increase a resistance of the lock when moving along the portion of the length of the filament, and wherein the lock is configured to slide only in one direction along the filament, from the first position towards the plug.

22. The closure device system of claim 21, wherein the lock is deformed before the lock comes into contact with the plug.

23. The closure device system of claim 21, wherein the lock is deformed using a crimping tool.

24. The closure device system of claim 21, further comprising:
a force gauge configured to test the lock to determine a force required to slide the lock along the filament; and
a crimping mandrel configured to deform the lock, wherein after the force gauge tests the lock and the determined force is compared to a predetermined value, if the determined force is below or equal to the predetermined value, the lock is deformed using the crimping mandrel, wherein deforming the lock increases the force required to slide the lock along the filament relative to the determined force.

25. The closure device system of claim 24, wherein if the determined force remains below or equal to the predetermined value after the force gauge is used to re-test the lock after the lock is deformed, the lock is re-deformed.

* * * * *